US012662493B2

(12) United States Patent
Liu et al.

(10) Patent No.: US 12,662,493 B2
(45) Date of Patent: Jun. 23, 2026

(54) NON-IMMUNOSUPPRESSIVE FK506 ANALOGS AND USE THEREOF

(71) Applicant: The Johns Hopkins University, Baltimore, MD (US)

(72) Inventors: Jun O. Liu, Clarksville, MD (US); Zhaoli Sun, Perry Hall, MD (US); Brandon J. Peiffer, Rosedale, MD (US); Yuefan Wang, Nottingham, MD (US); Le Qi, Baltimore, MD (US); Zufeng Guo, Baltimore, MD (US); Hanjing Peng, Columbia, MD (US); Ali Ahmadi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1025 days.

(21) Appl. No.: 17/424,441

(22) PCT Filed: Jan. 23, 2020

(86) PCT No.: PCT/US2020/014699

§ 371 (c)(1),
(2) Date: Jul. 20, 2021

(87) PCT Pub. No.: WO2020/154455

PCT Pub. Date: Jul. 30, 2020

(65) Prior Publication Data

US 2022/0251108 A1 Aug. 11, 2022

Related U.S. Application Data

(60) Provisional application No. 62/795,700, filed on Jan. 23, 2019.

(51) Int. Cl.

| | |
|---|---|
| ***C07D 498/18*** | (2006.01) |
| ***A61K 31/439*** | (2006.01) |
| ***A61K 31/706*** | (2006.01) |
| ***A61K 45/06*** | (2006.01) |
| ***A61P 17/02*** | (2006.01) |

(52) U.S. Cl.

CPC .......... *C07D 498/18* (2013.01); *A61K 31/439* (2013.01); *A61K 31/706* (2013.01); *A61K 45/06* (2013.01); *A61P 17/02* (2018.01)

(58) Field of Classification Search

CPC .............. A61K 2300/00; A61K 31/395; A61K 31/436; A61K 31/439; A61K 31/4427; A61K 31/4545; A61K 31/4709; A61K 31/5377; A61K 31/675; A61K 31/706; A61K 45/06; A61K 31/435; A61P 17/02; A61P 25/00; A61P 25/28; A61P 29/00; C07D 498/18; C07D 491/18; C07H 19/01

See application file for complete search history.

(56) References Cited

U.S. PATENT DOCUMENTS

| | | | | |
|---|---|---|---|---|
| 5,284,877 | A | 2/1994 | Organ et al. | |
| 10,420,751 | B2 * | 9/2019 | Sun ...................... | A61K 38/193 |
| 2006/0160838 | A1 | 7/2006 | Schlachter et al. | |

FOREIGN PATENT DOCUMENTS

| | | | |
|---|---|---|---|
| EP | 0 626 385 | A1 | 11/1994 |
| WO | WO 1991/013889 | A1 | 9/1991 |
| WO | WO 199200313 | A1 | 1/1992 |
| WO | WO 200028011 | A2 | 5/2000 |
| WO | WO 2006078724 | A2 | 7/2006 |
| WO | WO 2012054638 | A2 | 4/2012 |
| WO | WO 2015106283 | A1 | 7/2015 |
| WO | WO 2018087677 | A1 | 5/2018 |
| WO | WO 2018152451 | A1 | 8/2018 |

OTHER PUBLICATIONS

Marinec PS, Evans CG, Gibbons GS, Tarnowski MA, Overbeek DL, Gestwicki JE. Synthesis of orthogonally reactive FK506 derivatives via olefin cross metathesis. Bioorg Med Chem. Aug. 15, 2009;17(16):5763-8. (Year: 2009).*

Clemons et al (Chemistry & Biology, vol. 9, 49-61, Jan. 2002) in (Year: 2002).*

Patel et al (Int J Pharm Investig. Oct.-Dec. 2012; 2(4): 169-175) (Year: 2012).*

Patani et al (Chem. Rev. 1996, 96, 3147-3176) (Year: 1996).*

JP Office Action in Japanese Application No. 2021-543343, dated Dec. 12, 2023, 6 pages (with English translation).

CN Office Action in Chinese Application No. 202080022171.8, dated Oct. 12, 2023, 14 pages (with English abstract).

Marinec et al., "Synthesis of Orthogonally Reactive FK506 Derivatives via Olefin Cross Metathesis", Bioorg Med Chem., Aug. 2009, 17(16): 5763-5768.

CA Office Action in Canadian Application No. 3,127,613, dated Dec. 18, 2023, 8 pages.

Clemons et al., "Synthesis of Calcineurin-Resistant Derivatives of FK506 and Selection of Compensatory Receptors", Chemistry & Biology, Jan. 2002, 9: 49-61.

Lin et al., "Pharmacological Mobilization of Endogenous Stem Cells Significantly Promotes Skin Regeneration after Full-Thickness Excision: The Synergistic Activity of AMD3100 and Tacrolimus", Journal of Investigative Dermatology, May 2014, 134: 2458-2468.

Wang et al., "One-Step Heck Reaction Generates Nonimmunosuppresive FK506 Analogs for Pharmacological BMP Activation," ACS Med. Chem. Lett. 2019, 10, pp. 1279-1283.

Peiffer, "Pre-Clinical Research and Development of Novel FKBP 12 Antagonists for Enhanced Wound Healing and Regenerative Therapy," 155 pages, Feb. 2019.

(Continued)

*Primary Examiner* — Jean P Cornet

(74) *Attorney, Agent, or Firm* — DLA Piper LLP (US)

(57) ABSTRACT

The present invention provides a new class of non-immunosupressive FK506 analogs which are FRBP-selective, small-molecule BMP agonists with modest potency therepeutics for tissue repair and regeneration. Also disclosed herein are methods for making and use of these compounds.

6 Claims, 21 Drawing Sheets

(56) References Cited

OTHER PUBLICATIONS

Peiffer et al., Activation of BMP Signaling by FKBP 12 Ligands Synergizes with Inhibition of CXCR4 to Accelerate Wound Healing, Cell Chemical Biology 26, pp. 652-661, May 16, 2019.

* cited by examiner

FK506

FKVP

| | 1 | 2 | 3 | FK506 |
|---|---|---|---|---|
| EC50 | 12.37 | 30.55 | 23.40 | 34.45 |

FK506

FKVP

SLF

CsA

| INPUT/PULLDOWN | I | I | I | I | I | I | P | P | P | P | P | P |
|---|---|---|---|---|---|---|---|---|---|---|---|---|
| DMSO | X | | | | | | X | | | | | |
| FKVP (10uM) | | X | | | | | | X | | | | |
| FK506 (10uM) | | | X | | | | | | X | | | |
| RAPAMYCIN (10uM) | | | | X | | | | | | X | | |
| BMP-9 (25ng/mL) | | | | | X | | | | | | X | |
| BMP-4 (50ng/mL) | | | | | | X | | | | | | X |

NON-IMMUNOSUPPRESSIVE FK506 ANALOGS AND USE THEREOF

REFERENCE TO RELATED APPLICATIONS

This application claims the benefit of U.S. Provisional Patent Application No. 62/795,700, filed on Jan. 23, 2019, and is hereby incorporated by reference for all purposes as if fully set forth herein.

BACKGROUND OF THE INVENTION

Wounding due to accidents, diseases, and armed conflict is one of the most common medical problems. Cost of care for chronic, non-healing wounds associated with severe burns and diseases such as diabetes has been estimated to exceed 50 billion dollars per year (Fife et al., 2012). Chronic wounds make the human body more susceptible to infection, increasing the risk of acquiring opportunistic pathogens that can lead to sepsis. Thus, accelerating wound healing (WH) can reduce the risk of infection, improving the mortality and morbidity rates of wounded patients. However, there are limited options to shorten wound healing, calling for development of new therapies.

The inventors have previously reported the discovery of a synergistic drug combination for the acceleration of cutaneous WH (Lin et al., 2014) and the induction of long-term allograft survival through host repopulation (Okabayashi et al., 2011, Hu et al., 2016, Cameron et al., 2016). The combination of two FDA-approved drugs, Tacrolimus (FK506) and Plerixafor (AMD3100), reduced the complete healing time by 25% in mice with four circular full-thickness excisional wounds, which is unprecedented by existing therapeutic modalities. Accelerated WH is accompanied by the mobilization of bone marrow (BM)-derived stem cells (CD133, CD34, and cKit) and the recruitment of CD133 stem cells into wound sites, as well as augmented stromal derived factor 1 (SDF-1), fibroblast growth factor (FGF), and vascular endothelial growth factor (VEGF) release in granulation tissues (Lin et al., 2014).

The underlying molecular mechanism by which the combination of FK506 and AMD3100 (AF) accelerates WH has not been extensively studied. AMD3100 is a selective antagonist of the chemokine receptor CXCR4 (Hatse et al., 2002) and has been used clinically to drive hematopoietic stem cells (HSCs) out of the bone marrow (BM) into the peripheral blood (Liles et al., 2003) where they can be recovered and preserved until the completion of ablative irradiation and/or chemotherapy. In addition to HSCs, the injection of AMD3100 augmented the mobilization of BM derived endothelial progenitor cells (EPCs), which was associated with more rapid neovascularization and functional recovery after myocardial infarction in mice (Jujo et al., 2010, Balaji et al., 2013). However, increased number of circulating stem cells by AMD3100 treatment alone exhibited only slightly faster healing due to reduced recruitment in wound sites (Lin et al., 2014).

In contrast to AMD3100, the precise role played by low-dose FK506 in the combination treatment (AF) has remained a mystery. FK506, a macrolide produced by the bacteria *Streptomyces* tsukubaensis, is an immunosuppressant widely used for prevention of transplant rejection as well as treatment of certain autoimmune disorders (Tanaka et al., 1987; Fung et al., 2004). The underlying mechanism for the immunosuppressive activity of FK506 has been well established. At the cellular level, FK506 inhibits the activation of T helper cells. At the pathway level, it blocks the intracellular signal transduction emanating from the T cell receptor leading to transcriptional activation of IL-2 and other cytokine genes. At the molecular level, it binds to FKBP12 and other members of the FKBP family before the binary FKBP-FK506 complex associates with and inhibits the activity of the protein phosphatase activity of calcineurin, preventing calcium-dependent dephosphorylation of the nuclear factor of activated T-cells (NFAT) (Liu et al., 1991; Griffith et al., 1995; Kissinger et al., 1995).

A possible underlying mechanism for FK506 in WH is through inhibition of calcineurin. However, it has been shown that topical FK506 has a detrimental effect on WH (Schaffer et al., 1998). Furthermore, we have shown that animals treated with low-dose FK506 (0.1 mg/kg) alone exhibited slightly faster healing compared to the saline control group, but the standard dose of FK506 (1 mg/kg) for immunosuppression delayed healing time, leaving unanswered the question of whether calcineurin inhibition is responsible for the effect of FK506 on WH.

Though FKBP12 plays an accessary role in the immunosuppressive activity of FK506, it has also been shown to inhibit BMP type 1 receptor activation (Wang et al., 1996). Importantly, this interaction could be relieved by FK506 (Spiekerkoetter et al., 2013). BMP signaling has not yet been directly linked to any stage of wound healing, although it has been reported that epithelial cells down-regulate many BMP receptors in response to injury (Lewis et al., 2014). Conversely, it has been recently reported that enhanced BMP signaling within myofibroblasts may promote scarless wound healing (Plikus et al., 2017). BMPs have been demonstrated to produce a pro-inflammatory phenotype in endothelial cells, thereby increasing leukocyte adhesion and SDF-1 secretion (Csiszar et al., 2006; Young et al., 2012). Upon activation, BMP receptors phosphorylate and activate the SMAD transcription factors 1, 5, and 8. One major target gene of these SMADs is inhibitor of differentiation 1 (ID-1), which inhibits transcription of several genes related to embryogenesis and stem cell self-renewal. Previous studies have examined some of the downstream effects of BMP receptor activation following FK506 treatment, which is accompanied by increases in SMAD1 and SMAD5 (denoted SMAD1/5) and/or SMAD8 (denoted SMAD1/5/8) phosphorylation in skeletal muscle cells (Spiekerkoetter et al., 2013) and human synovial stromal (hSSC) cells (Tateishi et al, 2007). Additionally, increases were observed in MAPKK phosphorylation and ID-1 expression, and the activity of FK506 was sufficient to rescue endothelial dysfunction in mice induced by a conditional BMP receptor type 2 (BMPR2) knockout (Spiekerkoetter et al., 2013). It has been reported that FK506 upregulated phosphorylation of SMADs downstream of the TGF-β signaling pathway (SMAD 2 and 3) in smooth muscle cells (Giordano et al Cardiovasc Res. 2008; Bennet et al. J Clin Med. 2016). However, downstream transcriptional activity was only seen in the presence of supplemented exogenous TGF-β (Spiekerkoetter et al., 2013; Wang et al., 1996). In another study, it was shown that FK506 increased expression of the TGF-β type 3 co-receptor endoglin, and stimulated both migratory and angiogenic activity of endothelial cells (Albiñana et al., 2011). Together, these observations raised the possibility that FK506 may exert its WH effect through FKBP12, independent of calcineurin inhibition.

Therefore, there still exists a need for compounds and compositions that can improve wound healing.

SUMMARY OF THE INVENTION

The present inventors have now synthesized novel non-immunosuppressive FK506 analogs that retain FKBP binding and lack calcineurin inhibition activity (FIG. 1). The newly synthesized FK506 analogs were found to activate BMP signaling in lymphocytes and endothelial cells through disruption of FKBP12-BMPR1 interaction. Moreover, the inventors can now show that the combination of these FK506 analogs and AMD3100 was found to accelerate wound healing in diabetic rats in a BMP receptor-dependent manner.

The newly synthesized FK506 analogs FK506 analogs display variable immunosuppressive qualities while they all activate a BMP pathway reporter in Jurkat cells with similar potency to FK506. Moreover the derivatives show structure-dependent effects in NFAT reporter inhibition in Jurkat cells.

In accordance with an embodiment, the present invention provides a compound of formula I:

(I)

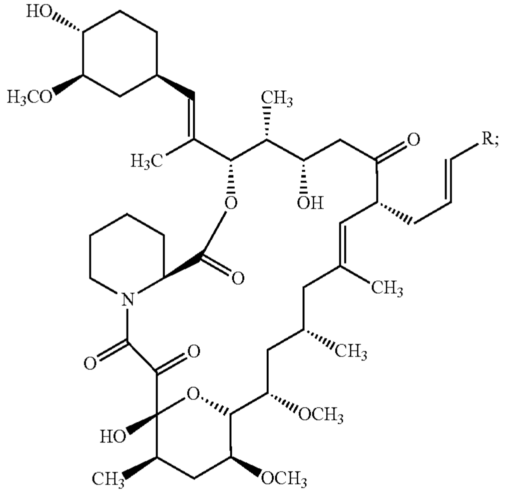

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur.

In accordance with an embodiment, the present invention provides a compound of formula I, wherein R is selected from the group consisting of:

(1)

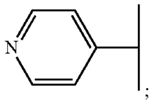

(2)

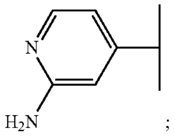

(3)

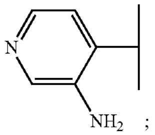

-continued (4)

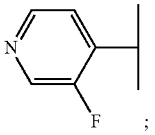

(5)

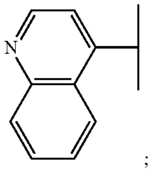

(6)

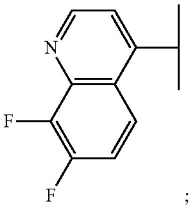

(7)

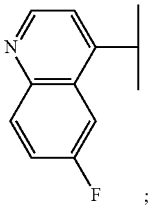

(8)

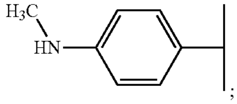

(9)

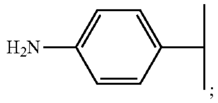

(10)

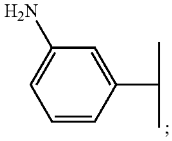

(11)

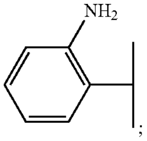

(12)

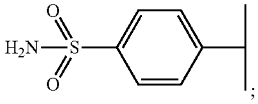

(13)

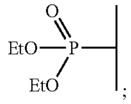

-continued (14)

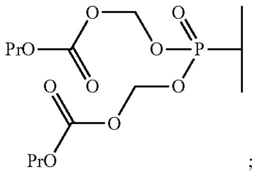

;

(15)

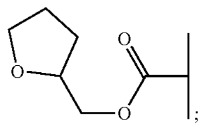

;

(16)

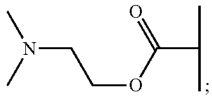

;

(17)

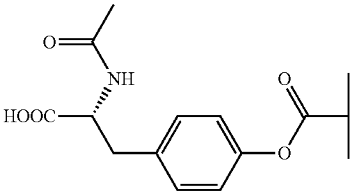

;

(18)

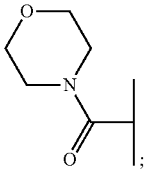

;

(19)

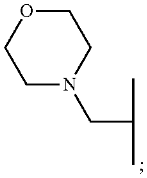

; and (20)

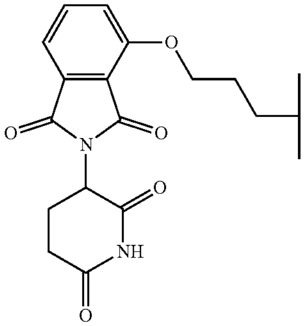

.

In accordance with an embodiment, the present invention provides a composition comprising a compound of formula I:

(I)

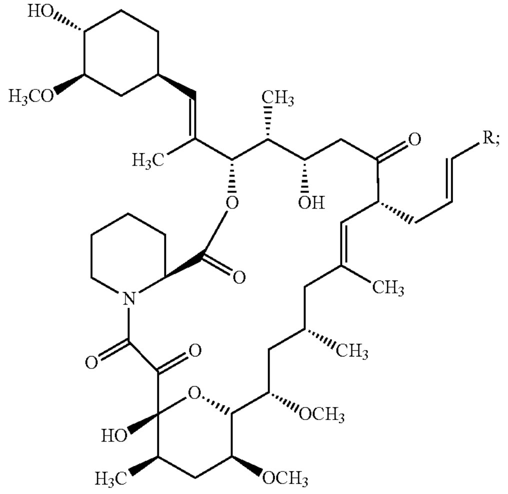

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur; and a pharmaceutically acceptable carrier.

In accordance with an embodiment, the present invention provides a composition comprising a compound of formula I, wherein R is selected from the group consisting of:

(1)

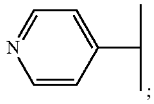

;

(2)

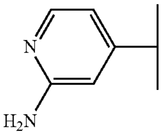

;

(3)

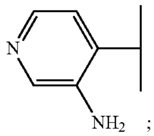

;

(4)

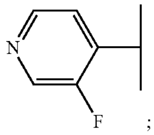

;

(5)

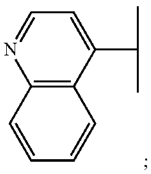

;

-continued
(6)
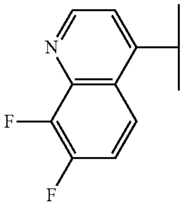
;
(7)
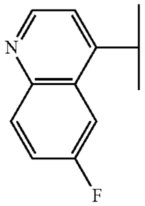
;
(8)
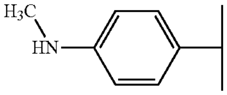
;
(9)
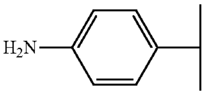
;
(10)
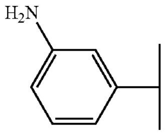
;
(11)
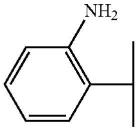
;
(12)
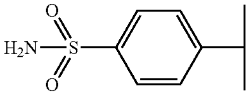
;
(13)
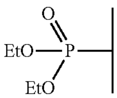
;
(14)
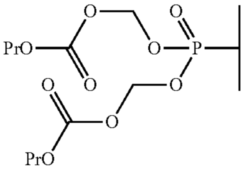
;
-continued
(15)
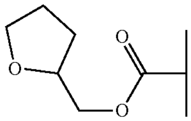
;
(16)
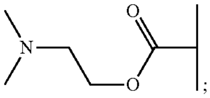
;
(17)
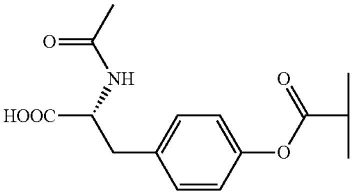
;
(18)
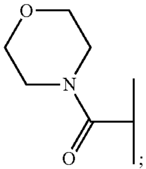
;
(19)
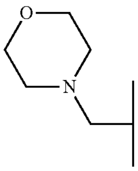
; and
(20)
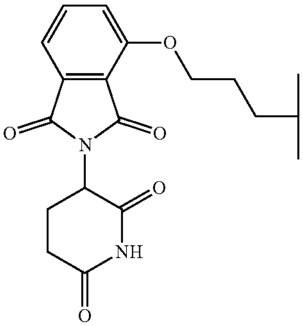
.
In accordance with a further embodiment, the present invention provides the compounds of formula 1, or compositions comprising the compounds of formula 1, and at least one or more biologically active agents.
In accordance with an embodiment, the present invention provides a composition comprising a compound of formula I:

(I)

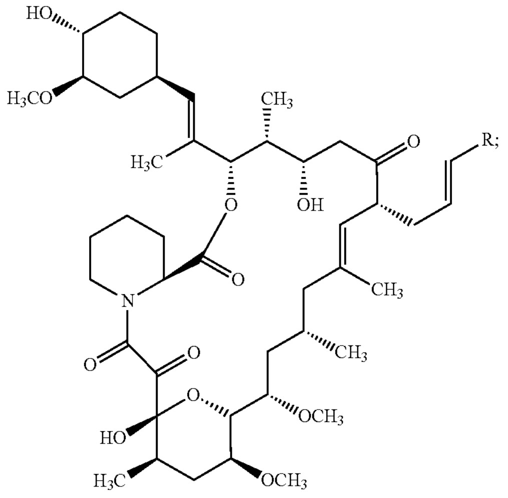

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur; at least one stem cell mobilizer; and a pharmaceutically acceptable carrier.

In accordance with an embodiment, the present invention provides a composition comprising a compound of formula I, wherein R is selected from the group consisting of:

(1)

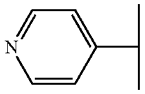

;

(2)

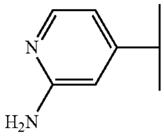

;

(3)

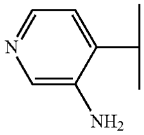

;

(4)

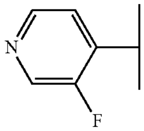

;

(5)

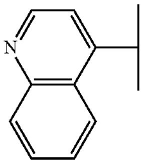

;

-continued (6)

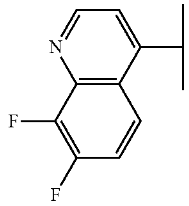

;

(7)

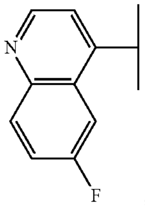

;

(8)

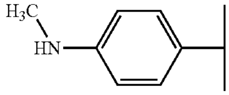

;

(9)

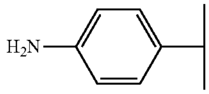

;

(10)

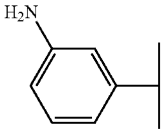

;

(11)

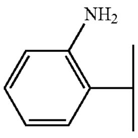

;

(12)

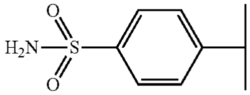

;

(13)

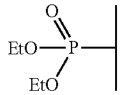

;

(14)

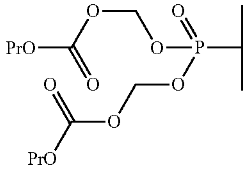

;

(15)

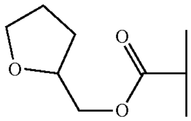

;

-continued (16)

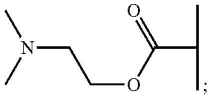

;

(17)

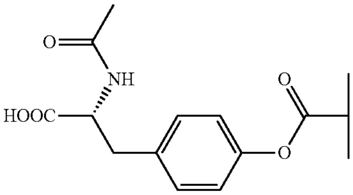

;

(18)

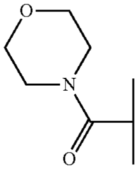

;

(19)

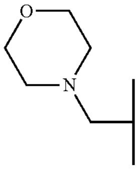

; and (20)

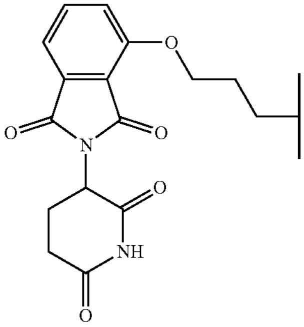

.

In a specific embodiment, the stem cell mobilizer comprises a CXCR4 antagonist. For example, the CXCR4 antagonist can comprise AMD3100, TG-0054, or AMD3465.

In accordance with an embodiment, the present invention provides a method for treating tissue injury in a subject comprising administering to the subject an effective amount of a compound of formula I:

(I)

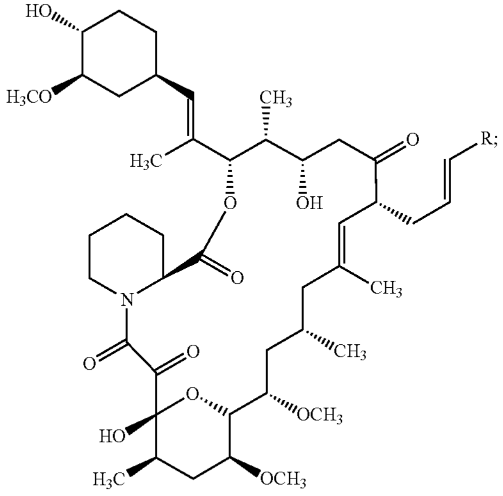

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur; and an effective amount of at least one stem cell mobilizer.

In accordance with another embodiment, the present invention provides a method for treating tissue injury in a subject comprising administering to the subject a composition comprising an effective amount of a compound of formula I, an effective amount of at least one stem cell mobilizer, and a pharmaceutically acceptable carrier.

In some embodiments, the present invention provides a method for treating tissue injury in a subject comprising administering to the subject a composition comprising an effective amount of a comprising a compound of formula I, wherein R is selected from the group consisting of (1)

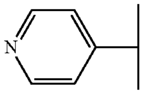

;

(2)

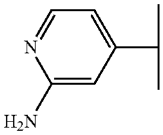

;

(3)

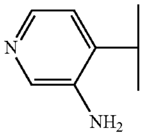

;

(4)

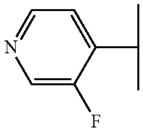

;

-continued (5)

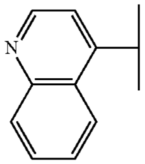

;

(6)

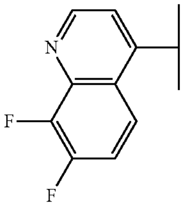

;

(7)

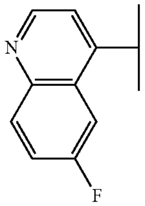

;

(8)

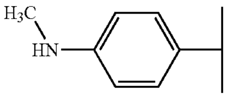

;

(9)

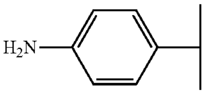

;

(10)

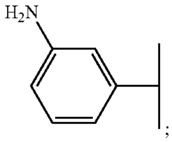

;

(11)

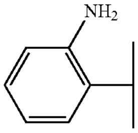

;

(12)

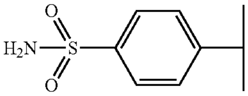

;

(13)

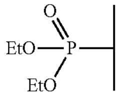

;

(14)

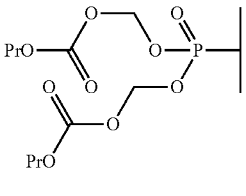

;

-continued (15)

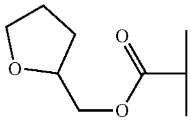

;

(16)

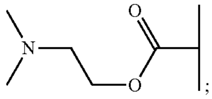

;

(17)

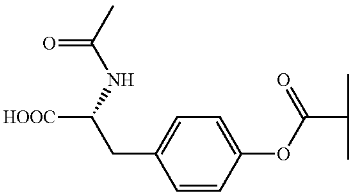

;

(18)

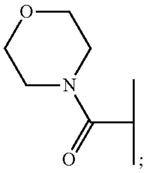

;

(19)

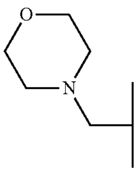

; and (20)

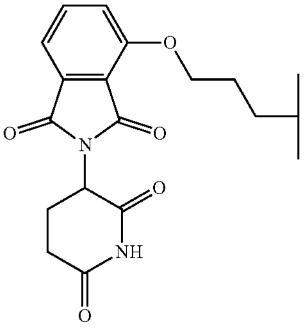

.

In accordance with a further embodiment, the present invention provides a method for treating tissue injury in a subject comprising administering to the subject a composition comprising an effective amount of a compound of formula I, an effective amount of at least one stem cell mobilizer, at least one additional biologically active agent, and a pharmaceutically acceptable carrier.

In accordance with an embodiment, the present invention provides a method for making an aryl substituted FK506 molecule, comprising the steps of: a) adding a sufficient quantity of FK506 to a mixture comprising a sufficient quantity an aryl halide in the presence of a palladium catalyst and a base in a polar aprotic solvent; b) heating the mixture for a sufficient time for the aryl halide to react with FK506 to create an aryl substitution on the FK506 molecules and c) isolate the aryl substituted FK506 product.

BRIEF DESCRIPTION OF THE DRAWINGS

(FIG. 2A) Cell viability after 72-hour analog treatment in HUVEC cells. (FIG. 2B) All analogs activate a BMP pathway reporter in Jurkat cells with similar potency to FK506. (FIG. 2C) Derivatives show structure-dependent effects in NFAT reporter inhibition in Jurkat cells. Error bars represent standard deviation from mean for all measurements (n=3), and absorbance/luminescence values were normalized to DMSO treated cells.

(FIG. 4A) Close-up of FK-506 terminal olefin with calcineurin. (FIG. 4B) Steric effect of FK P with calcineurin.

(FIG. 5A) Chemical structures of FK506, FKVP, SLF, and CsA. (FIG. 5B) Resazurin-based cell viability assay of Jurkat cells after 3 days of FKVP or FK506 treatment (n=3). Absorbance values were normalized to DMSO control. Error bars represent standard deviation. (FIG. 5C) NFAT-Luciferase reporter activity of PMA/Ionomycin-activated Jurkat cells is inhibited by FK506 and CsA, but not by FKVP and SLF. Dose response curves were obtained by treating Jurkat cells, expressing the NFAT-luciferase reporter gene with serial dilutions of indicated compounds and the relative luciferase activities were determined upon normalization to DMSO control values. (n=3).

(FIG. 8A) FKVP blocks FK506 inhibition of calcineurin-mediated NFAT dephosphorylation (lower band), (FIG. 8B) as well as inhibition of mTOR-mediated S6 phosphorylation by rapamycin.

(FIG. 9A) The wound model: four circular excisional wounds (8-mm in diameter) were created on the dorsal of GK rats. (FIG. 9B) Representative photographs of wounds in GK rats for each treatment group (AF=AMD3100+FK506, AV=AMD3100+FKVP), at days 0, 6, 12, 18 and 24. (FIG. 9C) Quantitative analysis of complete healing time in GK rats. All data represented by mean±SEM.

(FIG. 10A) BMP-response-element (BRE) reporter activity in Jurkat cells after treatment with increasing amounts of FK506 and FKVP. This activity is strongly inhibited by the addition of 100 nM LDN-193182. TGF-β1 serves as negative control, while BMP4 shows strong induction of luciferase expression after 18 hours. Relative luciferase activities were determined upon normalization to DMSO control values. Error bars represent standard deviation from mean. (FIG. 10B) Dose-dependent induction of SMAD1/5 phosphorylation by FKVP in Jurkat cells. (FIG. 10C) BMPR1-selective inhibitor LDN-193189 inhibits SMAD1/5 phosphorylation induced by either BMP-4 or FKVP in Jurkat cells.

(FIG. 15A) Western blot of SMAD1/5 phosphorylation after 2 hr. treatment with BMP-4, FKVP, LDN combination treatments in HUVEC cells. (FIG. 15B) Time-course Western blot of HUVEC cells treated with 200 nM FKVP and blotted for SMAD1/5 phosphorylation and (FIG. 15*c*) ID-1 expression.

(FIG. 16A) Induction of SMAD1/5 phosphorylation by FKVP and BMP-4 in wild type and different FKBP isoform knockout cells. (FIG. 16B) Activation of BMP pathway reporter by FKVP and FK506 in different FKBP isoform knockout cells and inhibition of the reporter gene activation by LDN (n=3). Relative luciferase activities were determined upon normalization to DMSO control values. Error bars represent standard deviation from mean. (FIG. 16C) Expression of FKBP12-SNAP fusion protein restores BMP pathway activation by FKVP and FK506 in FKBP12KO Jurkat cells (n=3). (FIG. 16D) Pulldown of ALK receptors using FKBP12-SNAP in conjunction with SNAP-functionalized beads in the absence and presence of FKVP.

(FIG. 18A) Representative photographs of wounds in GK rats treated with saline, LDN, AF or AF plus LDN showing difference between AF and AF plus LDN beginning at day 12. (FIG. 18B) Quantitative analysis of complete healing time in GK rats. All data represented by mean±SEM. (FIG. 8C) Representative immunohistochemical stainings for the stem cell marker CD133 in granulation tissues of GK rats at day 7. The rats receiving AF treatment had significantly higher number of CD133 cells (brown) in granulation tissues compared to the saline control group, while LDN treatment dramatically reduced the number of CD133 stem cells in the wound sites.

DETAILED DESCRIPTION OF THE INVENTION

Figure 1:
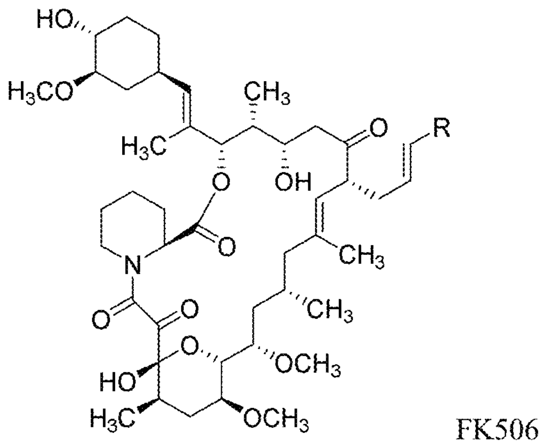
FIG. 1 depicts the chemical structures of FK 506 and FKVP.
Figure 1:
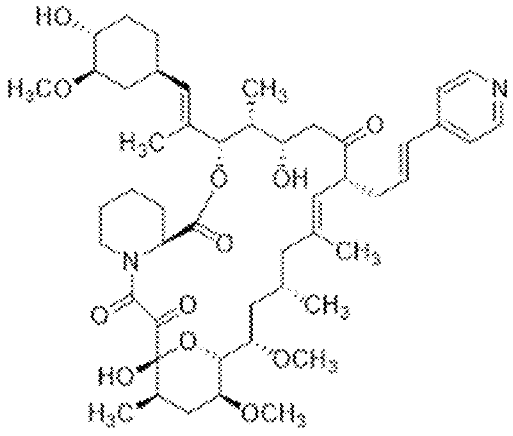

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

In accordance with an embodiment, the present invention provides a compound of formula I.

(I)

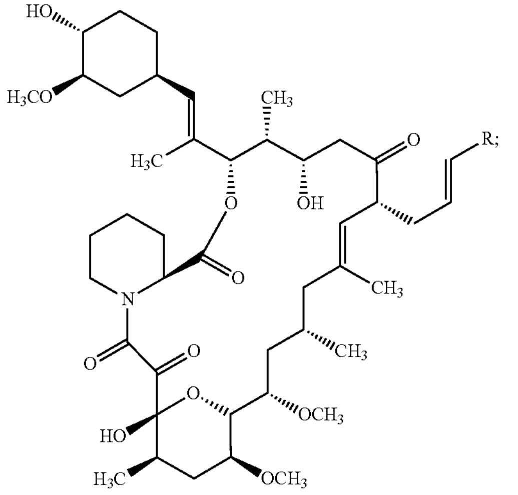

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur.

The non-immunosuppressive compounds of formula I are derived from the immunosuppressive agent, Tacrolimus. Tacrolimus (also FK-506 or Fujimycin) is an immunosuppressive drug that is mainly used after allogeneic organ transplant to reduce the activity of the patient's immune system and so lower the risk of organ rejection. It reduces interleukin-2 (IL-2) production by T-cells. It is also used in a topical preparation in the treatment of severe atopic dermatitis (eczema), severe refractory uveitis after bone marrow transplants, and the skin condition vitiligo. It is a 23-membered macrolide lactone discovered in 1984 from the fermentation broth of a Japanese soil sample that contained the bacteria *Streptomyces* tsukubaensis. The drug is sold under the trade names Prograf® given twice daily (intravenous), Advagraf® a sustained release formulation allowing once daily dosing (oral), and Protopic® the topical formulation.

In accordance with an embodiment, the present invention provides a compound of formula I, wherein R is selected from the group consisting of (1)

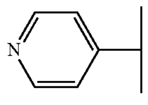

;

(2)

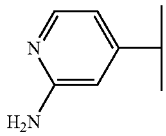

;

(3)

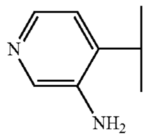

;

(4)

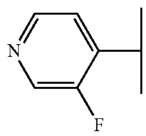

;

(5)

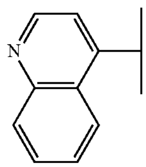

;

(6)

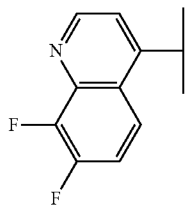

;

-continued (7)

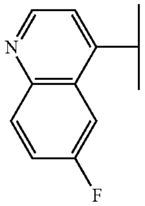

;

(8)

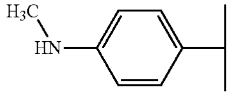

;

(9)

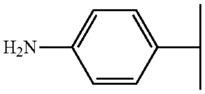

;

(10)

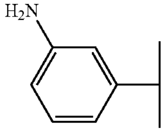

;

(11)

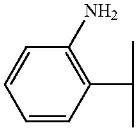

;

(12)

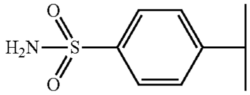

;

(13)

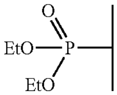

;

(14)

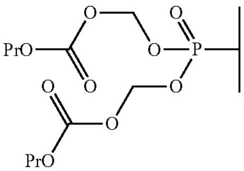

;

(15)

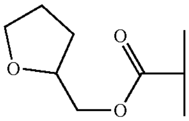

;

(16)

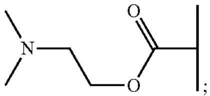

;

-continued (17)

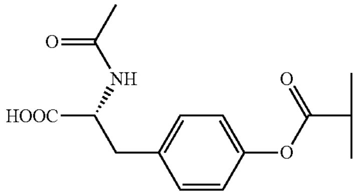

;

(18)

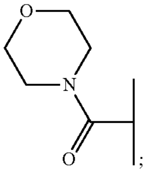

;

(19)

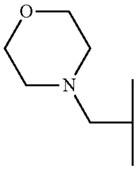

; and (20)

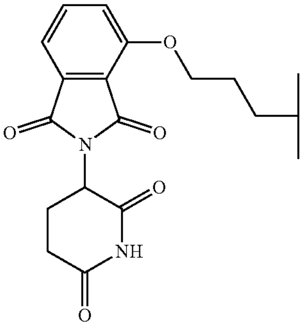

.

The term "aliphatic" is an art-recognized term and includes linear, branched, and cyclic alkanes, alkenes or alkynes. In certain embodiments, aliphatic groups in the present invention are linear or branched and have from 1-about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The term "aralkyl" is art-recognized, and includes aryl groups (e.g., an aromatic or heteroaromatic group).

The terms "alkenyl" and "alkynyl" are art-recognized, and in an organic molecule, generally includes an atom of any element other than carbon or hydrogen. Illustrative heteroatoms include boron, nitrogen, oxygen, phosphorus, sulfur, and selenium.

The term "aryl" is art-recognized, and includes 5-, 6-, and 7-membered single ring aromatic groups that may include from zero to four heteroatoms, for example, benzene, pyrole, furan, thiophene, imidazole, oxazole, thiazole, triazole, pyrazole, pyridine, pyrazine, pyridazine and pyrimidine, and the like. Thos aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydyl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls, and/or heterocyclyls, or rings joined by non-cyclic moieties.

The terms "ortho," "meta" and "para" are art-recognized and apply to 1,2-, 1,3- and 1,4-disubstituted cyclohexanes, respectively. For example, the names 1,2-dimehtylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles, Heterocycclyl groups include, for example, thiophene, thianthrene, furan, pyran, isobenzofuran, chromene, xanthene, phenoxanthin, pyrrole imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphtyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones and the like. The heterocyclic ring may be substituted at one or more positions with such substituents as described above, as for example, halogen, alkyl aralkyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, -$CD_3$, —CN or the like.

The terms "polycyclyl" and polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hyroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, -$CD_3$, —CN or the like.

The term "carbocycle" is art recognized and includes an aromatic or non-aromatic ring in which each atom of the ring is carbon. The following art-recognized terms have the following meanings: "nitro" means —$NO_2$; the term "halogen" designates —F, —Cl, —Br, or —I; the term "sulfhydryl" means —SH; the term "hydroxyl" or "hydroxy" means —OH; and the term sulfonyl" means —$SO_2$—.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes and alkyl group, as defined above, having a sulfur radical attached thereto. In certain embodiments, the "alkylthio" moiety is represented by one of —S-alkyl, —S-alkenyl, —S-alkynyl and so on. Representative alkylthio groups include methylthio, ethylthio and the like.

The term "carbonyl" is art-recognized and includes a C═O structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms “sulfonamide,” “sulfamoyl,” “sulfonyl,” and “sulfoxido” are art-recognized and each can include a variety of R group substituents as described herein.

The terms phosphoramidite” and “phophonamidite” are art-recognized.

The term “selenoalkyl” is art-recognized and includes an alkyl group having a substituted seleno group attached thereto. Exemplary “selenoethers” which may be substituted on the alkyl are selected from one of Se-alkyl, —Se-alkenyl, —Se-alkynyl and so on.

Substitutions may be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

A hydrocarbon is an art recognized term and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase “protecting group” is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed, Greene et al., Protective Groups in Organic Synthesis 2nd ed., Wiley, New York, (1991), for example.

The definition of each expression, e.g., alkyl, aryl etc., when it occurs more than once in any structure, is intended to be independent of its definition elsewhere in the same structure unless otherwise indicated expressly or by the context.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

It will be understood that “substitution” or “substituted with” includes the implicit proviso that such substitution is in accordance with the permitted valency of the substituted atom and the substituent, and that the substitution results in a stable compound, e.g., which does not spontaneously undergo transformation, such as by rearrangement, cyclization, elimination, or other reaction.

The term “substituted” is also contemplated to include all permissible substituents of organic compounds such as the imide reagent of interest. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In accordance with an embodiment, the present invention provides a method for making an aryl substituted FK506 molecule, comprising the steps of: a) adding a sufficient quantity of FK506 to a mixture comprising a sufficient quantity an aryl halide in the presence of a palladium catalyst and a base in a polar aprotic solvent; b) heating the mixture for a sufficient time for the aryl halide to react with FK506 to create an aryl substitution on the FK506 molecules and c) isolate the aryl substituted FK506 product.

As used herein, the present invention provides a novel method for producing aryl substitutions to the FK506 molecule at the terminal alkenyl carbon (carbon 40) of the molecule. The present invention uses the Heck reaction. The Heck reaction (also called the Mizoroki-Heck reaction) is the chemical reaction of an unsaturated halide (or triflate) with an alkene in the presence of a base and a palladium catalyst (or palladium nanomaterial-based catalyst) to form a substituted alkene. It is named after Tsutomu Mizoroki and Richard F. Heck. Heck was awarded the 2010 Nobel Prize in Chemistry, which he shared with Ei-ichi Negishi and Akira Suzuki, for the discovery and development of this reaction. This reaction was the first example of a carbon-carbon bond-forming reaction that followed a Pd(0)/Pd(II) catalytic cycle, the same catalytic cycle that is seen in other Pd(0)-catalyzed cross-coupling reactions.

In some embodiments, the inventive methods are used to prepare the aryl substituted compounds of FK506 (compounds of formula I).

In some embodiments, the catalysts used in the inventive methods can be Typical catalysts and precatalysts include tetrakis(triphenylphosphine)palladium(0), palladium chloride, and palladium(II) acetate.

In some embodiments, the supporting ligands are used in the inventive methods are triphenylphosphine, PHOX and BINAP.

In some embodiments, the bases used in the inventive methods are triethylamine, potassium carbonate, tris(o-tolyl) phosphine, and sodium acetate.

In some embodiments, the aryl electrophile used in the inventive methods are halides, as well as a triflate as well as benzyl or vinyl halides.

In some embodiments, the inventive method occurs in the absence of oxygen.

In some embodiments, the inventive method occurs in a polar aprotic solvent. Examples of such solvents include N-methylpyrrolidone, THF, ethyl acetate, acetone, DMF, acetonitrile, DMSO and propylene carbonate.

In some embodiments, the inventive methods heat the reactants in the range of 80-130° C. In a preferred embodiment, the reaction is heated to about 100° C.

In some embodiments, the sufficient quantity of aryl halide to FK506 is in the range of 1 to 3 mole equivalents. In some embodiments, the sufficient quantity of palladium catalyst is about 2 to about 20 mol %. In some embodiments the sufficient quantity of base is between about 5 to about 30 mol % tris(o-tolyl)phosphine or trimethylamine.

In some embodiments, the aryl halides used in the inventive methods are selected from those shown in Table 1 below.

Table 1: A schematic of the inventive methods and the aryl halides that can be used with the inventive methods.
TABLE 1
A schematic of the inventive methods and the aryl halides that can be used with the inventive methods.
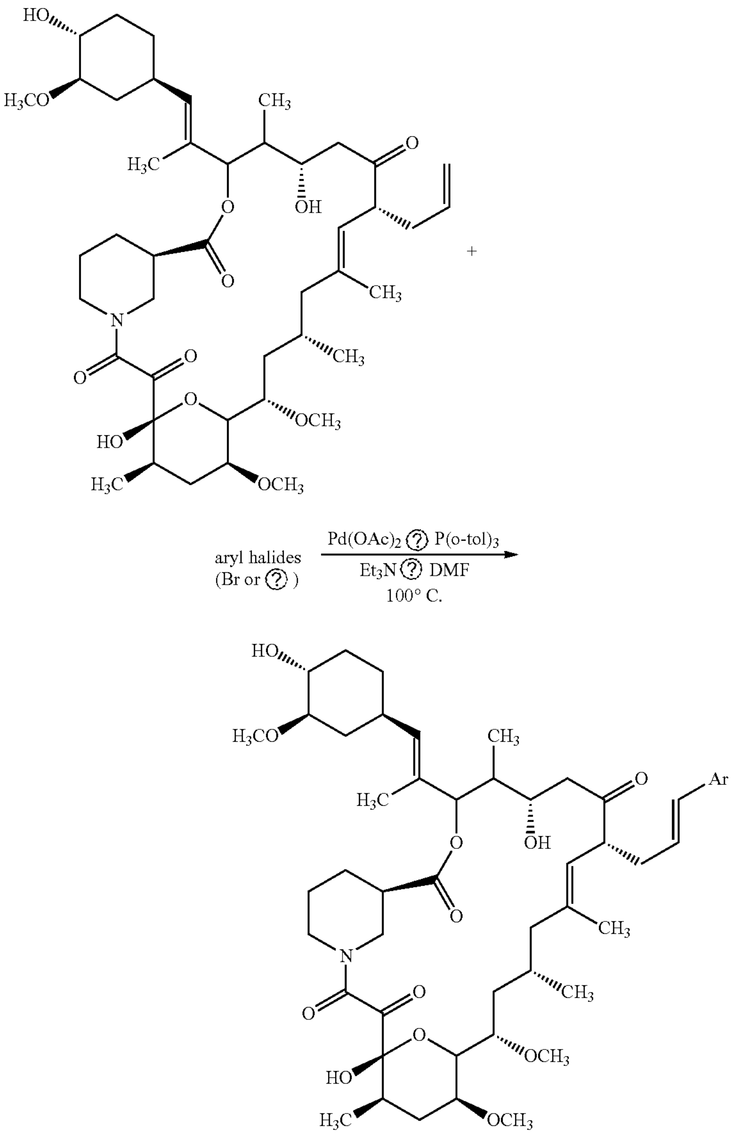
| Entry | Aryl Halide | Product (Ar ∞) | Time/h | Yield (%) |
|---|---|---|---|---|
| 1 | 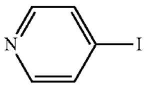 1a | 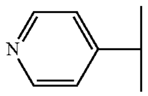 1b | 24 | 66 |
| 2 | 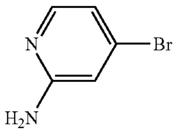 2a | 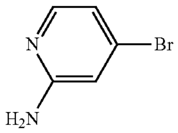 2b | 24 | 42 (52) |

TABLE 1-continued
| | | | | |
|---|---|---|---|---|
| 3 | 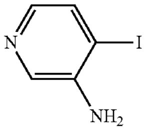 3a | 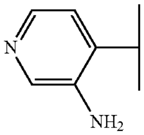 3b | 24 | 40 (54) |
| 4 | 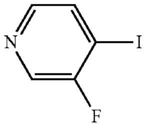 4a | 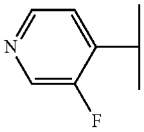 4b | 24 | 70 |
| 5 | 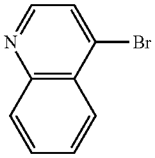 6a | 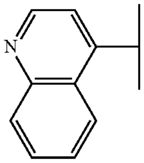 6b | 16 | 72 |
| 6 | 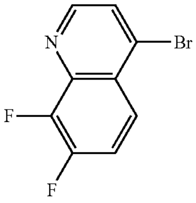 6a | 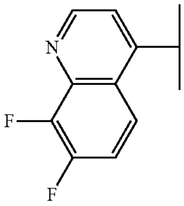 6b | 18 | 70 |
| 7 | 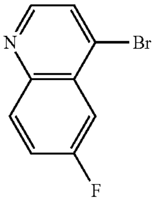 7a | 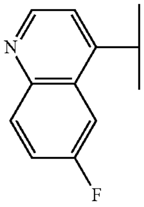 7b | 18 | 68 |
| 8 | 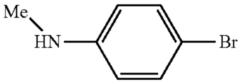 8a | 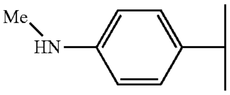 8b | 20 | 62 |
| 9 | 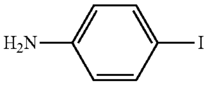 9a | 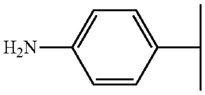 9b | 12 | 36 |
| 10 | 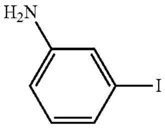 10a | 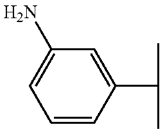 10b | 12 | 42 |

TABLE 1-continued

| | | | | |
|---|---|---|---|---|
| 11 | 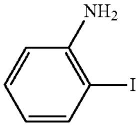 11a | 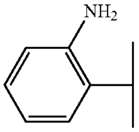 11b | 12 | 45 |

In accordance with an embodiment, the present invention provides a composition comprising a compound of formula I:

(I)

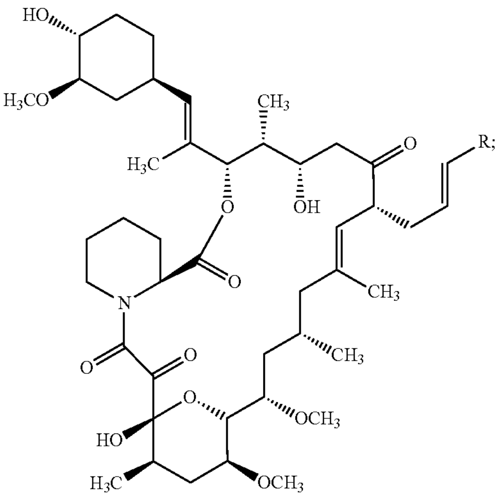

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur; and a pharmaceutically acceptable carrier.

In accordance with an embodiment, the present invention provides a composition comprising a compound of formula I, wherein R is selected from the group consisting of:

(1)

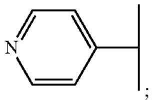

;

(2)

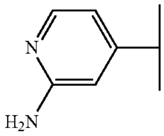

;

(3)

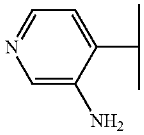

;

-continued (4)

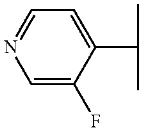

;

(5)

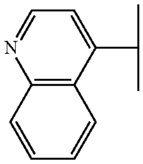

;

(6)

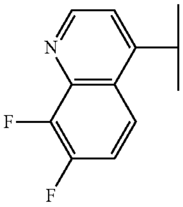

;

(7)

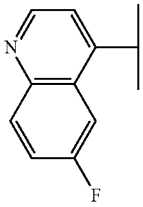

;

(8)

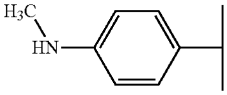

;

(9)

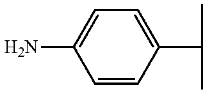

;

(10)

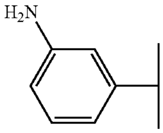

;

(11)

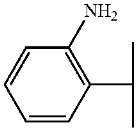

;

-continued (12)

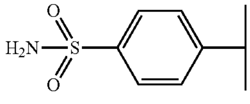

;

(13)

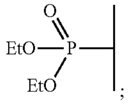

;

(14)

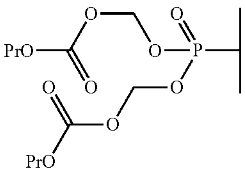

;

(15)

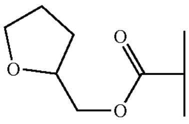

;

(16)

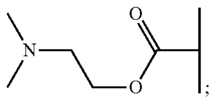

;

(17)

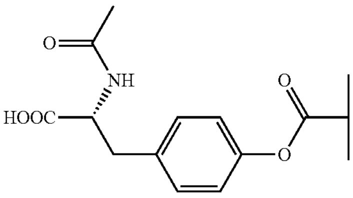

;

(18)

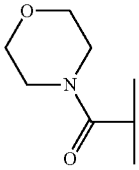

;

(19)

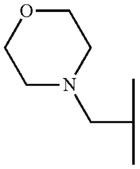

; and (20)

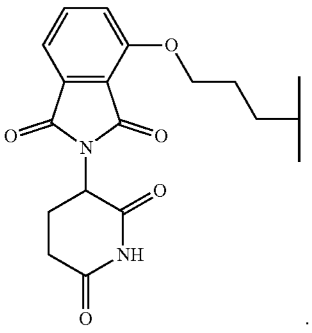

.

As used herein, the term "effective," means adequate to accomplish a desired, expected, or intended result. More particularly, an "effective amount" or a "therapeutically effective amount" is used interchangeably and refers to an amount of a stem cell mobilizer and/or an immunosuppressive agent, perhaps in further combination with yet another therapeutic agent, necessary to provide the desired "treatment" (defined herein) or therapeutic effect, e.g., an amount that is effective to prevent, alleviate, treat or ameliorate symptoms of a a tissue injury or wound. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration topically or in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the stem cell mobilizer and/or the compounds of formula I are administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a stem cell mobilizer and/or an compound of formula I together with a suitable amount of a pharmaceutically acceptable carrier so as to provide the form for proper administration to the patient. The formulation should suit the mode of administration. A preferred formulation is a subcutaneous formulation.

In accordance with an embodiment, the present invention provides a method for treating tissue injury in a subject comprising administering to the subject an effective amount of a compound of formula I:

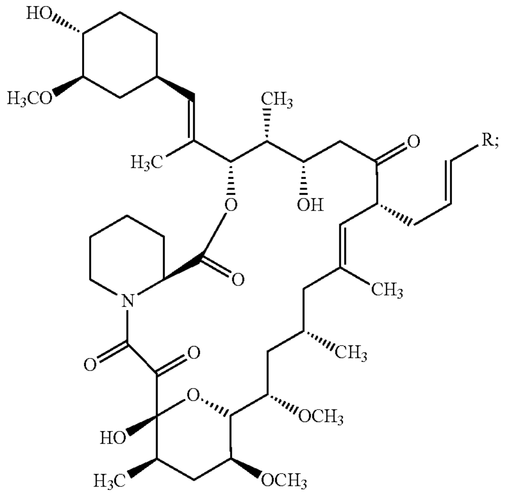
(I)

or a salt, solvate, or isomer, or derivative thereof, wherein R is a cycloalkyl, aryl, or heteroaryl group, substituted with H, halo, N, O, P, $C_1$-$C_6$ alkyl, imidazoyl, cycloalky, and heterocycloalkyl, wherein the heteroaryl and heterocycloalkyl groups comprise at least one heteroatom, preferably, 1 to 4 heteroatoms selected from nitrogen, oxygen, and sulfur.

In accordance with another embodiment, the present invention provides a method for treating tissue injury in a subject comprising administering to the subject a composition comprising an effective amount of a compound of formula I, and an effective amount of at least one stem cell mobilizer.

In accordance with a further embodiment, the present invention provides a method for treating tissue injury in a subject comprising administering to the subject a composition comprising an effective amount of a compound of formula I, and an effective amount of at least one stem cell mobilizer, and a pharmaceutically acceptable carrier.

In some embodiments, the present invention provides a method for treating tissue injury in a subject comprising administering to the subject a composition comprising an effective amount of a comprising a compound of formula I, wherein R is selected from the group consisting of:

(1)
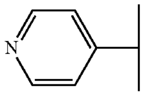
;

(2)
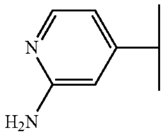
;

(3)
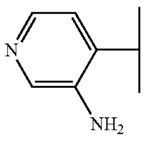
;

-continued (4)
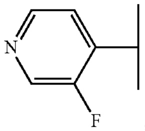
;

(5)
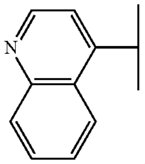
;

(6)
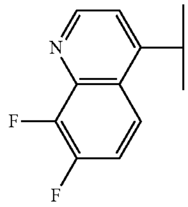
;

(7)
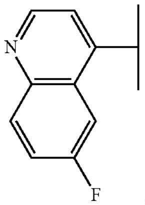
;

(8)
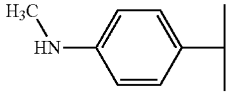
;

(9)
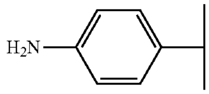
;

(10)
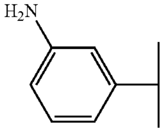
;

(11)
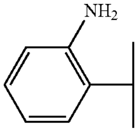
;

(12)
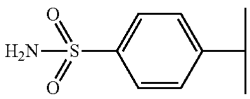
;

(13)
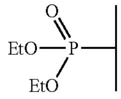
;

-continued (14)

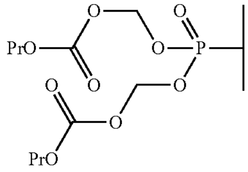

;

(15)

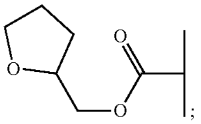

;

(16)

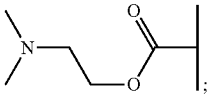

;

(17)

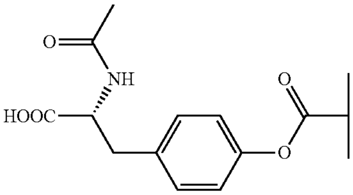

;

(18)

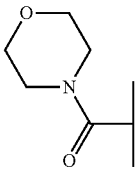

;

(19)

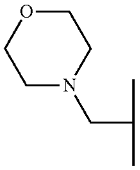

; and (20)

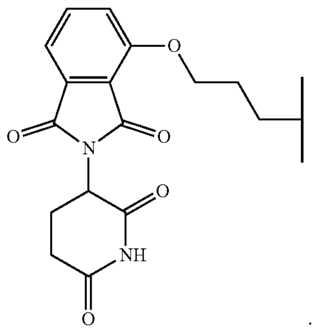

.

In accordance with a further embodiment, the present invention provides a method for treating tissue injury in a subject comprising administering to the subject a composition comprising an effective amount of a compound of formula I, an effective amount of at least one stem cell mobilizer, at least one additional biologically active agent, and a pharmaceutically acceptable carrier.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising a stem cell mobilizer and the compounds of formula I disclosed herein may be used alone (e.g., a formulation comprising a stem cell mobilizer and the compounds of formula I) or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising a stem cell mobilizer and/or compound of formula I in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

"Agent" refers to all materials that may be used as or in pharmaceutical compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "immunosuppressive agent" refers to an agent that inhibits, slows or reverses the activity of the immune system. Immunosuppressive agents act by suppressing the function of responding immune cells (including, for example, T cells), directly (e.g., by acting on the immune cell) or indirectly (by acting on other mediating cells).

The terms "stem cells" and "hematopoietic stem cells" are used interchangeably herein. Stem cells are distinguished from other cell types by two important characteristics. First, stem cells are unspecialized cells capable of renewing themselves through cell division, sometimes after long periods of inactivity. Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The term "stem cells" can refer to multipotent stem cells that are capable of differentiating into all blood cells including erythrocytes, leukocytes and platelets. For instance, the "hematopoietic stem cells" or "stem cells" as used in the invention are contained not only in bone marrow but also in umbilical cord blood derived cells.

A "patient," "subject," or "host," to be treated by the present methods refers to either a human or non-human animal, such as primates, mammals, and vertebrates.

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, the terms "treatment," "treating," "treat" and the like, refer to obtaining a desired pharmacologic and/or physiologic effect. The terms are also used in the context of the administration of a "therapeutically effective amount" of an agent, e.g., a stem cell mobilizer and/or an immunosuppressive agent. The effect may be prophylactic in terms of completely or partially preventing a particular outcome, disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In particular embodiments, the term is used in the context of promoting or improving wound healing in patients. In other embodiments, the term is used in the context of treating organ transplant recipient, wounds, burn victims, and autoimmune diseases including IBD.

As used herein, the term "tissue injury" which means acute or chronic wounds or ulcers of the skin or soft tissue. Examples of such wounds include diabetic sores and ulcers, burns, scalds, frostbite, punctures, abrasions, and the like.

In accordance with some embodiments, the compounds and pharmaceutical compositions described herein can be used in preparing a medicament for use in modulating the wound healing response in the skin of a mammal, comprising topical or subcutaneous application of the compositions in an effective amount for a sufficient period time. As used herein, the term "modulating the wound healing response" means the prevention or downregulation of the pathological response to tissue injury, which is characterized by fibrosis, including for example, production of keloids and hypertrophic scars in the skin, tendon adhesions, transmission blockage following nerve injury, scleroderma, Crohn's disease, esophageal strictures, urethral strictures, capsules around breast implants, liver cirrhosis, atherosclerosis and fibrotic non-union in bone. Chronic non-healing dermal ulcers are also examples of the pathological response to tissue injury and are alleviated by the compounds of formula I.

Stem Cell Mobilizers

A "stem cell mobilizer," "mobilizer of hematopoietic stem cells or progenitor cells" or "mobilize," (used interchangeably), as described herein, refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. A stem cell mobilizer may increase the number of hematopoietic stem cells or hematopoietic progenitor/precursor cells in the peripheral blood, thus allowing for a more accessible source of stem cells for use in treating organ transplant recipients, burn victims, IBD and/or promoting wound healing. In particular embodiments, a stem cell mobilizer refers to any agent that mobilizes CD34+ and/or CD133+ stem cells. In other embodiments, a stem cell mobilizer disrupts CXCL12 (SDF-1)-mediated chemoattraction of CXCR4-expressing cells.

The present invention provides pharmaceutical compositions comprising at least one stem cell mobilizer and at least one immunosuppressive drug. Generally, stem cell mobilizers include, but are not limited to, small organic molecules, polypeptides, nucleic acids, and carbohydrates.

In the case of a polypeptide, the stem cell mobilizer may comprise a cytokine, a colony stimulating factor, a protease or a chemokine. More specifically, the cytokine may include, but is not limited to, interleukin-1 (IL-1), interleukin-3 (IL-3), interleukin-6 (IL-6), interleukin- 11 (IL-11), interleukin-7 (IL-7), and interleukin-12 (IL12).

In the case of a colony stimulating factor, the stem cell mobilizer may include, but is not limited to, granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In another embodiment, the protease stem cell mobilizer may include, but is not limited to, metalloproteinase (like MMP2 or MMP9) a serine protease, (like cathepsin G, or elastase) a cysteine protease (like cathepsin K) and a dipeptidyl peptidase-1 (DDP-1 OR CD26).

In yet another embodiment, the chemokine stem cell mobilizer may include, but is not limited to, CXCL12, IL-8, Mip-1α, and GROβ.

In yet another embodiment, the nucleic acid stem cell mobilizer is a DNA or an RNA molecule. In more specific embodiments, the nucleic acid can be a small interfering RNA (siRNA) molecule or an antisense molecule specific for CXCL12.

In the case of a carbohydrate, the stem cell mobilizer can be a sulfated carbohydrate may include, but is not limited to, Fucoidan and sulfated dextran. Fucoidan is a carbohydrate consisting of L-fucose, sulfate and acetate in a molar proportion of 1:1.23:0.36 and can be isolated from the Pacific brown seaweed Fucus evanescens. See Bilan et al., 337(8) CARBOHYDRATE RESEARCH 719-30 (2002). Sulfated dextrans refer to a series of polysaccharides that have variable sulfated patterns. See, e.g. Pomin et al., 15(12) GLYCOBIOLOGY 1376-1385 (2005); *Melo* et al., 279(2) J. BIOL. CHEM. 20824-20835 (2004); and Farias et al., 275(38) J. BIOL. CHEM. 29299-29307 (2000).

Stem cell mobilizers may further include, but are not limited to, AMD3100; stromal cell-derived factor (SDF-1); SDF-1 analogs (e.g., CTCE-0214 (Chemokine Therapeutics Corp.)); anti-SDF-1 antibodies; cyclophosphamide; stem cell factor (SCF); filgrastim; ancestim; Myeloid Progenitor Inhibitory Factor-1 (MPIF-1) (see U.S. Patent Publication No. 20080274109); and Very Late Antigen (VLA-4) antagonists (e.g., an alpha-4 integrin antagonist, such as an antibody including Natalizumab or Anti-phospho-Integrin a4 (Ser988), clone 6.33 (Upstate Cell Signaling Solutions), or a peptide (e.g., phenylacetyl-leu-asp-phe-D-prolineamide (Cytel Corp., San Diego Calif.))).

In particular embodiments, the stem cell mobilizer comprises a CXCR4 antagonist. In specific embodiments, the CXCR4 antagonist is TG-0054 (Burixafor; Phosphonic acid, p-(2-(4-(6-amino-2-(((trans-4-(((3-(cyclohexylamino)propyl)amino)methyl)cyclohexyl)methyl) amino)-4-pyrimidinyl)-1-piperazinyl)ethyl)-) (TaiGen Biotechnology Co., Ltd. (Taipei, Taiwan)). In other specific embodiments, the CXCR4 antagonist is AMD3465 (N-(pyridin-2-ylmethyl)-1-[4-(1,4,8,11-tetrazacyclotetradec-1-ylmethyl)phenyl] methanamine). In yet other embodiments, the CXCR4 antagonist is AMD3100. AMD3100 (1,1'-[1,4-phenylenebis (methylene)]bis-1,4,8,11-tetraazacyclo-tetradecane) is a symmetric bicyclam, prototype non-peptide antagonist of the CXCR4 chemokine receptor. See U.S. Pat. Nos. 6,835,731 and 6,825,351. The term "AMD" or "AMD3100" is used interchangeably with Plerixafor, rINN, USAN, JM3100, and its trade name, Mozobil™. For convenience, the term "Plerixafor" is used throughout to refer to a CXCR4 antagonist.

The present invention also contemplates using mimetics of AMD3100. Mutational substitutions at 16 positions located in TM-III, -IV, -V, -VI, and -VII lining the main ligand-binding pocket of the CXCR4 receptor have identified three acid residues: $Asp^{171}$ (AspIV:20), $Asp^{262}$ (AspVI:23), and $Glu^{288}$ (GluVII:06) as the main interaction points for AMD3100. Molecular modeling suggests that one cyclam ring of AMD3100 interacts with $Asp^{171}$ in TM-IV, whereas the other ring is sandwiched between the carboxylic acid groups of $Asp^{262}$ and $Glu^{288}$ from TM-VI and —VII, respectively. In one study, it was found that introduction of only a Glu at position VII:06 and the removal of a neutralizing Lys residue at position VII:02 resulted in a 1000-fold increase in affinity of AMD3100 to within 10-fold of its affinity in CXCR4. Thus, mimetics, such as for example, peptide or non-peptide antagonists with improved oral bioavailability can be designed to efficiently and selectively block the CXCR4 receptor.

In other embodiments, the stem cell mobilizer is BKT140 (Biokin Therapeutics, Ltd. (Rehovot, Israel). BKT140 (4F-benzoyl-TN14003) binds and inhibits the CXCR4 chomokin receptor with high affinity, showing an $IC_{50}$ of ~1 nmol/L compared with the values obtained with AMD3100. Moreover, BKT140 hinders the cell migration stimulated by CXCL12 within $IC_{50}$ values of 0.5 to 2.5 nmol/L compared with $IC_{50}$ value of 51±17 nmol/L for Plerixafor, suggesting ahigh mobilization capacity. See Peled et al., 20 CLIN. CANCER RES. 469-79 (2013).

FK Binding Protein Ligands

In conjunction with at least one stem cell mobilizer, the pharmaceutical compositions comprise non-immunosuppressive FK binding protein ligand(s). In addition to the compounds of formula I disclosed herein, other examples of non-immunosuppressive ligands include meridamycin, antascomicins, and synthetic ligand of FKBP (SLF).

A normal dose of the compounds of formula I is about 0.1 mg/kg/day-0.3 mg/kg/day (oral) and about 0.01 mg/kg/day-0.05 mg/kg/day (IV). In certain embodiments, a low dose of Tacrolimus is about one tenth the normal dose, e.g., about 0.01 mg/kg/day-0.03 mg/kg/day (oral) and about 0.001 mg/kg/day-0.005 mg/kg/day (IV).

In certain embodiments, the stem cell mobilizer is AMD3100. In such embodiments, the pharmaceutical composition can comprise a typical dose for AMD3100. This drug is typically administered to human patients at about 0.12-0.24 mg/kg. In a patient who has 60 kg body weight, the dosage of ADM3100 is about 0.24 mg/kg/day by subcutaneous injection.

The pharmaceutical compositions can be described in terms of a ratio of (a) a compound of formula I or a non-immunosuppressive FKBP ligand to (b) a stem cell mobilizer (e.g., a CXCR antagonist). In certain embodiments, the ratio can be 1/1, 1/2, 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, or more.

The pharmaceutical compositions can comprise (a) a compound of formula I or a non-immunosuppressive FKBP ligand and (b) a stem cell mobilizer in a ratio range of about 1/10-1/100, 1/10-1/99, 1/10-1/98, 1/10-1/97, 1/10-1/96, 1/10-1/95, 1/10-1/94, 1/10-1/93, 1/10-1/92, 1/10-1/91, 1/10-1/90, 1/10-1/89, 1/10-1/88, 1/10-1/87, 1/10-1/86, 1/10-1/85, 1/10-1/84, 1/10-1/83, 1/10-1/82, 1/10-1/81, 1/10-1/80, 1/10-1/79, 1/10-1/78, 1/10-1/77, 1/10-1/76, 1/10-1/75, 1/10-1/74, 1/10-1/73, 1/10-1/72, 1/10-1/71, 1/10-1/70, 1/10-1/69, 1/10-1/68, 1/10-1/67, 1/10-1/66, 1/10-1/65, 1/10-1/64, 1/10-1/63, 1/10-1/62, 1/10-1/61, 1/10-1/60, 1/10-1/59, 1/10-1/58, 1/10-1/57, 1/10-1/56, 1/10-1/55, 1/10-1/54, 1/10-1/53, 1/10-1/52, 1/10-1/51, 1/10-1/50, 1/10-1/49, 1/10-1/48, 1/10-1/47, 1/10-1/46, 1/10-1/45, 1/10-1/44, 1/10-1/43, 1/10-1/42, 1/10-1/41, 1/10-1/40, 1/10-1/39, 1/10-1/38, 1/10-1/37, 1/10-1/36, 1/10-1/35, 1/10-1/34, 1/10-1/33, 1/10-1/32, 1/10-1/31, 1/10-1/30, 1/10-1/29, 1/10-1/28, 1/10-1/27, 1/10-1/26, 1/10-1/25, 1/10-1/24, 1/10-1/23, 1/10-1/22, 1/10-1/21, 1/10-1/20, 1/10-1/19, 1/10-1/18, 1/10-1/17, 1/10-1/16, 1/10-1/15, 1/10-1/14, 1/10-1/13, 1/10-1/12, or 1/10-1/11.

In alternative embodiments, the pharmaceutical compositions can comprise (a) a compound of formula I or a non-immunosuppressive FKBP ligand and (b) a stem cell mobilizer in a ratio range of about 1/15-1/100, 1/15-1/99, 1/15-1/98, 1/15-1/97, 1/15-1/96, 1/15-1/95, 1/15-1/94, 1/15-1/93, 1/15-1/92, 1/15-1/91, 1/15-1/90, 1/15-1/89, 1/15-1/88, 1/15-1/87, 1/15-1/86, 1/15-1/85, 1/15-1/84, 1/15-1/83, 1/15-1/82, 1/15-1/81, 1/15-1/80, 1/15-1/79, 1/15-1/78, 1/15-1/77, 1/15-1/76, 1/15-1/75, 1/15-1/74, 1/15-1/73, 1/15-1/72, 1/15-1/71, 1/15-1/70, 1/15-1/69, 1/15-1/68, 1/15-1/67, 1/15-1/66, 1/15-1/65, 1/15-1/64, 1/15-1/63, 1/15-1/62, 1/15-1/61, 1/15-1/60, 1/15-1/59, 1/15-1/58, 1/15-1/57, 1/15-1/56, 1/15-1/55, 1/15-1/54, 1/15-1/53, 1/15-1/52, 1/15-1/51, 1/15-1/50, 1/15-1/49, 1/15-1/48, 1/15-1/47, 1/15-1/46, 1/15-1/45, 1/15-1/44, 1/15-1/43, 1/15-1/42, 1/15-1/41, 1/15-1/40, 1/15-1/39, 1/15-1/38, 1/15-1/37, 1/15-1/36, 1/15-1/35, 1/15-1/34, 1/15-1/33, 1/15-1/32, 1/15-1/31, 1/15-1/30, 1/15-1/29, 1/15-1/28, 1/15-1/27, 1/15-1/26, 1/15-1/25, 1/15-1/24, 1/15-1/23, 1/15-1/22, 1/15-1/21, 1/15-1/20, 1/15-1/19, 1/15-1/18, 1/15-1/17, or 1/15-1/16.

The ratio range of (a) a compound of formula I or a non-immunosuppressive FKBP ligand to (b) a stem cell mobilizer within a pharmaceutical composition can comprise about 1/20-1/100, 1/20-1/99, 1/20-1/98, 1/20-1/97, 1/20-1/96, 1/20-1/95, 1/20-1/94, 1/20-1/93, 1/20-1/92, 1/20-1/91, 1/20-1/90, 1/20-1/89, 1/20-1/88, 1/20-1/87, 1/20-1/86, 1/20-1/85, 1/20-1/84, 1/20-1/83, 1/20-1/82, 1/20-1/81, 1/20-1/80, 1/20-1/79, 1/20-1/78, 1/20-1/77, 1/20-1/76, 1/20-1/75, 1/20-1/74, 1/20-1/73, 1/20-1/72, 1/20-1/71, 1/20-1/70, 1/20-1/69, 1/20-1/68, 1/20-1/67, 1/20-1/66, 1/20-1/65, 1/20-1/64, 1/20-1/63, 1/20-1/62, 1/20-1/61, 1/20-1/60, 1/20-1/59, 1/20-1/58, 1/20-1/57, 1/20-1/56, 1/20-1/55, 1/20-1/54, 1/20-1/53, 1/20-1/52, 1/20-1/51, 1/20-1/50, 1/20-1/49, 1/20-1/48, 1/20-1/47, 1/20-1/46, 1/20-1/45, 1/20-1/44, 1/20-1/43, 1/20-1/42, 1/20-1/41, 1/20-1/40, 1/20-1/39, 1/20-1/38, 1/20-1/37, 1/20-1/36, 1/20-1/35, 1/20-1/34, 1/20-1/33, 1/20-1/32, 1/20-1/31, 1/20-1/30, 1/20-1/29, 1/20-1/28, 1/20-1/27, 1/20-1/26, 1/20-1/25, 1/20-1/24, 1/20-1/23, 1/20-1/22, or 1/20-1/21.

In other embodiments, the ratio range of (a) a compound of formula I or a non-immunosuppressive FKBP ligand to (b) a stem cell mobilizer within a pharmaceutical composition can comprise about 1/30-1/100, 1/30-1/99, 1/30-1/98, 1/30-1/97, 1/30-1/96, 1/30-1/95, 1/30-1/94, 1/30-1/93, 1/30-1/92, 1/30-1/91, 1/30-1/90, 1/30-1/89, 1/30-1/88, 1/30-1/87, 1/30-1/86, 1/30-1/85, 1/30-1/84, 1/30-1/83, 1/30-1/82, 1/30-1/81, 1/30-1/80, 1/30-1/79, 1/30-1/78, 1/30-1/77, 1/30-1/76, 1/30-1/75, 1/30-1/74, 1/30-1/73, 1/30-1/72, 1/30-1/71, 1/30-1/70, 1/30-1/69, 1/30-1/68, 1/30-1/67, 1/30-1/66, 1/30-1/65, 1/30-1/64, 1/30-1/63, 1/30-1/62, 1/30-1/61, 1/30-1/60, 1/30-1/59, 1/30-1/58, 1/30-1/57, 1/30-1/56, 1/30-1/55, 1/30-1/54, 1/30-1/53, 1/30-1/52, 1/30-1/51, 1/30-1/50, 1/30-1/49, 1/30-1/48, 1/30-1/47, 1/30-1/46, 1/30-1/45, 1/30-1/44, 1/30-1/43, 1/30-1/42, 1/30-1/41, 1/30-1/40, 1/30-1/39, 1/30-1/38, 1/30-1/37, 1/30-1/36, 1/30-1/35, 1/30-1/34, 1/30-1/33, 1/30-1/32, or 1/30-1/31.

In further embodiments, the pharmaceutical compositions can comprise (a) a compound of formula I or a non-immunosuppressive FKBP ligand and (b) a stem cell mobilizer in a ratio range of about 1/40-1/100, 1/40-1/99, 1/40-1/98, 1/40-1/97, 1/40-1/96, 1/40-1/95, 1/40-1/94, 1/40-1/93, 1/40-1/92, 1/40-1/91, 1/40-1/90, 1/40-1/89, 1/40-1/88, 1/40-1/87, 1/40-1/86, 1/40-1/85, 1/40-1/84, 1/40-1/83, 1/40-1/82, 1/40-1/81, 1/40-1/80, 1/40-1/79, 1/40-1/78, 1/40-1/77, 1/40-1/76, 1/40-1/75, 1/40-1/74, 1/40-1/73, 1/40-1/72, 1/40-1/71, 1/40-1/70, 1/40-1/69, 1/40-1/68, 1/40-1/67, 1/40-1/66, 1/40-1/65, 1/40-1/64, 1/40-1/63, 1/40-1/62, 1/40-1/61, 1/40-1/60, 1/40-1/59, 1/40-1/58, 1/40-1/57, 1/40-1/56, 1/40-1/55, 1/40-1/54, 1/40-1/53, 1/40-1/52, 1/40-1/51, 1/40-1/50, 1/40-1/49, 1/40-1/48, 1/40-1/47, 1/40-1/46, 1/40-1/45, 1/40-1/44, 1/40-1/43, 1/40-1/42, or 1/40-1/41.

In alternative embodiments, the pharmaceutical compositions can comprise (a) a compound of formula I or a non-immunosuppressive FKBP ligand and a stem cell mobilizer in a ratio range of about 1/50-1/100, 1/50-1/99, 1/50-1/98, 1/50-1/97, 1/50-1/96, 1/50-1/95, 1/50-1/94, 1/50-1/93, 1/50-1/92, 1/50-1/91, 1/50-1/90, 1/50-1/89, 1/50-1/88, 1/50-1/87, 1/50-1/86, 1/50-1/85, 1/50-1/84, 1/50-1/83, 1/50-1/82, 1/50-1/81, 1/50-1/80, 1/50-1/79, 1/50-1/78, 1/50-1/77, 1/50-1/76, 1/50-1/75, 1/50-1/74, 1/50-1/73, 1/50-1/72, 1/50-1/71, 1/50-1/70, 1/50-1/69, 1/50-1/68, 1/50-1/67, 1/50-1/66, 1/50-1/65, 1/50-1/64, 1/50-1/63, 1/50-1/62, 1/50-1/61, 1/50-1/60, 1/50-1/59, 1/50-1/58, 1/50-1/57, 1/50-1/56, 1/50-1/55, 1/50-1/54, 1/50-1/53, 1/50-1/52, 1/50-1/51, 1/60-1/100, 1/60-1/99, 1/60-1/98, 1/60-1/97, 1/60-1/96, 1/60-1/95, 1/60-1/94, 1/60-1/93, 1/60-1/92, 1/60-1/91, 1/60-1/90, 1/60-1/89, 1/60-1/88, 1/60-1/87, 1/60-1/86, 1/60-1/85, 1/60-1/84, 1/60-1/83, 1/60-1/82, 1/60-1/81, 1/60-1/80, 1/60-1/79, 1/60-1/78, 1/60-1/77, 1/60-1/76, 1/60-1/75, 1/60-1/74, 1/60-1/73, 1/60-1/72, 1/60-1/71, 1/60-1/70, 1/60-1/69, 1/60-1/68, 1/60-1/67, 1/60-1/66, 1/60-1/65, 1/60-1/64, 1/60-1/63, 1/60-1/62, 1/60-1/61.

In other embodiments, the ratio range of (a) a compound of formula I or a non-immunosuppressive FKBP ligand to (b) a stem cell mobilizer within a pharmaceutical composition can comprise about 1/70-1/100, 1/70-1/99, 1/70-1/98, 1/70-1/97, 1/70-1/96, 1/70-1/95, 1/70-1/94, 1/70-1/93, 1/70-1/92, 1/70-1/91, 1/70-1/90, 1/70-1/89, 1/70-1/88, 1/70-1/87, 1/70-1/86, 1/70-1/85, 1/70-1/84, 1/70-1/83, 1/70-1/82, 1/70-1/81, 1/70-1/80, 1/70-1/79, 1/70-1/78, 1/70-1/77, 1/70-1/76, 1/70-1/75, 1/70-1/74, 1/70-1/73, 1/70-1/72, 1/70-1/71, 1/80-1/100, 1/80-1/99, 1/80-1/98, 1/80-1/97, 1/80-1/96, 1/80-1/95, 1/80-1/94, 1/80-1/93, 1/80-1/92, 1/80-1/91, 1/80-1/90, 1/80-1/89, 1/80-1/88, 1/80-1/87, 1/80-1/86, 1/80-1/85, 1/80-1/84, 1/80-1/83, 1/80-1/82, 1/80-1/81, 1/90-1/100, 1/90-1/99, 1/90-1/98, 1/90-1/97, 1/90-1/96, 1/90-1/95, 1/90-1/94, 1/90-1/93, 1/90-1/92, or 1/90-1/91.

In particular embodiments, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

In other embodiments, the pharmaceutical compositions may be administered every other day for about 2 days, every other day for about 3 days, every other day for about 4 days, every other day for about 5 days, every other day for about 6 days, every other day for about 7 days, every other day for about 8 days, every other day for about 9 days, every other day for about 10 days, every other day for about 11 days, every other day for about 12 days, every other day for about 13 days, every other day for about 14 days, every other day for about 15 days, every other day for about 16 days, every other day for about 17 days, every other day for about 18 days, every other day for about 19 days, every other day for about 20 days, every other day for about 21 days, every other day for about 22 days, every other day for about 23 days, every other day for about 24 days, every other day for about 25 days, every other day for about 26 days, every other day for about 27 days, every other day for about 28 days, every other day for about 29 days, every other day for about 30 days, or every other day for about 31 days or more.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days. In certain embodiments, the pharmaceutical composition is administered every other day.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

In particular embodiments, the present invention relates to use of FDA approved drugs—such as stem cell mobilizing agent AMD3100 and the compounds of formula I, either sequentially, or in the form of combination for the treatment of a variety of tissue injuries (wounds), organ transplantation, and inflammatory or autoimmune disorders such as inflammatory bowel diseases (IBD). Thus, pharmaceutical compositions comprising a combination of a stem cell mobilizing agent AMD3100 with an immunosuppressant FK506 is useful for the treatment of a variety of disorders.

AMD3100. AMD3100 (Plerixafor or Mozobil) is a CXCR4 antagonist, originally developed as an anti-HIV medicine but found to potently mobilize CD34 and other stem cells from their bone marrow niche. AMD3100 was first approved by the FDA in 2008 for use in multiple myeloma cancer patients for banking of stem cells prior to myeloablative chemotherapy. Today, Plerixafor is used, often with neupogen (G-CSF), to mobilize hematopoietic stem cells in multiple myeloma cancer patients for banking prior to myeloablative chemotherapy. Mobilized stem cells are subsequently transplanted back to the patient after cancer treatment. Thus the drug is well established to be safe and effective.

FK506. FK506 (Tacrolimus or Prograph) was discovered in 1987 from a type of soil bacterium, *Streptomyces* tsukubaensis. FK506 reduces peptidyl-prolyl isomerase activity by binding to the immunophilin FKBP12 (FK506 binding protein) creating a new complex. FK506 was first approved by the FDA in 1994 for use in liver transplantation; this has been extended to include kidney, heart, small bowel, pancreas, lung, trachea, skin, and cornea, bone marrow, and limb transplants. The compounds of formula I reduce peptidyl-prolyl isomerase activity by binding to the immunophilin FKBP12 as well but do not have the immunosuppressive action of FK506.

The pharmaceutical compositions described herein provide a potent, synergistic activity of AMD3100 and the compounds of formula I in mobilizing, recruiting and retaining of stem cells in the injured sites. The combination treatment induces organ transplant acceptance, accelerates wound healing and promote intestinal mucosal regeneration in inflammatory bowel diseases. In certain embodiments, the ratio of the compounds of formula I to AMD3100 is about 1/10 to 1/100 in the composition. In particular embodiments, a pharmaceutical composition comprises only two active ingredients wherein the first active ingredient is AMD3100 and the second active ingredient is a compound of formula I, wherein the composition comprises 10-40 mg of AMD3100 and 0.1 to 4 mg of the compound of formula I, wherein said compound enhances the potency of said AMD3100 and wherein the pharmaceutical composition further comprises an excipient. The composition is formulated for subcutaneously or intravenously injection, or perhaps is formulated for oral administration or topical administration.

Dosages of the AMD3100 and the compounds of formula I may be determined individually. In prior art therapeutic regimens, the AMD3100 is typically administered to human patients at about 0.12-0.24 mg/kg/day. The compounds of formula I are typically administered intravenously at about 0.01-0.05 mg/kg/day or orally 0.1-0.2 mg/kg/day to prevent immune mediated rejection after organ transplantation. The dosage of the compounds of formula I are adjusted according to clinical response and observed FK506 whole blood trough concentrations (6-20 ng/ml). In animals (rodents), AMD3100 is typically administered at about 1 mg/kg/day to effectively mobilize bone marrow stem cells. The the compounds of formula I are typically administered to rodents at about 0.5-3 mg/kg/day to prevent immune mediated rejection after organ transplantation. In the methods and compositions of the present invention, the compounds of formula I typically will be used in lower dosages (e.g., blood trough concentration about 0.5-4 ng/ml) than those given above. Thus, the AMD3100 can be used at a dosage of 0.12 to 0.24 mg/kg/day in humans (1 mg/kg/day in animals), and the compounds of formula I can be used at a dosage of 0.001-0.005 mg/kg (subcutaneously).

In one embodiment, the compositions of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially the entire compound is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Chemical Synthesis of the Compounds of Formula I.

The inventors synthesized a first novel non-immunosuppressive FK506 analog, named FKVP that retained FKBP binding and lacked calcineurin inhibition activity (FIG. 1). FKVP was found to activate Bone Morphogenic Protein (BMP) signalling in lymphocytes and endothelial cells through disruption of FKBP12-BMPR1 interaction. Moreover, the combination of FKVP and AMD3100 was found to accelerate wound healing in diabetic rats in a BMP receptor-dependent manner.

FKVP Synthesis and Formulation for Animal Studies

Figure 20:
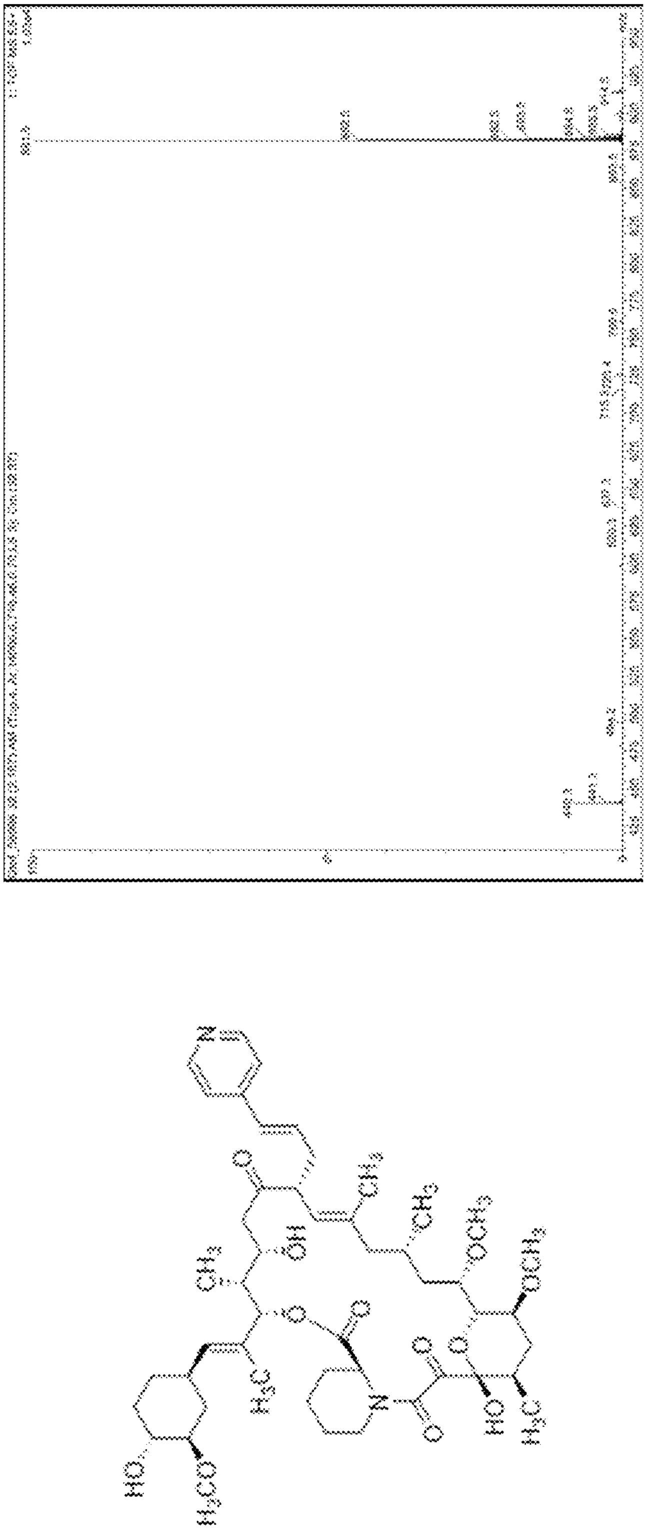
FIG. 20 is the structure of FKVP and the Mass Spectra of the compound $[C_{49}H_{72}N_2O_{12}+H]881.5$ (HRMS-ESI (m/z): calc'd for $C_{49}H_{72}N_2O_{12}$ [FKVP+H]+881.5164, found 881.5135).
Figure 21B:
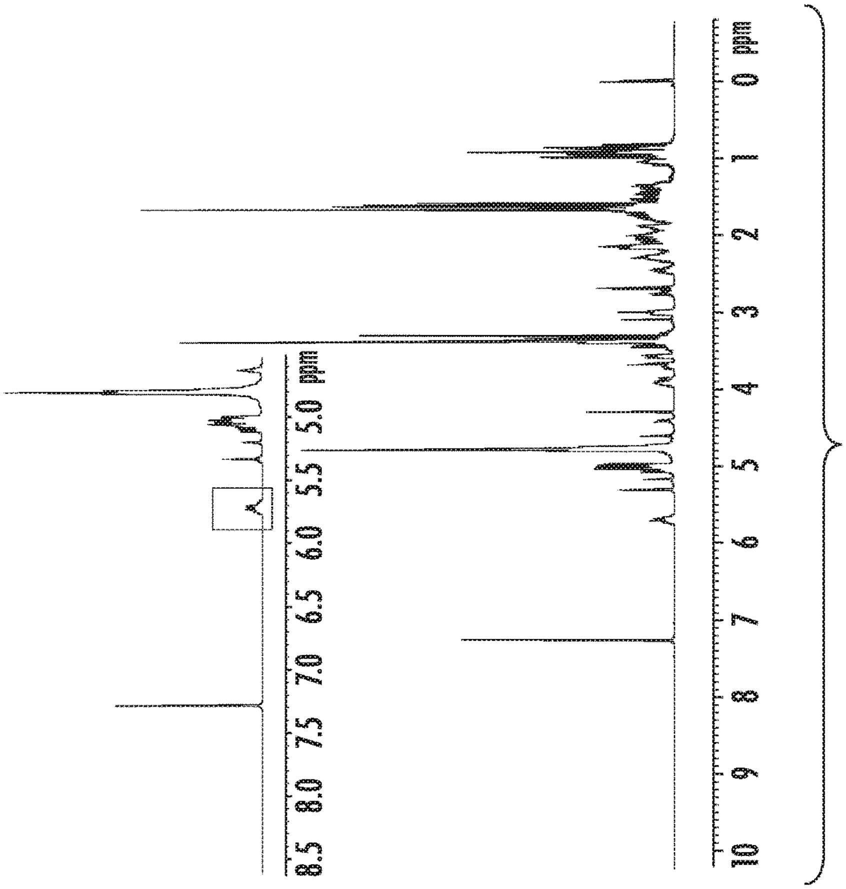
FIGS. 21A-21B depict NMR spectra for FKVP structure characterization. $^1$H-NMR spectra of (FIG. 21A) FKVP and (FIG. 21B) FK506 ($CDCL_3$), including detail of 5.5 ppm-6.0 ppm showing disappearance of terminal alkene in FKVP (present in FK506, highlighted in yellow).
Figure 21A:
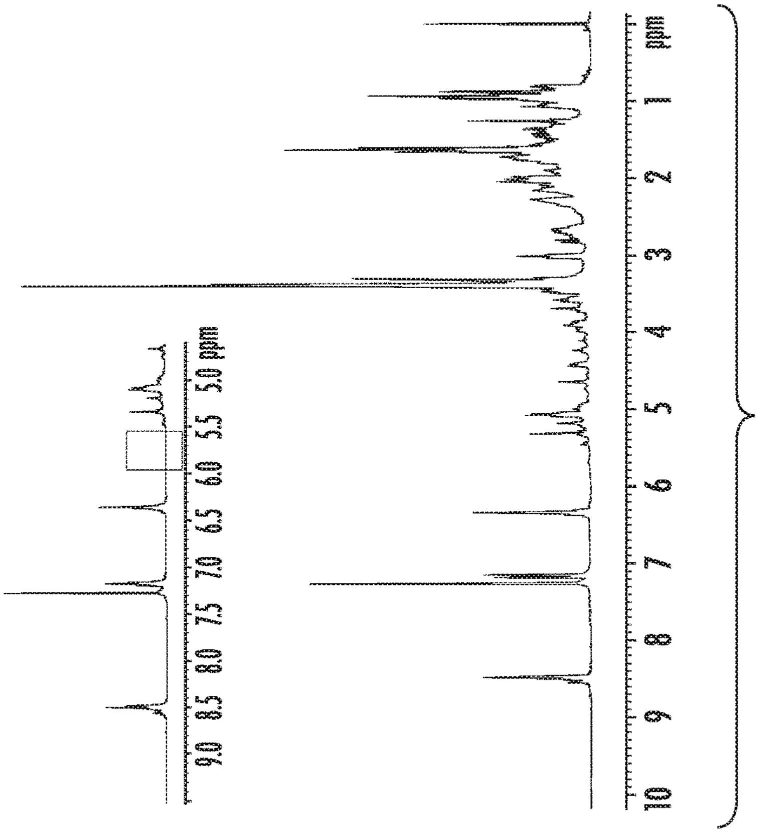

To a solution of FK506 (100 mg, 0.120 mmol) and 40 mol % Zhan1b catalyst $RuCl_2[C_{21}H_{26}N_2][C_{12}H_{17}NO_3S]$, in 3 mL anhydrous DCE was added 4-vinylpyridine (14.2 μL, 0.132 mmol). The mixture was stirred for 30 sec before microwave irradiation at 120° C. for 20 mins. The mixture was then purified using flash chromatography (0-25% MeOH in DCM), preparative-TLC (9:1 DCM:MeOH), and reverse-phase HPLC (45-85% ACN in $H_2O$). Conversion=25%, Purified Yield=8%. LC-MS and $^1$H-NMR experiments were used to confirm the new compound was >99% free of the parent compound (FK506). Product was characterized using Hi-Resolution MS (FIG. 20) and $^1H$-NMR (FIGS. 21A-B), then dissolved into DMSO or used in formulation for animal experiments.

For animal experiments, FKVP powder was dissolved into 80% EtOH/20% Cremophor RH60 solution at 5 mg/mL. This stock was diluted 1:50 into saline before subcutaneous injection.

subtraction (media only+dye), absorbance values were left as arbitrary absorbance units or normalized to those obtained from cells treated with DMSO.

Western Blot

Jurkat T cells were collected by centrifugation (300 g, 5 min), washed with PBS, and lysed in RIPA buffer containing

TABLE 2

Antibody information

| Target | Conjugation | Recommended Concentration | Manufacturer | Catalog # | Antibody Usage |
|---|---|---|---|---|---|
| p-SMAD1/5 | None | 1:750 | Cell Signaling | 41D10 | WB Primary |
| SMAD1 | None | 1:500 | Cell Signaling | 9473S | WB Primary |
| P-SMAD2/3 | None | 1:400 | Cell Signaling | 8828S | WB Primary |
| NFATc2 | None | 1:100 | Santa Cruz | SC-7296 | WB Primary |
| p-S6 | None | 1:1000 | Santa Cruz | SC-293144 | WB Primary |
| S6 | None | 1:1000 | Cell Signaling | 2217 | WB Primary |
| ID1 | HRP | 1:100 or 1:500 w/secondary | Santa Cruz | SC-133104-HRP | WB Primary |
| FKBP12 | None | 1:750 | Abcam | 92459 | WB Primary |
| FKBP51 | None | 1:750 | Abcam | Ab126715 | WB Primary |
| FKBP52 | None | 1:750 | Santa Cruz | SC-1803 | WB Primary |
| mTOR | None | 1:1000 | Cell Signaling | 2983S | WB Primary |
| Pan Calcineurin | None | 1:1000 | Cell Signaling | 2614S | WB Primary |
| HA-Tag | None | 1:1000 | Cell Signaling | 3724S | WB Primary |
| V5-Tag | None | 1:1000 | Thermo | 46-0705 | WB Primary |
| HSP90α/β | None | 1:1000 | Santa Cruz | SC-13119 | Loading Control (WB Primary) |
| GAPDH | None | 1:2000 | Santa Cruz | SC-20357 | Loading Control (WB Primary) |
| HSP90α/β | None | 1:1000 | Santa Cruz | SC-7947 | Loading Control (WB Primary) |
| Rabbit 2° Ab | HRP | 1:10000 | Cell Signaling | 7074S | WB Secondary |
| Rabbit 2° Ab | Alexa 647 | 1:1000 | Thermo | A-31573 | WB Secondary |
| Mouse 2° Ab | HRP | 1:8000 | GE Healthcare | NA931V | WB Secondary |
| Goat 2° Ab | HRP | 1:10000 | Santa Cruz | SC-2354 | WB Secondary |
| CD133 | None | 1:300 | Abcam | Ab19898 | IHC Primary |
| Rabbit 2° Ab | Biotin | 1:200 | Cell Signaling | 147085 | IHC Secondary |

Chemicals: Research-grade FK1506 (>98%) was purchased from APE×BIO. LDN-193189 hydrochloride, 4-vinylpyridine, and solvents were purchased form MilliporeSigma. Zhan-1b Ruthenium catalyst (CAS: 918870-76-5) was purchased from STREM Chemicals.

Cell Culture and Transfections

Jurkat (E6.1, ATCC) cells were cultured in RPMI with 10% FBS and 1.5% PennStrep. Jurkat cells ($1\times10^6$) were transfected with 10 μg of BRE-Luciferase (kindly provided by Martine Roussel & Peter ten Dijke) or NFAT-Luciferase cDNA (Promega) by electroporation (BioRad, square-wave, 250V, 950 pF) in 400 μL serum/antibiotic free RPMI with 0.5% DMSO. Thirty minutes after transfection, cells were transferred to complete RPMI and rested overnight. Before plating, cells were re-suspended in fresh media and diluted to $0.5\times10^6$ cells/mL. HEK293T cells were cultured in DMEM with 10% FBS, 1% PennStrep, and 500 μg/mL G418 (Corning). Cells were transfected using SuperFect reagent and supplied transfection protocols. HUVEC cells were cultured in Lonza Endothelial Cell Growth Medium (EGM-2) and used between passages 3 and 7. All cells were cultured at 37° C. with 5% $CO_2$.

Cell Viability Assays

Jurkat or HUVEC cells were plated at 1000 cells/well in 180 μL growth media before addition of 20 μL of 10X drug/protein stock. After incubation for 72 h, 22 μL of a resazurin sodium salt solution (0.1 mg/mL stock in water) was added to each well and allowed to incubate at 37° C. The metabolic conversion of resazurin dye was monitored by absorbance at 570 nm after 6 h. After background protease and phosphatase inhibitors (Cell Signaling) with sonication. Lysates were normalized using DC assay (Bio-Rad) and run on SDS-PAGE gels. Proteins were transferred to nitrocellulose membranes overnight at 100 mA. After blocking with 5% milk in TBS-T for 20 min, membranes were incubated overnight at 4° C. with primary antibodies (Table 2). After washing three times with TBS-T, membranes were incubated with secondary antibody (Table 2) for 1 hour. After 3 additional washes, blots were visualized using SynGene, either using ECL substrate (Thermo) or laser excitation and filter (647 nm).

FKBP12-SNAP Pull-Downs

FKBP12-SNAP was cloned using pSNAPf vector (New England Bio) and PCR-amplified FKBP12 (a gift from Tobias Meyer, Addgene plasmid #20175) with added EcoRI and BsrGI restriction sites. Gel-purified plasmids were ligated using T4 DNA ligase (Thermo), transformed into DH5α, and plated on LB-agar plus ampicillin for single colony selection, sequencing, and plasmid purification.

Alk1-V5 plasmid was generated by gateway cloning of pDONR223-ACVRL1(Alk1) (a gift from William Hahn & David Root, Addgene plasmid #23873) and pEF-DEST51 (Thermo) vectors using LR Clonase enzyme mix (Thermo). Plasmid was transformed into DH5α and plated on LB-agar plus ampicillin for single colony selection, sequencing, and plasmid purification. HA-tagged Alk2, Alk3 and Alk6 plasmids were a gift from Aristidis Moustakas (Addgene plasmid #80870, 80873, 80882).

FKBP12-SNAP (5 μg) and tagged ALK receptor plasmids (5 μg) were co-transfected into Hek293T cells using Super- Fect and supplied protocol. After 48 hours, cells were treated with DMSO (0.1%) or 1 μM FKVP for 30 min. After 1 hour, cells were lysed in vessel with 1 mL lysis buffer (150 mM NaCl, 50 mM Tris-HCl, 0.1% Trition-100, 5% glycerol, protease and phosphatase inhibitors) and plate scraper. Lysate was transferred to 2 mL eppendorf and rotated at 4° C. for 20 min. Lysates were centrifuged at 14000 g for 10 min, and ~1 mL supernatant was transferred to a new tube with 200 nM drug or 0.2% DMSO. 20 μL input was taken and mixed with 20 μL 2× loading buffer before boiling. Each lysate sample was then mixed with 250 μL of SNAP buffer (lysis buffer+5 mM DTT) containing 40 μL of magnetic SNAP-capture beads (New England Bio) and rotated at 4° C. for 1 hour. Beads were washed 3 times with 1 mL lysis buffer before boiling in 100 μL 2X loading buffer. Boiled lysates were vortexed and centrifuged, lysate (~90 μL) was carefully removed from beads and used for western blotting.

The same method was used for calcineurin-FK506 and mTOR-rapamycin pull-downs after transfection of 10 μg FKBP12-SNAP cDNA only.

FKBP Knockout Lines

Jurkat T and Hek293T cells were transfected as previously described with all-in-one CRISPR/Cas9 (mCherry tagged) plasmids (Genecopeia) containing guide-RNAs for FKBP12 (HCP267023-CG01-3-B), FKBP51 (HCP257374-CG01-3-B), or FKBP52 (HCP205551-CG01-3-B). After 48 hours, cells were sorted for mCherry fluorescence (650 nm laser) into 96-well plates (1 cell/well). After 2 weeks of culture, single clones were validated by western blotting.

BMP and NFAT Pathway Reporters

Jurkat T cells transfected with BRE-Luc were split into a 96-well plate (80 μL/well of $0.5\times10^6$ cells/mL)) and treated with previously stated compounds/proteins (20 μL of 5X stock in RPMI, 0.5% DMSO) for 18 h. rBMP-4 and rTGF-01 (R&D) were used as positive and negative controls, respectively. Plates were centrifuged at 3000 rpm for 10 min, then carefully aspirated. Cells were re-suspended in 100 μL lysis buffer (per well) and placed on a plate-shaker for 30 min. An aliquot of 80 μL of lysate was transferred to a white-walled 96-well plate, and luminescence was recorded 2 seconds after automated injection of luciferase substrate. Luminescence values were background subtracted (lysis buffer+substrate) and normalized to DMSO control values.

FKBP12KO Jurkat T cells transfected with FKBP12-SNAP plasmid were selected with 1200 μg/mL G418 for seven days before use in BRE-Luc assays.

Jurkat T cells transfected with NFAT-Luc were split into a 96-well plate (80 μL/well of $0.5\times10^6$ cells/mL) and treated with indicated compounds (20 μL of 5X stock in RPMI, 0.5% DMSO) 30 min before activation with PMA/Ionomycin (40 nM/1 μM). After 6 h, wells were aspirated, lysed, and measured for luminescence as previously described. FK506 and CsA served as positive control while DMSO and non-activated wells gave negative control values. With the exception of knockout cell experiments, Jurkat cells used for each experiment were transfected at the same time and cultured together overnight until plating and treatment the following day.

Declaration of Ethical Animal Care and Use

Goto-Kakizaki (GK) type-2 diabetic rats obtained from Charles River (Boston, MA) were housed in a pathogen-free facility and cared for according to NIH guidelines and a protocol approved by the Johns Hopkins University Animal Care and Use Committee (ACUC). Both male and female GK rats at age of 4-5 months were used in this study.

In Vivo Excisional Wound Model

Full-thickness wounds were created in the dorsal skin of rats with a sterile disposable biopsy punch (8 mm in diameter). The animals were injected subcutaneously with saline, AMD3100 (1 mg/kg) plus FK506 (0.1 mg/kg) or AMD3100 (1 mg/kg) plus FKVP (0.1 mg/kg) immediately after wounding and every other day until complete healing, defined as complete re-epithelialization of the wound area. For assessing the role of BMP signaling, animals were injected intraperitoneally (i.p.) with LDN-193189 (2 mg/kg/day) in addition to standard saline or AF treatment. Wounds were evaluated daily according to the method described previously (Lin et al., 2014).

Immunohistochemistry

Cut sections of 5 μm were prepared from frozen tissue for immunohistochemistry staining. Frozen sections were fixed with acetone at −20° C. for 10 min and dried for 1 h at room temperature. After inactivation of endogenous peroxidase and blocking of nonspecific antibody binding, the specimens were incubated with anti-CD133 (1:300, ab19898; Abcam) at 4° C. overnight. The tissue sections were then subsequently incubated with biotin-conjugated goat anti-rabbit IgG (1:200, #14708S Cell Signaling, Danvers, MA) for 30 minutes at room temperature. The VectaStain Elite ABC kit (HRP) (Vector Laboratories, Burlingame, CA) was used to increase the sensitivity of the staining. Diaminobenzidine tetrahydrochloride (5 min, D4293, Sigma-Aldrich, St. Louis, MO) was used as the chromogen, and Mayer's Hematoxylin (30 s, Dako, S3309) was used for counterstaining.

Statistics

The one-way analysis of variance (ANOVA) was used to determine the statistically difference in wound healing among AF, AF+LDN, Saline and S+LDN groups or between AF, AV and Saline groups when comparing days of wound healing. Bonferroni-Holm post-hoc procedure was used for p value adjustment. $p<0.05$ is considered significantly different.

Example 1

To conduct a structure-activity relationship study, the inventors synthesized new analogs of FKVP containing the pyridine core structure. In the past, the inventors and others have relied on ruthenium-catalyzed cross metathesis reaction (CM) to modify the terminal alkene of FK506 (C40) to generate non-immunosuppressive FK506 analogs. Unfortunately, FKVP and other nitrogen-containing analogs could only be obtained in very low yields. This is most likely due to the nitrogen lone electron pair that competitively coordinates to the ruthenium metal center. The use of soluble tosylated salts of amines could improve yields, but it did not help in the case of FKBP.

To address the issue associate with nitrogen base-containing substrates in the CM reaction, we turned to the Heck reaction as an alternative, since palladium catalysts used in the Heck reaction are compatible to nitrogen-containing heterocycles such as pyridine. After optimizing the reaction conditions, we found that reacting FK506 with 4-Iodopyridine (2.0 equiv.) in the presence of $Pd(OAc)_2$ (10 mol %) and $P(o\text{-}tol)_3$ (20 mol %) in DMF at 100° C. gave the best yield (66%).

As an example, to a mixture of FK-506 (0.0500 mmol, 40 mg, 1.0 equiv), aryl halides (2.0 equiv) and $Pd(OAc)_2$ (0.00500 mmol, 1.1 mg, 0.10 equiv) and $P(o\text{-}tol)_3$ (0.0100 mmol, 3.0 mg, 0.20 equiv) in flame-dried 10 mL-Schlenk tube, dry DMF(1.0 mL) and $Et_3N$ (0.10 mL) dried over $K_2CO_3$ was added under Argon balloon protection, and the mixture was stirred at 100° C. The reactions were monitored by mass spectrometry. When the reaction was finished, the reaction mixture cooled to room temperature, and was purified by flash column with gradient solvent (dichloromethane and methanol) to give the corresponding product. If necessary, PLC was used as further purification to separate epimers.

With FKVP as the lead, 7 nitrogen-containing heterocyclic halides with a pyridine core and 4 halides with substituted anilines were selected as substrates for the Heck reaction. To our delight, all halide substrates were successfully coupled to FK506 with moderate to good yields (see Table 1).

The halide substrates displayed distinct reactivity in the Heck reaction. First, bromides and iodides gave similar yields. Second, electron-withdrawing groups on the pyridines and quinolines appeared to increase the yields (Table 1, entry 4,6,7). Third, unprotected anilines gave the lowest yields (Table 1, entry 9-11). Importantly, the unreacted FK506 starting material in the reaction mixture was easily separated from the more polar nitrogen-containing products with flash chromatography.

Example 2

Figure 2A:
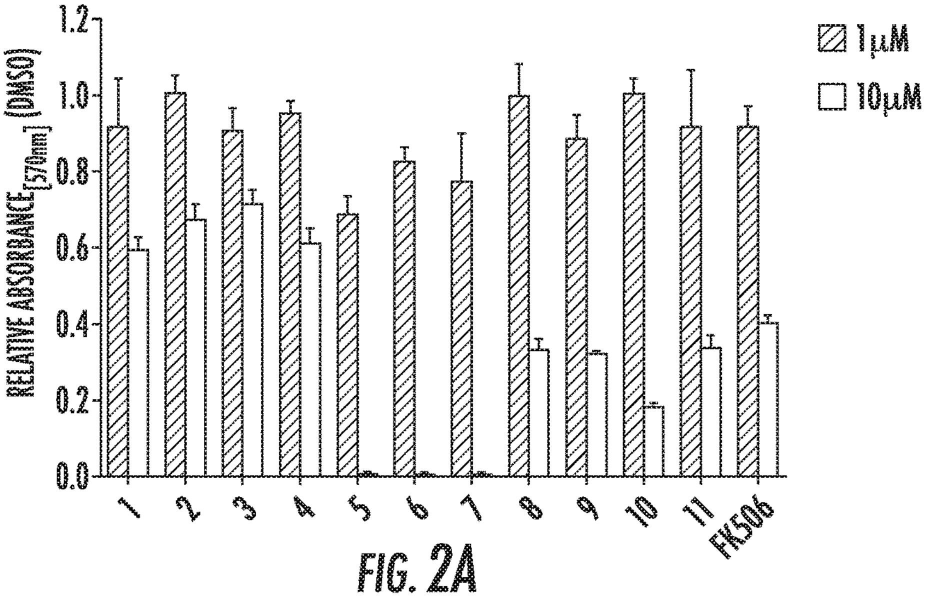
FIGS. 2A-2C show FK506 analogs display variable immunosuppressive qualities.

With FK506 analogs in hand, their effects on cell viability, BMP activation and NFAT activation at two concentrations (FIG. 2) were assessed. In the HUVEC cell viability assay, we found that quinoline analogs (5b-7b) inhibited cell proliferation at 10 μM (FIG. 2*a*), while other compounds were comparable to FK506 in their cytotoxicity.

Figure 2B:
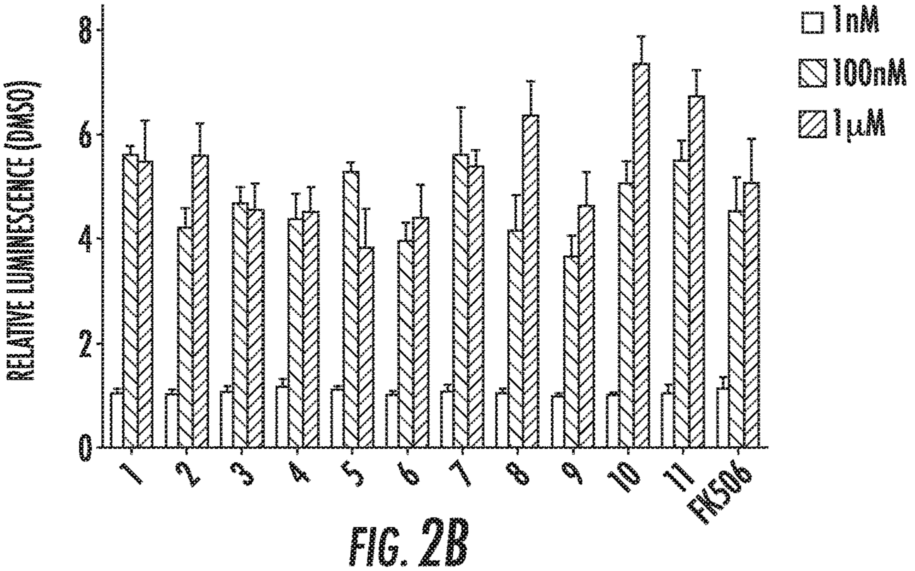

We used a BMP-response-element (BRE) pathway reporter (luciferase under the control of the ID1 gene promoter) in Jurkat T cells to determine whether the new analogs were capable of activating the BMP signaling pathway. Initial screening of the compounds showed that most analogs had similar activity as FK506 or FKVP. This is somewhat expected, as we have previously shown that FKBP12 binding is necessary and sufficient for activation of BMP signaling (FIG. 2*b*).

Figure 2C:
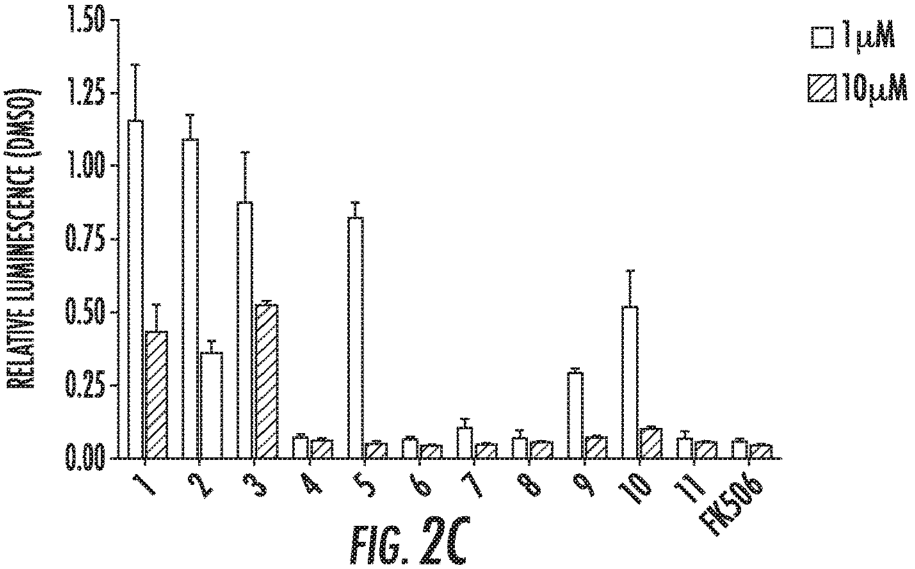

To determine the effect of the analogs on calcineurin, we employed a PMA/ionomycin-activated Nuclear Factor of Activated T-cells (NFAT) reporter in Jurkat T cells[8d] (luciferase under the control of the IL-2 promoter) (FIG. 2*c*). Two analogs (2b, 3b) did not cause significant inhibition of the NFAT-Luciferase reporter at concentrations up to 10 μM, similar to FKVP (1b). Surprisingly, most other analogs showed either partial or nearly complete inhibition of the NFAT reporter at 1 μM (FIG. 2*c*). It is noteworthy that some of the immunosuppressive analogs, including 5b, 6b and 7b, have bulkier substituents than 2b and 3b due to the presence of a fused aromatic ring. How those bulkier groups are accommodated at the binding site of calcineurin remains to be determined.

Example 3

Figure 3:
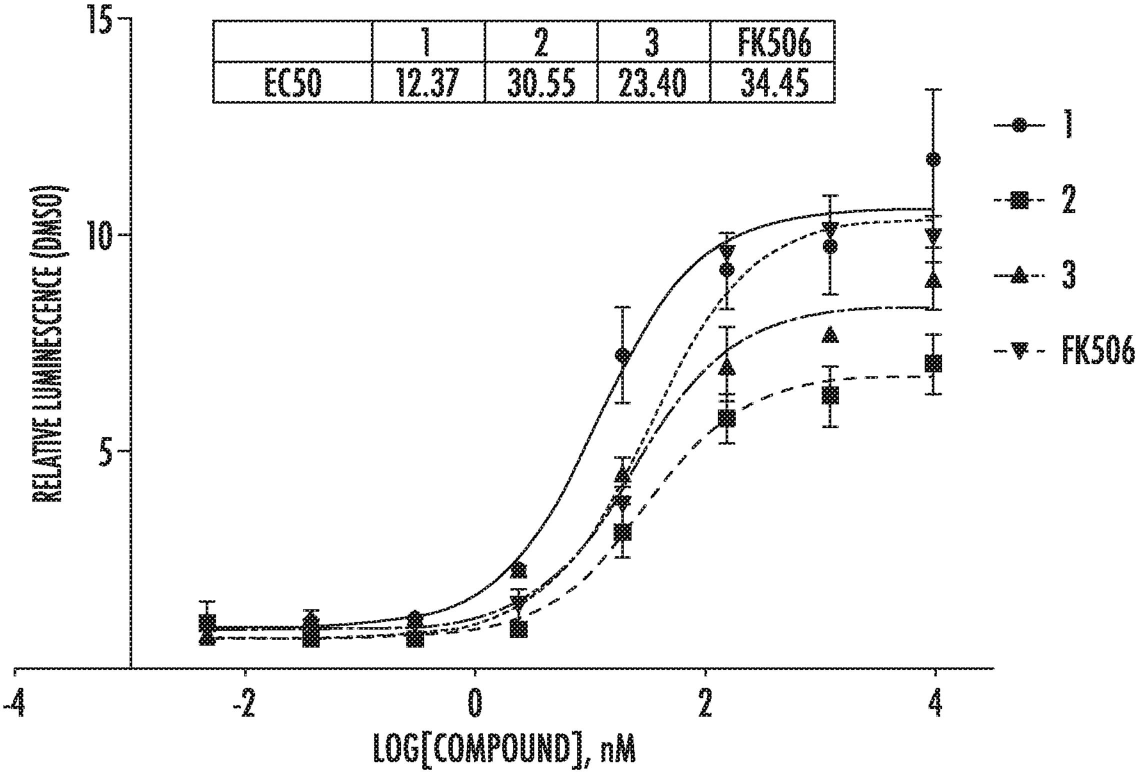
FIG. 3 depicts dose-response curves for BMP reporter activation by three non-immunosuppressive analogs and FK506.

We determined $EC_{50}$ values of three non-immunosuppressive analogs (1b-3b) in the BMP luciferase assay. All 3 analogs were found to be slightly more potent than FK506 (FIG. 3), likely attributable to increased solubility due the more polar pyridine substituents. Among the three analogs, FKVP remained the most active with an $IC_{50}$ of 12.4 nM.

Example 4

Figure 4A:
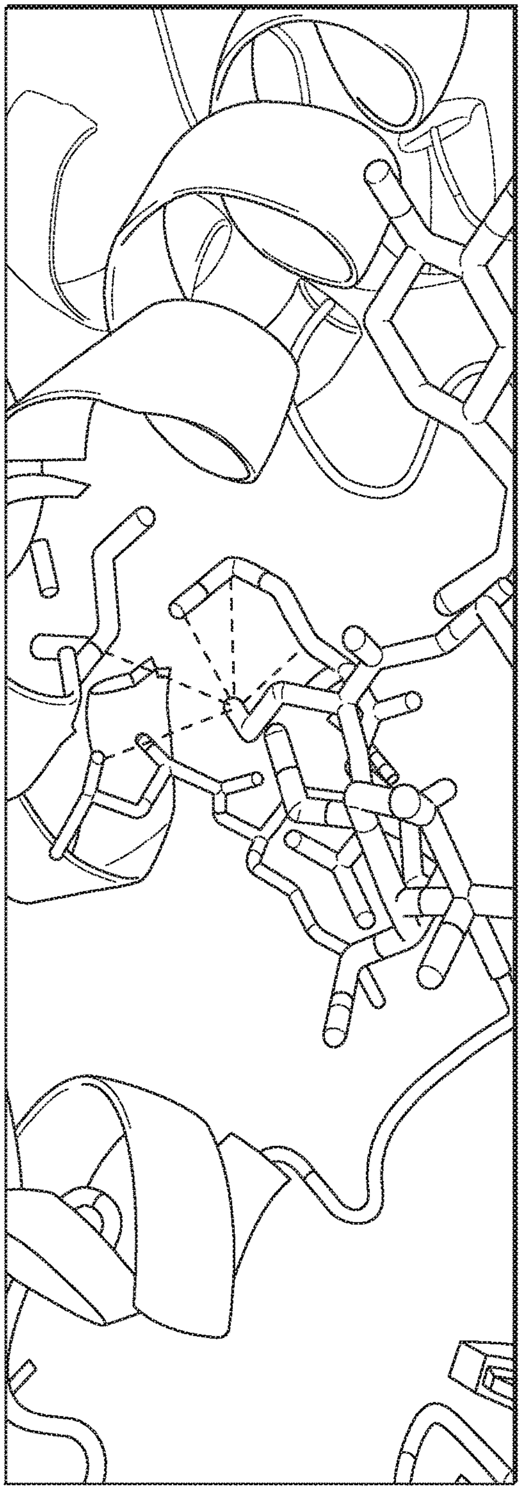
FIGS. 4A-4B show binding detail towards calcineurin.
Figure 4B:
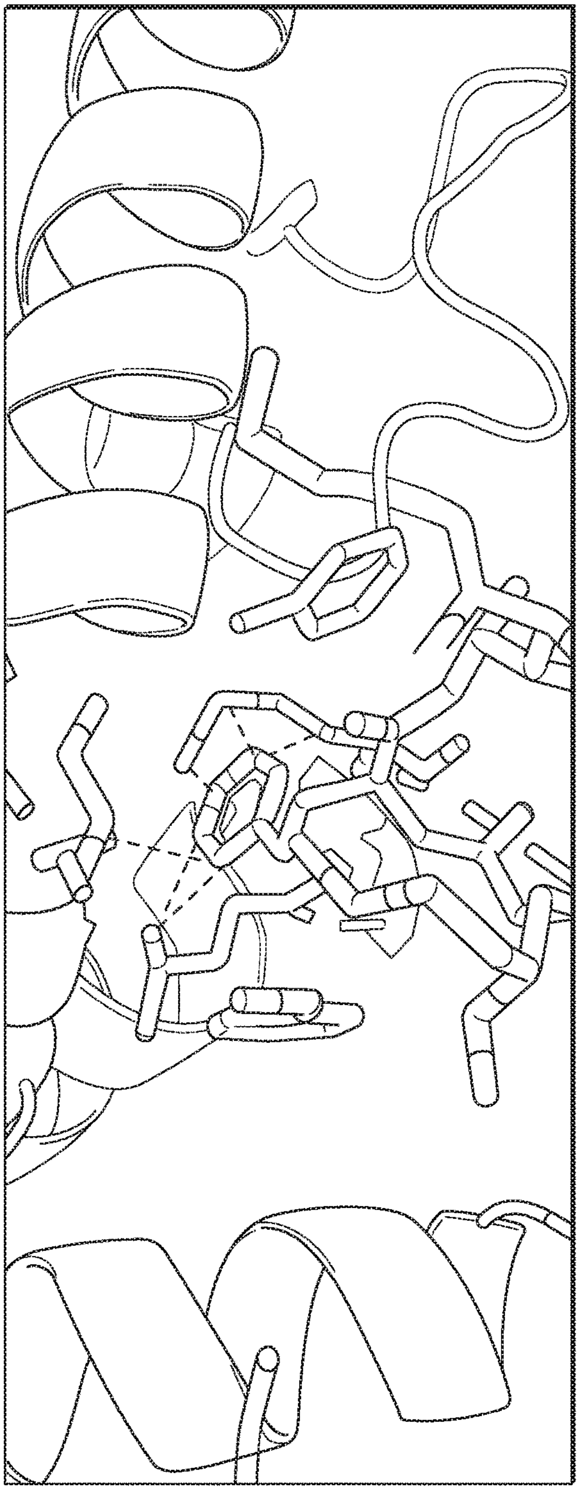

The structure of the complex of FKBP12-FK506-calcineurin has been previously determined by X-ray crystallography. In this complex, the terminal alkene of FK-506 fits into a binding pocket in calcineurin formed by hydrophobic amino acids (FIG. 4*a*). When modeled in place of FK506, the pyridine moiety in FKVP (1b) has a steric clash with residue M118 of calcineurin (FIG. 4*b*), which explains the elimination of calcineurin binding by analogs 1b-3b. However, how other analogs some of which contain bulkier substituents than FKVP at the same position remain immunosuppressive cannot be explained by the structure.

After surveying the pKa values of all nitrogen-containing analogs, we noticed that compounds with higher pKa values (1b, 2b, 3b, 5b) showed less calcineurin inhibition. Conversely, those with a lower pKa caused by electron-withdrawing groups were all immunosuppressive at 1 μM (4b, 6b, 7b). The pKa value of aniline (9b-11b) is lower than pyridine (1b), which may also explain its retention of inhibitory activity for calcineurin. These observations suggest that the formation of positively charged pyridinium appendage at the terminal alkene of FK506 plays a more important role in disrupting the interaction between the terminal alkene of FK506 and the hydrophobic pocket in calcineurin. These observations present an alternative and complementary mechanism for the loss of calcineurin inhibition in non-immunosuppressive FK506 analogs, which in the past has been rationalized by a large molecular "bump" to sterically hinder calcineurin binding. It is likely that the same binding pocket in calcineurin has significant conformational flexibility to accommodate non-charged bulky aromatic rings such as those present in 4b, 6b and 7b.

In summary, the inventors have developed an inventive method comprising a one-step synthesis of FK506 analogs containing nitrogen bases using the Heck reaction. Three non-immunosuppressive analogs with higher potency in activating the BMP signaling pathway were identified. It was found that a key element in disrupting FK506-calcineurin interaction is through electrostatic rather than steric interactions. Given the role of BMP signaling in wound healing and tissue regeneration, the newly developed synthetic route to FKVP and analogs will facilitate the development of non-immunosuppressive analogs of FK506 for regenerative medicine.

Example 5

Modification of FK506 at $C_{40}$ led to a non-immunosuppressive analog-FKVP

Figure 5B:
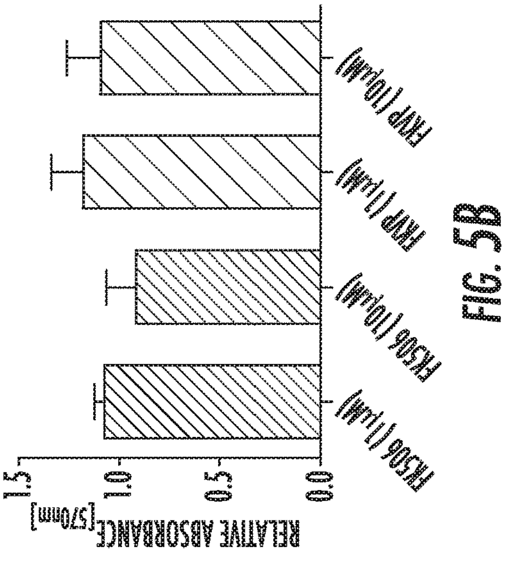
FIGS. 5A-5C illustrate the novel synthesis of a non-immunosuppressive analog (FKVP) by modifying FK506 at C40 position.
Figure 5C:
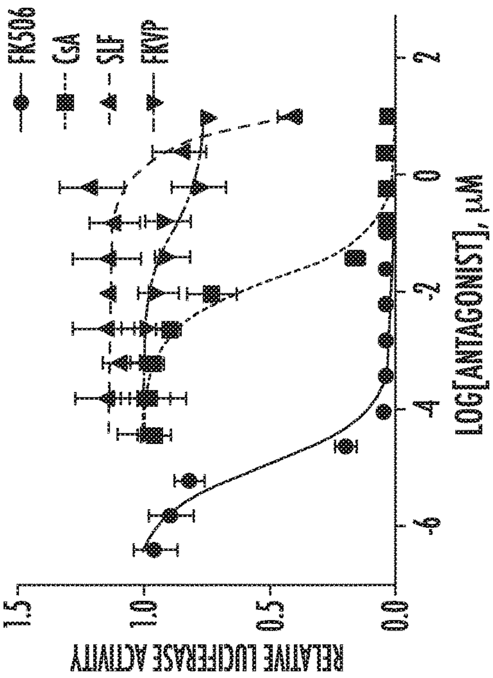
Figure 5A:
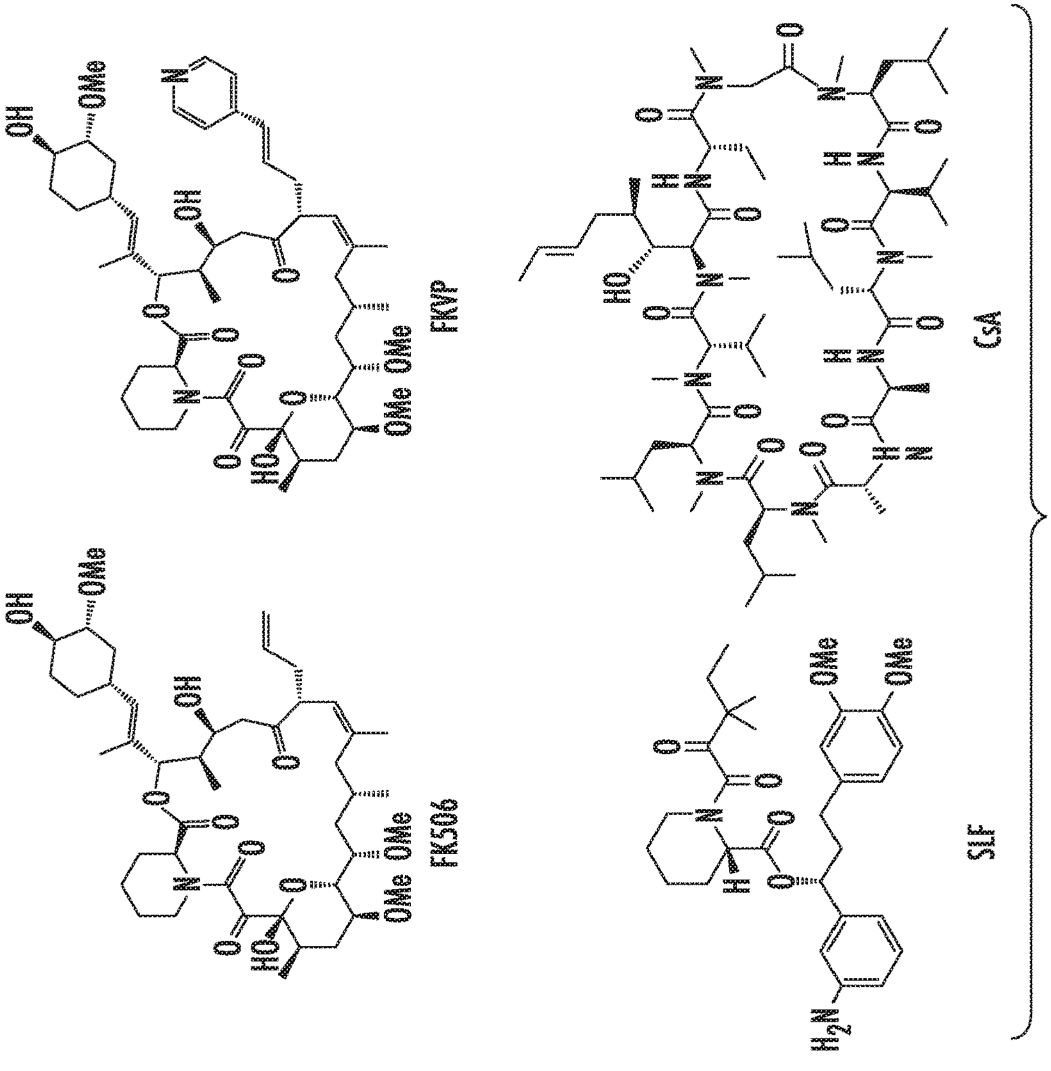
Figure 6:
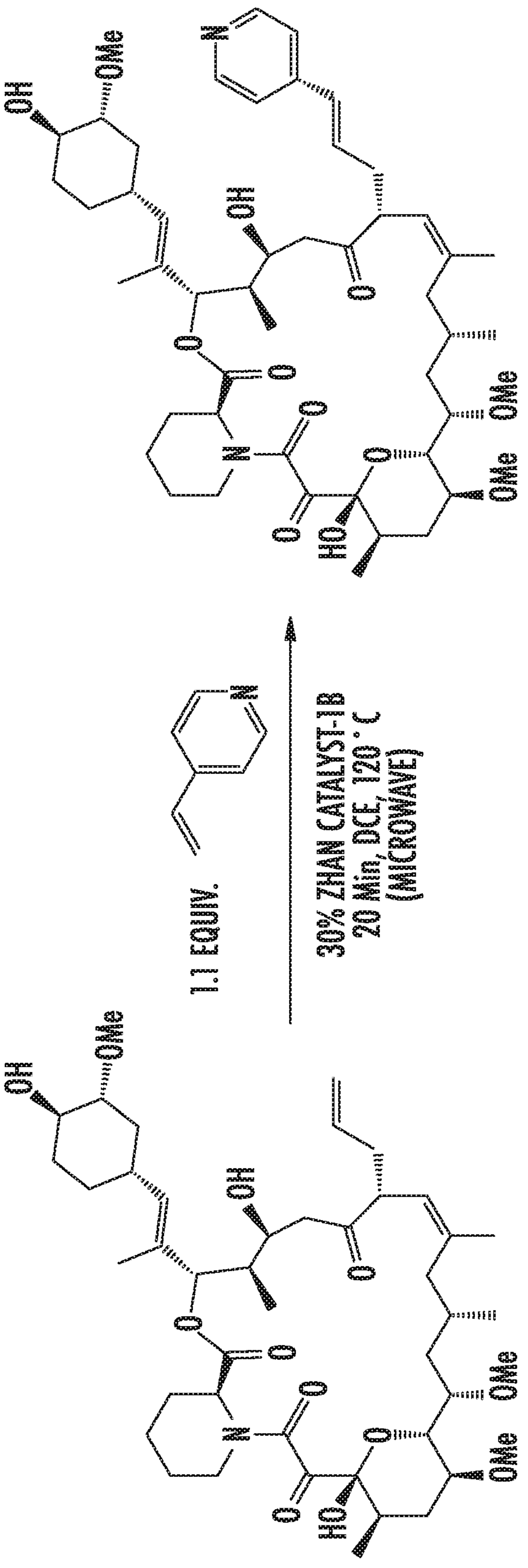
FIG. 6 shows a schematic of FVKP synthesis via ruthenium catalyzed cross metathesis. Synthesis scheme of FVKP.
Figure 7B:
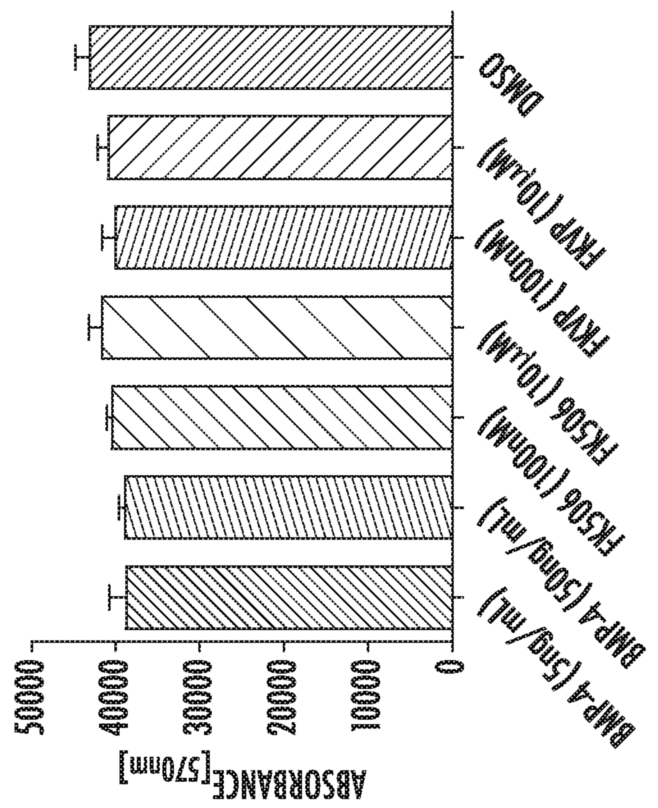
FIGS. 7A-7B depict FVKP treatment of Jurkat cells.
Figure 7A:
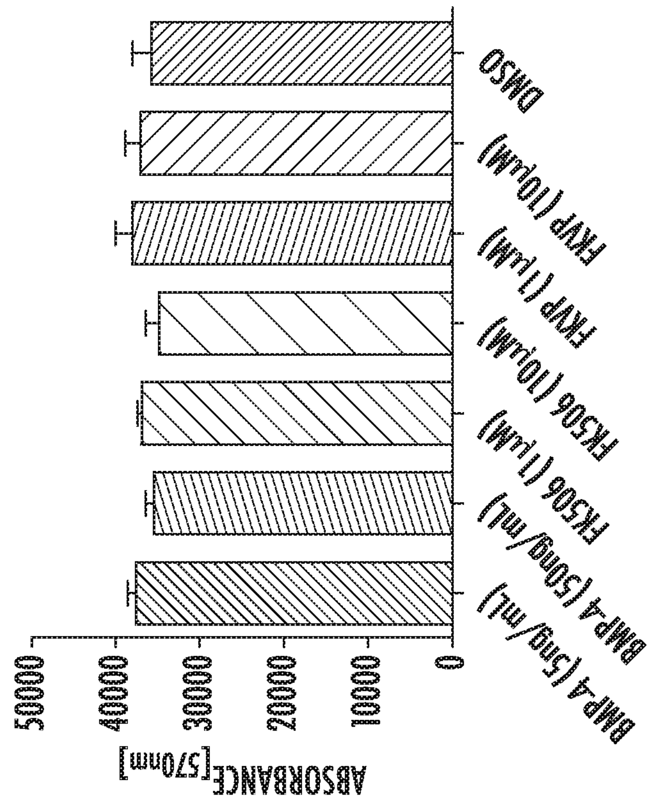
Figure 8B:
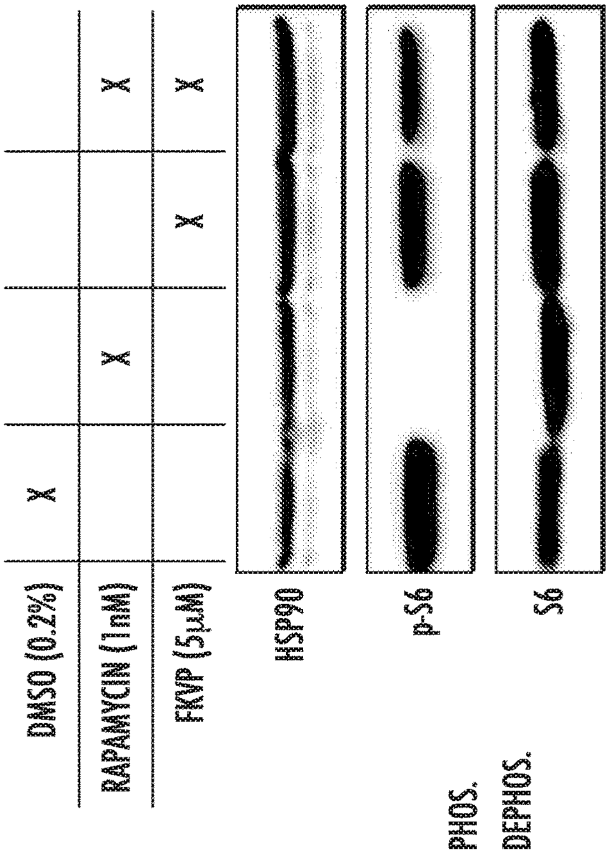
FIGS. 8A-8B show that FKVP competes both FK506 and rapamycin for FKBP12 binding. Both FK506 and rapamycin require FKBP12 for activity.
Figure 8A:
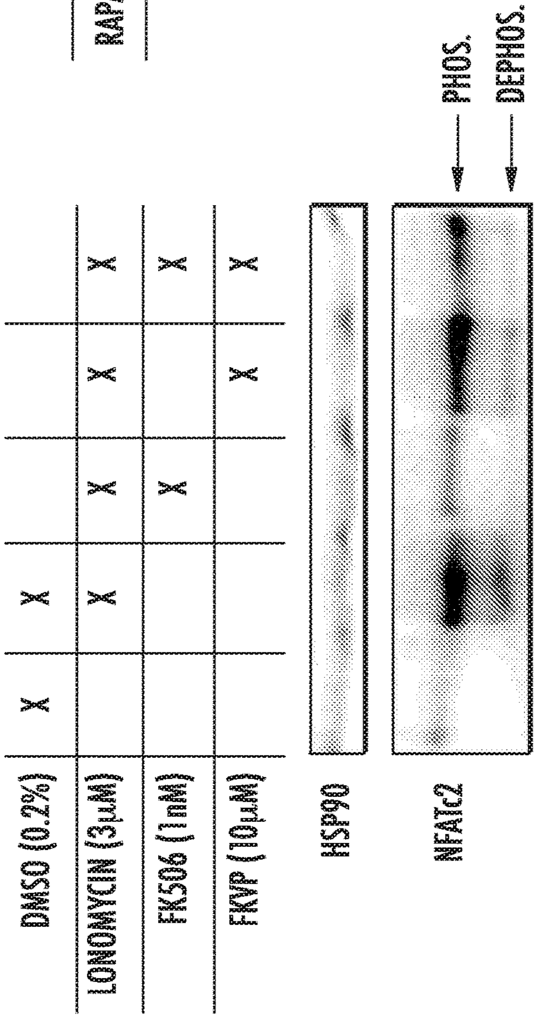

The in vivo immunosuppressive activity of FK506 has been established to be mediated through the inhibition of calcineurin (Bueno et al., 2002). Previous studies have shown that modification at the terminal alkene of FK506 could block calcineurin inhibition while retaining FKBP binding (Clemons et al., 2002). To determine if calcineurin inhibition was required for enhanced healing by the AF combination, we designed and synthesized a non-immunosuppressive analog of FK506 by using cross-metathesis to fuse a vinyl pyridine moiety to the terminal alkene as a "bump" in the effector domain of FK506. The resultant analog was named FKVP (FIG. 5*a*). The newly added pyridine moiety was intended to increase water solubility while providing steric bulk to disrupt its interaction with calcineurin (FIG. 6). The cytotoxicity of FKVP was assessed and compared to that of FK506 in both Jurkat T (FIG. 5*b*, FIG. 7*a*) and primary HUVEC cells (FIG. 7*b*). Like FK506, FKVP did not affect cell viability at concentrations up to 10 μM (FIG. 5*b*). We then determined the effect of FKVP on a PMA/ionomycin-activated NFAT-luciferase reporter gene in Jurkat T cells (Clemons et al., 2002). While both FK506 and CsA exhibited potent inhibition of the reporter, FKVP did not cause significant inhibition at concentrations of up to 10 μM (FIG. 5c), suggesting that FKVP is no longer capable of inhibiting calcineurin. To confirm that FKVP retained the ability to bind FKBP, we applied it to a competition assay in combination with FK506 and rapamycin, as sequestration of free FKBP will prevent the formation of active FKBP12-FK506 or FKBP-rapamycin complexes and thus antagonizing the activity of both drugs (Rao et al., 1997, Abraham et al., 1996). The effect of FK506 on calcineurin was determined using as a readout the phosphorylation state of NFATc2. Thus, FK506 blocked the dephosphorylation of NFATc2 in response to stimulation with PMA and ionomycin (FIG. 8a). The presence of 10 μM of FKVP reversed the inhibitory effect of FK506 on NFATc2 dephosphorylation, suggesting mutual antagonism between FKVP and FK506. Similarly, we examined the effect of rapamycin on mTOR activity as judged by the phosphorylation state of its substrate p70s6k. Once again, high concentration of FKVP reversed the inhibition of rapamycin on p70s6k phosphorylation (FIG. 8b). Together, these results clearly showed that FKVP is capable of antagonizing the activities of both FK506 and rapamycin through competitive binding to endogenous FKBP proteins.

Example 6

FKVP in combination with AMD3100 accelerated wound healing.

Figure 9C:
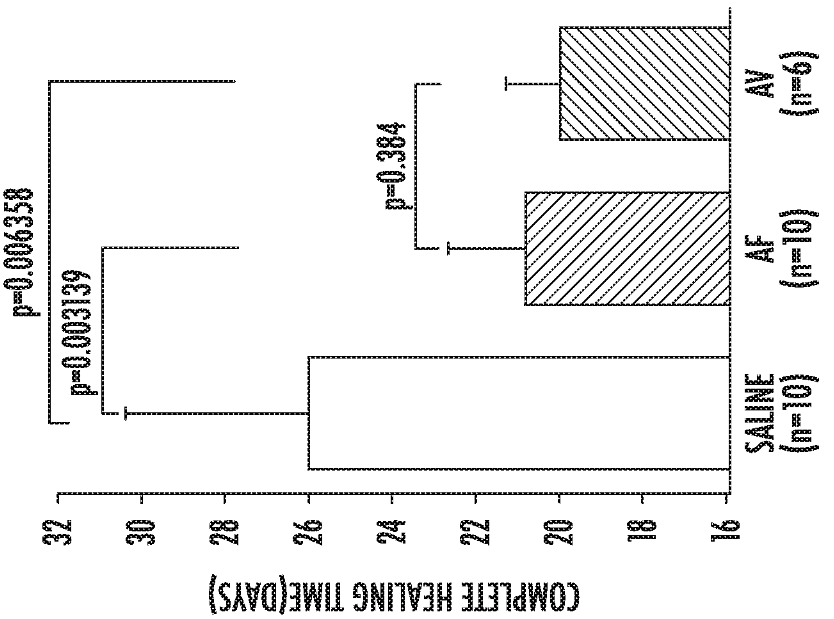
FIGS. 9A-9C show accelerated wound healing in diabetic GK rats treated with combination of AMD3100 and FK506 or FKVP.
Figure 9A:
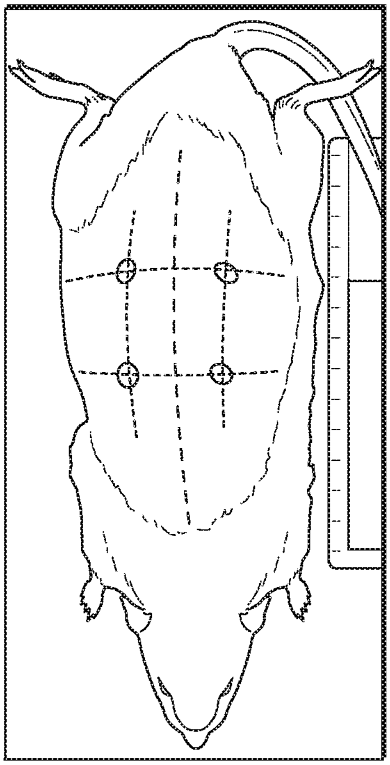
Figure 9B:
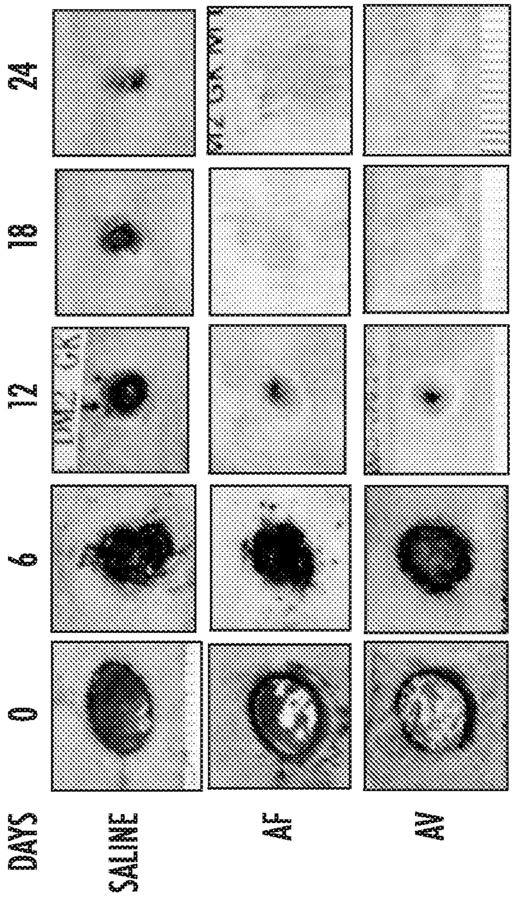

We have previously reported a synergistic activity of AMD3100 and low-dose FK506 (AF) in accelerating wound healing after full-thickness skin excision (Lin et al., 2014). To determine if FKVP, has the equivalent effect, we performed a wound healing experiment in a rat model of type 2 diabetes. Four full-thickness wounds were generated by 8-mm diameter circular excisions on the shaved back of a diabetic GK rat and each wound site was photographed digitally at the indicated time intervals (FIG. 9a). Re-epithelialization of entire wound areas was used as a defining parameter of complete healing, and the complete healing time of four wounds in each animal was calculated in days (FIG. 9b).

Wounded rats were divided randomly into three experimental groups and received subcutaneous injections of saline, AF (AMD3100 (1.0 mg/kg) plus FK506 (0.1 mg/kg)) or AV (AMD3100 plus FKVP (0.1 mg/kg)) immediately after wounding and every other day until complete healing. While the saline control group showed an average complete healing time of 26 days, the animals treated with AF exhibited significantly faster healing as wounds reached complete re- epithelialization at day 21, which is consistent with our report in non-diabetic rodent models of surgical excisional wounds (Lin et al., 2014). Importantly, ten rats receiving AV therapy displayed an AF-equivalent effect of significantly reduced time for complete healing from 26 to 20 days (FIG. 9c). These results strongly suggest that inhibition of calcineurin is not involved in the synergistic activity of AMD3100 and FK506 in accelerating wound healing.

Example 7

Figure 10C:
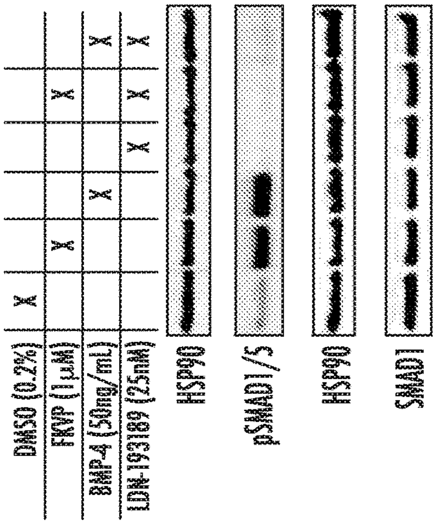
FIGS. 10A-10C show that non-immunosuppressive analogs, such as the compounds of formula I, activate ID-1 reporter and pSMAD1/5 phosphorylation through BMP type 1 receptor activation.
Figure 10B:
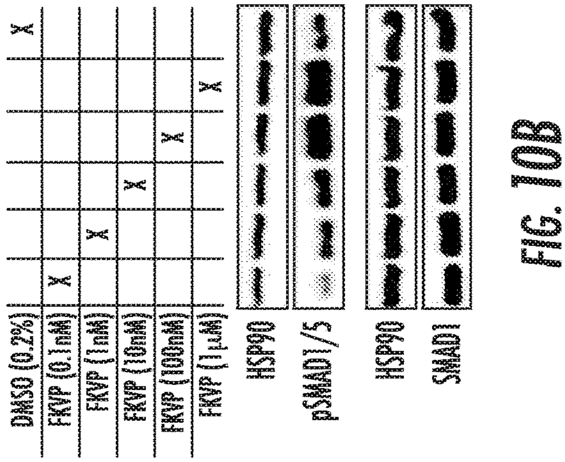
Figure 10A:
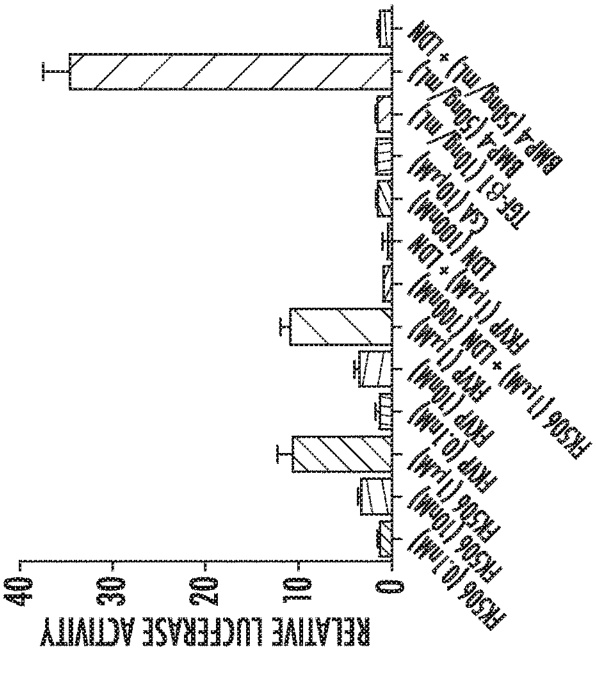

FKVP activates ID-1 reporter and SMAD1/5 phosphorylation through BMP type 1 receptor Having ruled out calcineurin as a relevant mediator of the WH acceleration activity of FK506, we turned to FKBP12 and the BMP signaling pathway it is reported to regulate. We began by determining whether FK506 and FKVP are both capable of activating the BMP signaling pathway by employing a BMP-response-element (BRE) pathway reporter (luciferase under the control of the ID1 gene promoter) (Spiekerkoetter et al., 2013) in Jurkat [E6.1]T cells. The Jurkat line was found to express working components of BMP signaling (BMPRs, SMAD1/5) in addition to high levels of FKBP12 and CXCR4, making it an excellent model system. To confirm reporter selectivity, rBMP-4 and rTGF-01 were used as positive and negative controls, respectively. Treatment with both FKVP and FK506 caused dose-dependent activation of the reporter, and the increases in luciferase activity were completely blocked by the selective BMP1R inhibitor LDN-193189 (LDN) (FIG. 10a). In contrast to FK506 and FKVP, cyclosporine A (CsA) did not activate the reporter (FIG. 10a), consistent with the notion that calcineurin is not involved in BMPR1 kinase activation by FK506.

Figure 11:
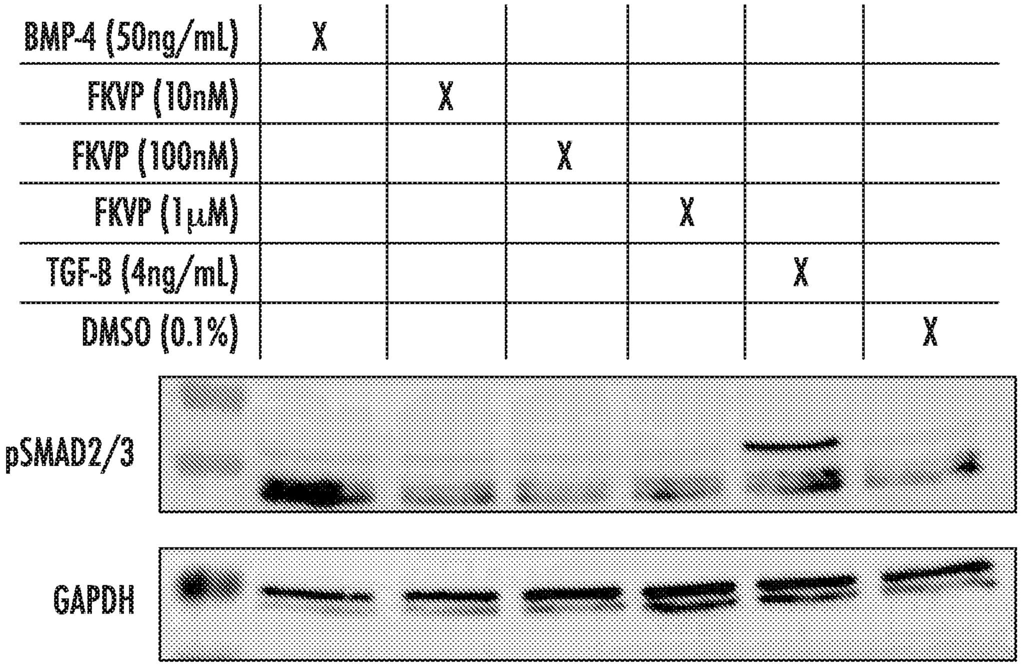
FIG. 11 shows that unlike SMAD/16, FKVP does not activate SMAD2/3 phosphorylation. Jurkat cells show no appreciable increase in SMAD2/3 phosphorylation after 2 hr. FKVP treatment compared to positive controls (TGF-β1).
Figure 12:
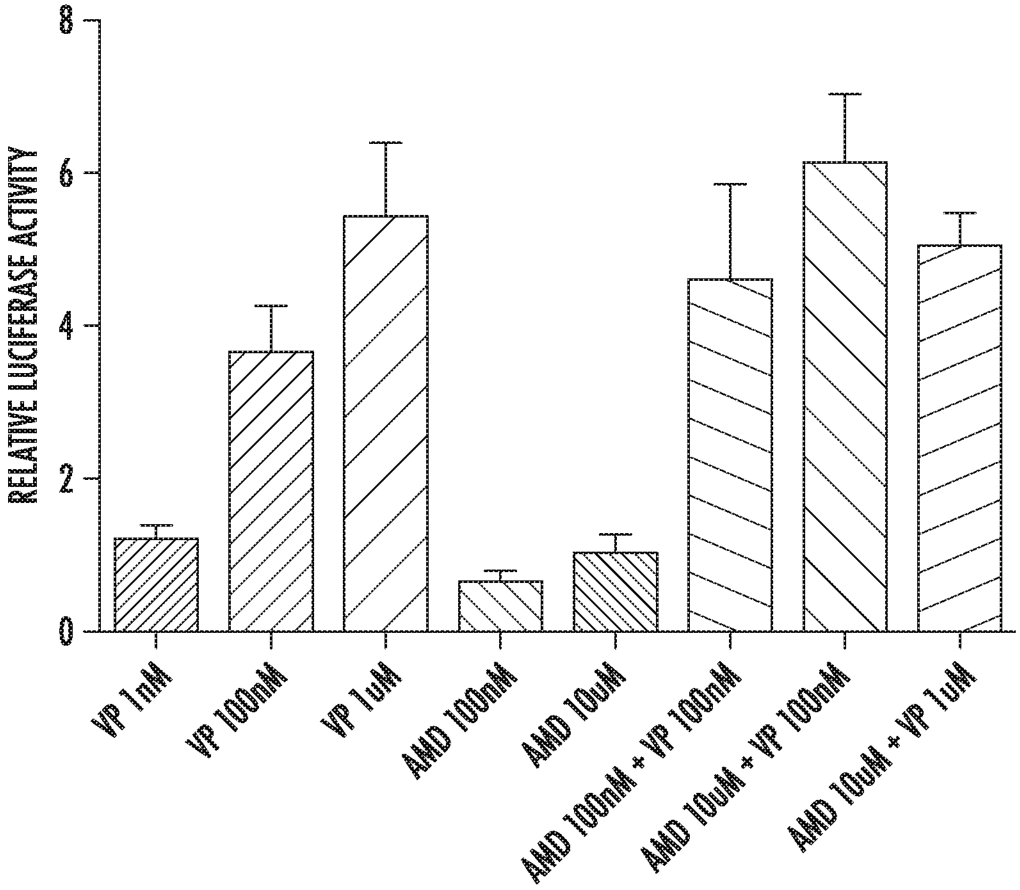
FIG. 12 shows that AMD-3100 does not affect BMP signal ng alone, or in combination with FKVP. FKVP and AMD3100 single and combination treatments in Jurkat BMP FKVP luciferase assay (n=3). Relative luciferase activities were determined upon normalization to DMSO control values. Error bars represent standard deviation from mean.
Figure 13:
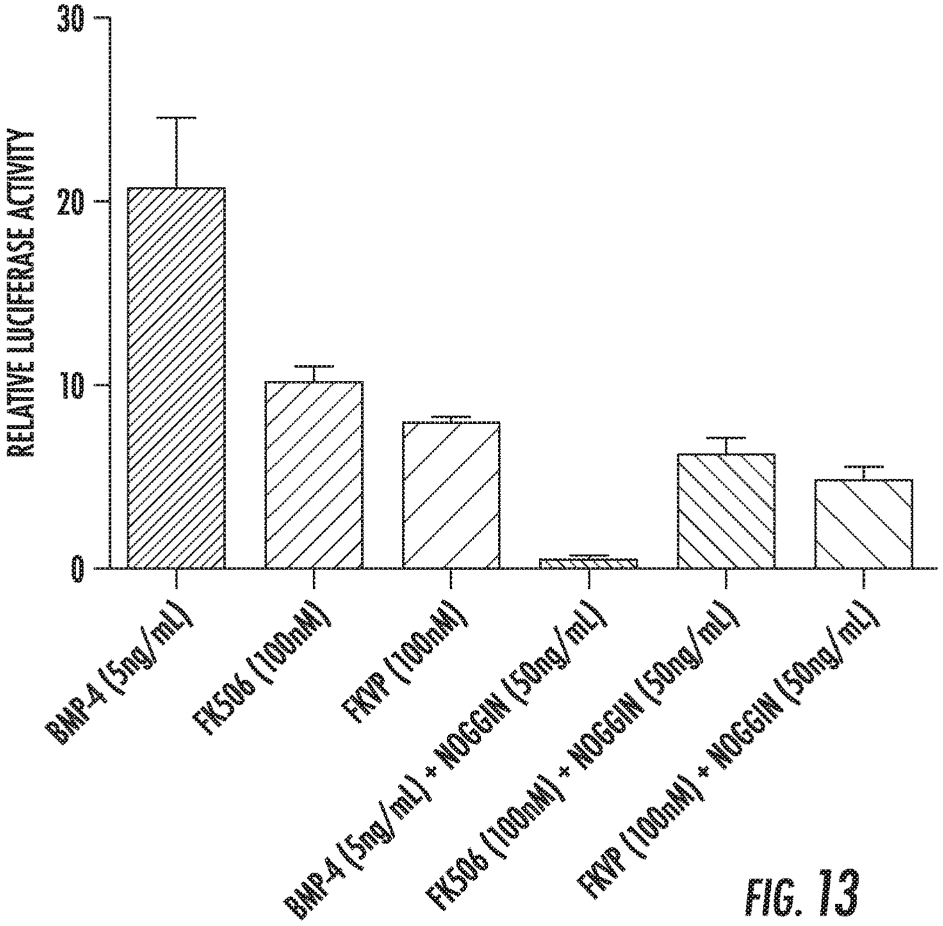
FIG. 13 shows that FKVP activates BMP signaling in the presence of the BMP inhibitor, Noggin. BMP-4, FVKP, FK506 and Noggin combination treatments in Jurkat BMP activation assay (n=3). Relative luciferase activities were determined upon normalization to DMSO control values. Error bars represent standard deviation from mean.
Figure 14:
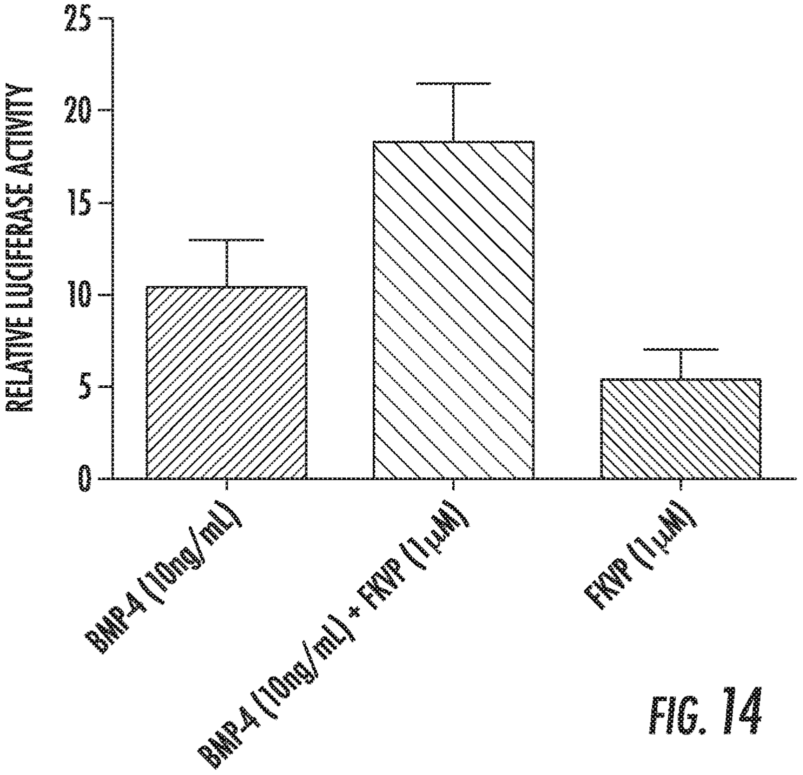
FIG. 14 illustrates that FKVP increases sensitivity of cells t BMP-4 stimulation. BMP-4, FVKP, and combination treatments in Jurkat BMP activation as ay (n=3). Relative luciferase activities were determined upon normalization to DMSO control values. Error bars represent standard deviation from mean.
Figure 15B:
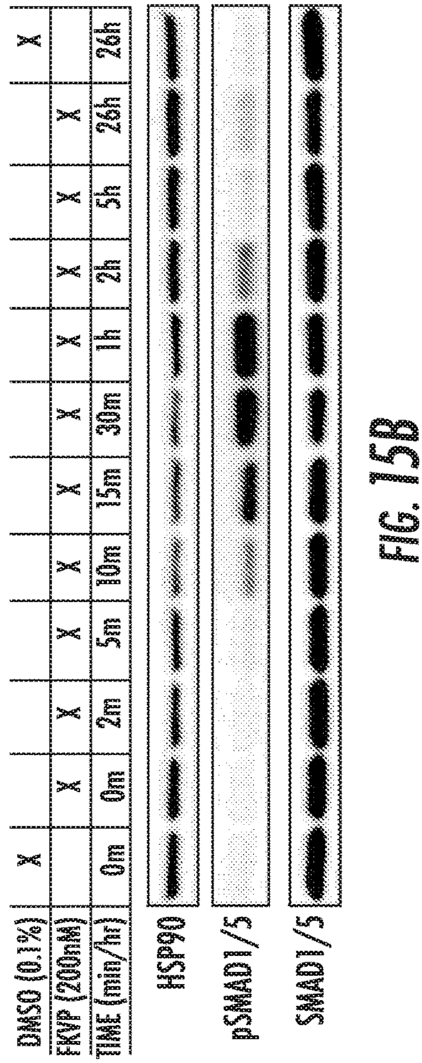
FIGS. 15A-15C depict FKVP activates SMAD1/5 phosphorylation and ID-1 expression in HUVEC.
Figure 15C:
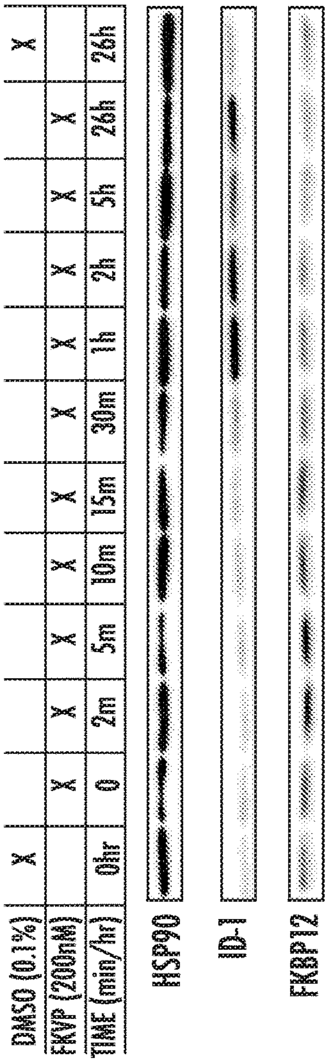
Figure 15A:
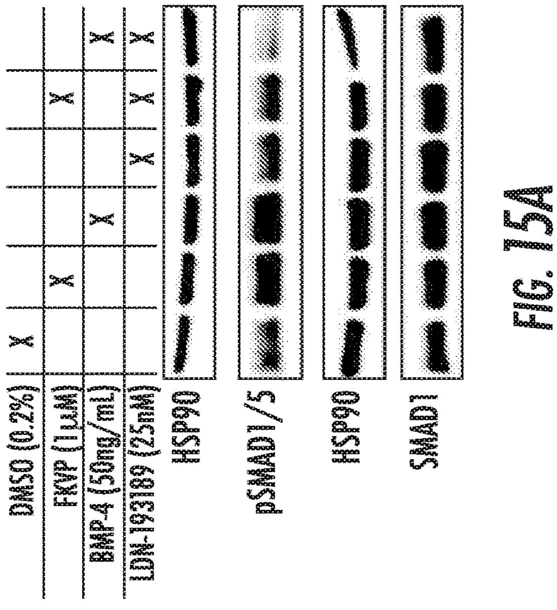

To study downstream BMPR1 signaling events, we determined the effects of FK506 and FKVP on the phosphorylation of SMAD1/5. Both compounds induced SMAD1/5 phosphorylation in a dose-dependent manner (FIG. 10b), an effect abolished by LDN treatment (FIG. 10c). In contrast, there were no increases in phosphorylated SMAD2/3 under the same conditions (FIG. 11), suggesting that while FKBP12 may bind TGF-β receptors (Chen et al., 1997), its dissociation is insufficient to activate receptor kinase activity in the absence of TGF-β. This result is in agreement with previous studies showing that FK506 and non-functional analogs are incapable of activating TGF-3 pathway reporters without the addition of exogenous ligand (Spiekerkoetter et al., 2013, Wang et al., 1996). In the BRE-luciferase reporter, AMD3100 was found to have no effect on ID-1 promoter stimulation alone or in combination with FKVP (FIG. 12), suggesting that the synergistic activity of these drugs does not occur at the level of BMP signaling. Furthermore, we found that the extracellular BMP-inhibitor protein, Noggin, was not effective at reducing FK506- or FKVP-mediated induction of the BMP reporter (FIG. 13). These observations suggest that endogenous BMP is not required for signaling activation by FK506 or FKVP, and that these compounds could activate BMP in tissues with under-expression of BMP protein, or overexpression of extracellular inhibitors like Noggin. In addition, FKVP boosted the sensitivity of cells to BMP-4 stimulation in an additive fashion, suggesting that inhibition of FKBP12 binding promotes receptor activation by endogenous ligand (FIG. 14). Both SMAD1/5 phosphorylation and ID-1 expression were significantly increased in HUVEC cells after FKVP treatment (FIG. 15), providing evidence that more than one cell type is sensitive to BMP activation by FKVP. Together, these results indicated that both FK506 and FKVP are capable of activating BMPR1 kinase signaling, raising the possibility that this activation plays a key role in the healing acceleration activity of FK506 in the AF combination therapy.

Example 8

FKBP12 alone is required for FKVP-induced SMAD1/5 phosphorylation.

Figure 16A:
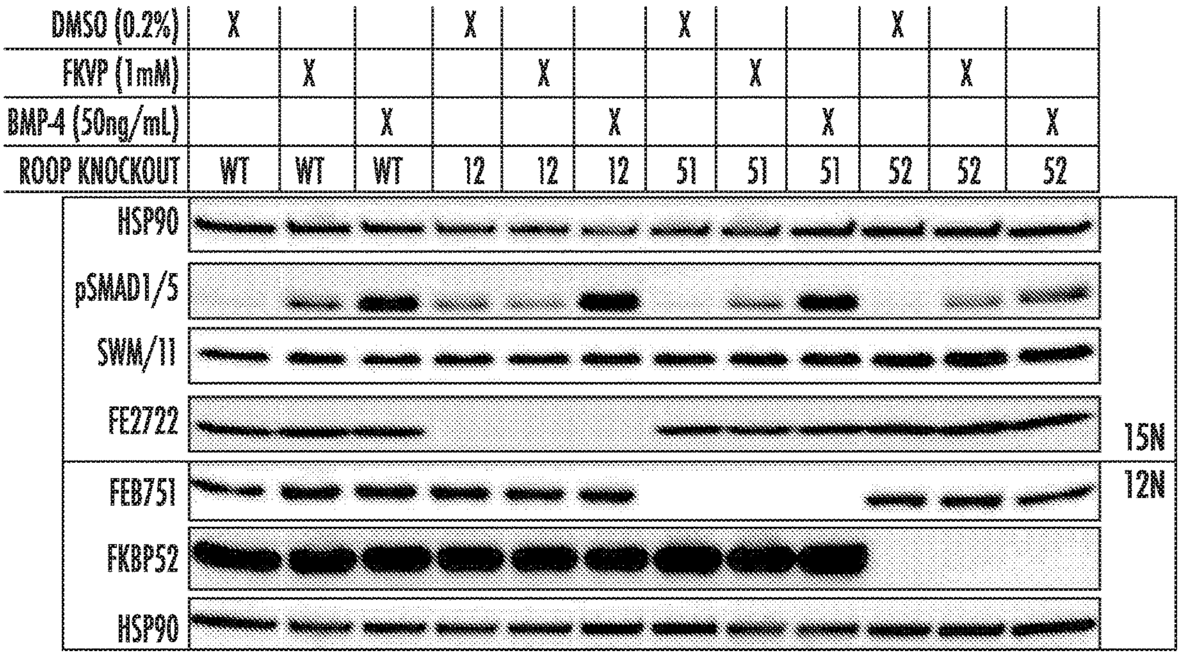
FIGS. 16A-16D show FKBP12 alone is required for FK506 and FKVP-induced SMAD1/5 phosphorylation.
Figure 16B:
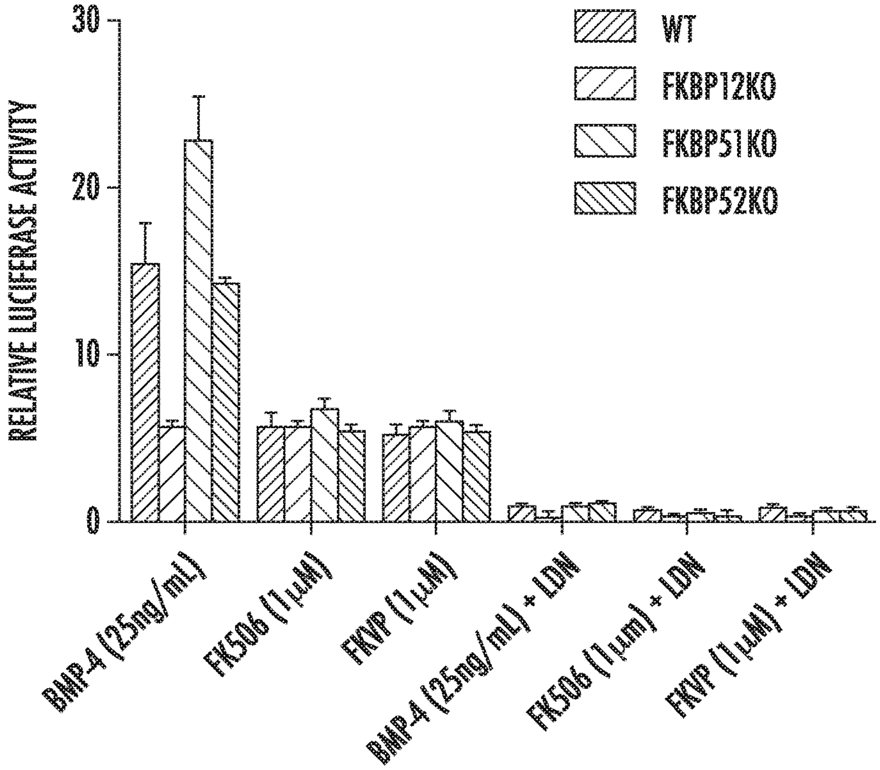
Figure 16C:
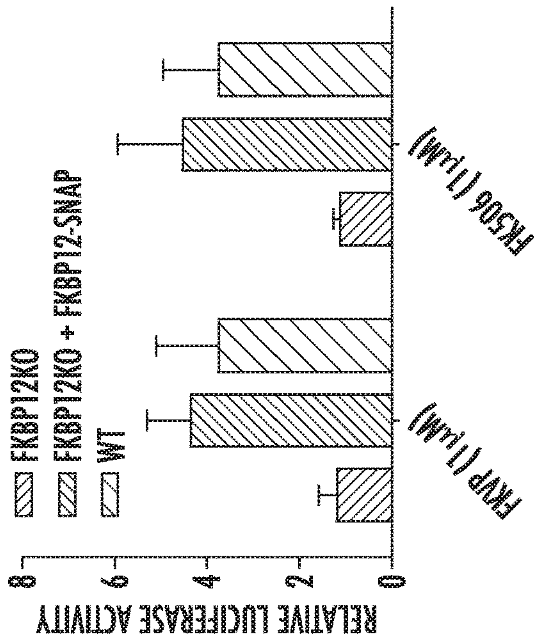
Figure 16D:
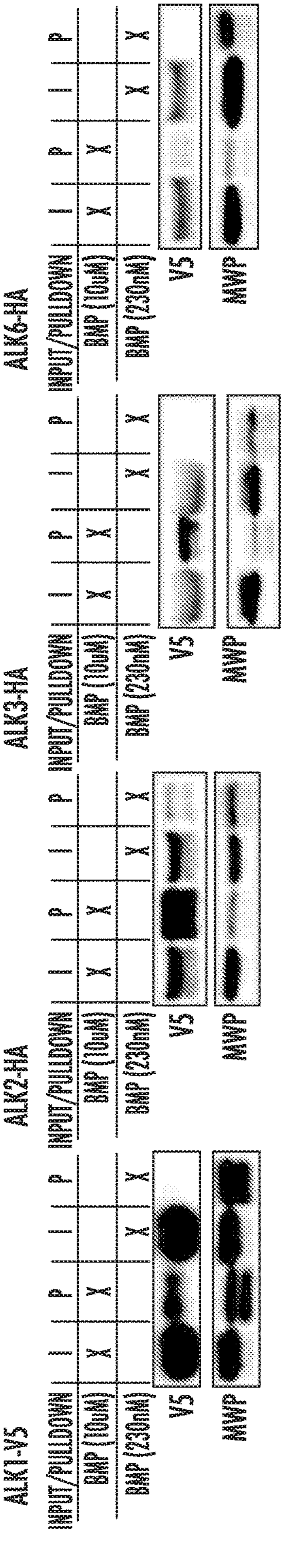
Figure 17:
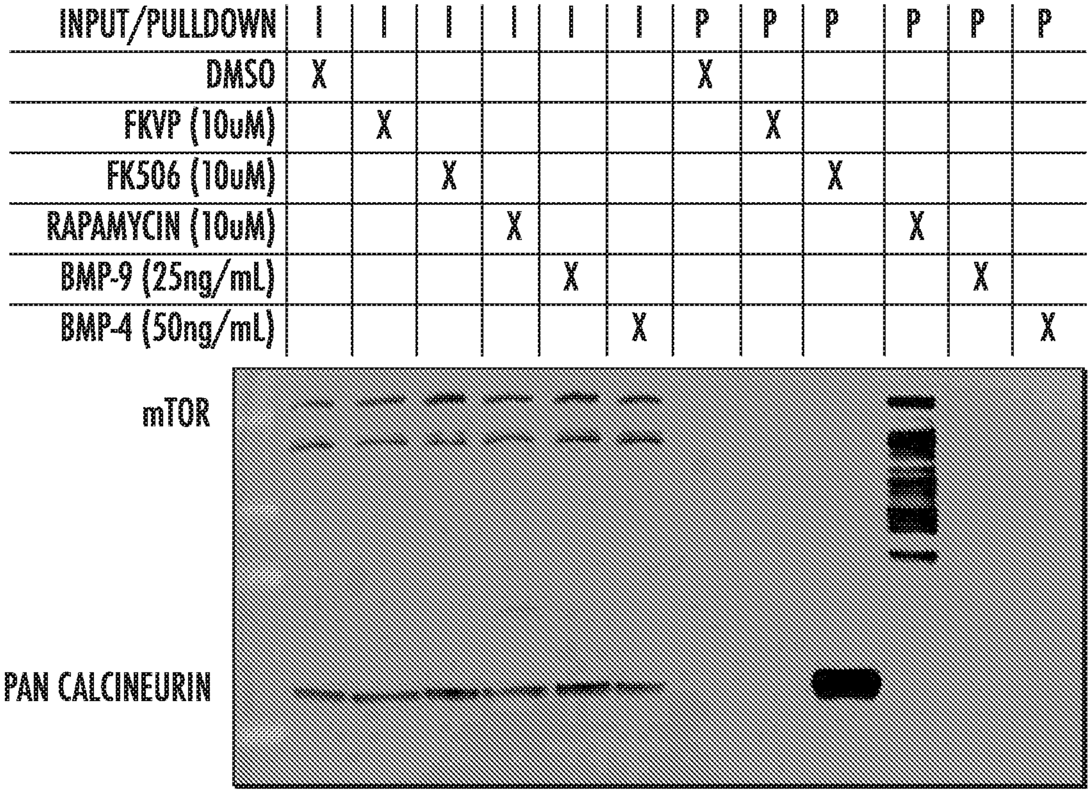
FIG. 17 illustrates that FKBP12-SNAP interacts with both mTOR and calcineurin. SNAP-tag pull-down and Western blot showing that FKBP12-SANP efficiently associates with both calcineurin and mTOR in the presence of FK506 and rapamycin, respectively. As a negative control, FKVP does not induce calcineurin association. BMP protein treatments were not probed for this experiment.

FKBP12 is a member of the FKBP superfamily of proteins. In previous work, FKBP12 has been shown to be associated with the BMPR1 activin-like kinase 2 (ALK2). However, attempts to knock down several FKBPs failed to reveal a specific effect on BMPR1 signaling (Spiekerkoetter et al., 2013), likely due to the relative stability and high abundance of FKBPs. To address this problem, we generated CRISPR-Cas9 knockouts of three cytosolic FKBPs, FKBP12, FKBP51, and FKBP52. All three proteins have been reported to bind FK506 (Kozany et al., 2009), and in the BRE-luciferase reporter assay, it was found that only FKBP12 knockout cells lost sensitivity to FK506 and FKVP (FIGS. 16*a*, 16*b*). It can also be seen that FKBP12KO cells showed constitutively elevated levels of SMAD1/5 phosphorylation (FIG. 16*a*), explaining the low value of BMP-4 treatment in FKBP12KO cells relative to an already-elevated DMSO treated sample. Moreover, reconstitution of FKBP12 by a novel SNAP-tagged fusion construct restored FK506/FKVP sensitivity in KO cells to that of the original parental line (FIG. 16*c*). We were able to use this fusion protein to pull down calcineurin and mTOR in the presence of FK506 and rapamycin, respectively, suggesting that the fused SNAP tag did not interfere with the interactions of the FKBP12-FK506 and the FKBP12-rapamycin complexes with calcineurin or mTOR (FIG. 17). We then applied the same construct to pull down V5- or HA-tagged ALK receptors from transfected HEK293T cells. We observed that the SNAP-FKBP12 and ALK receptors did indeed interact with each other and the association was sensitive to competition by FKVP (FIG. 16*d*). These observations strongly suggest that FKBP12-BMPR1 interaction is solely responsible for mediating the effect of FKVP-induced BMP activation.

Example 9

Figure 18A:
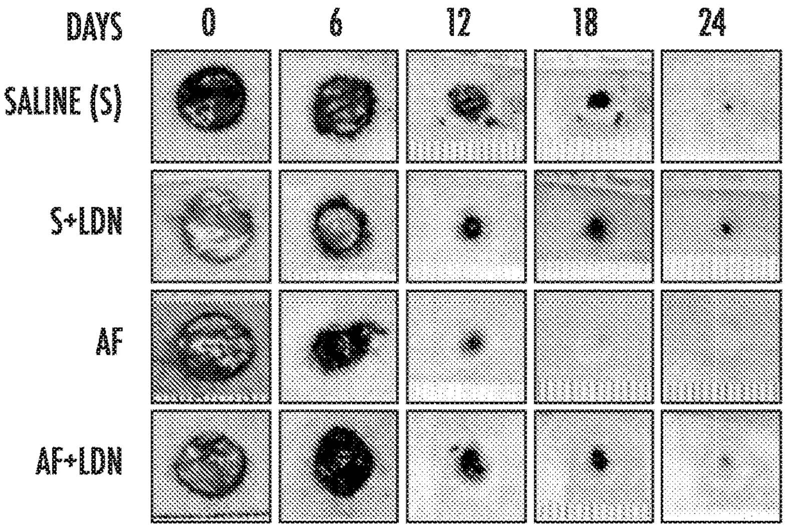
FIGS. 18A-18C show that blockade of BMP signaling abrogates the beneficial effect of AF combination therapy in wound healing.
Figure 18B:
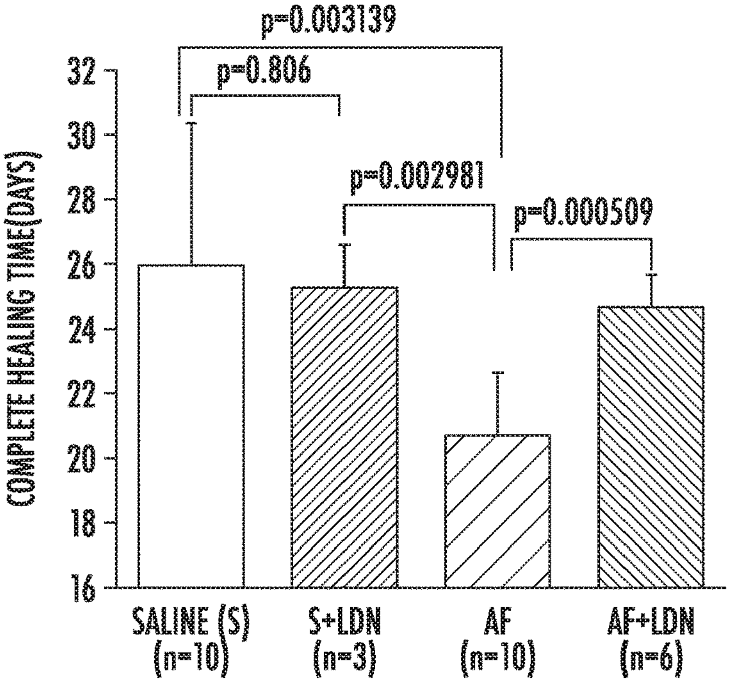
Figure 18C:
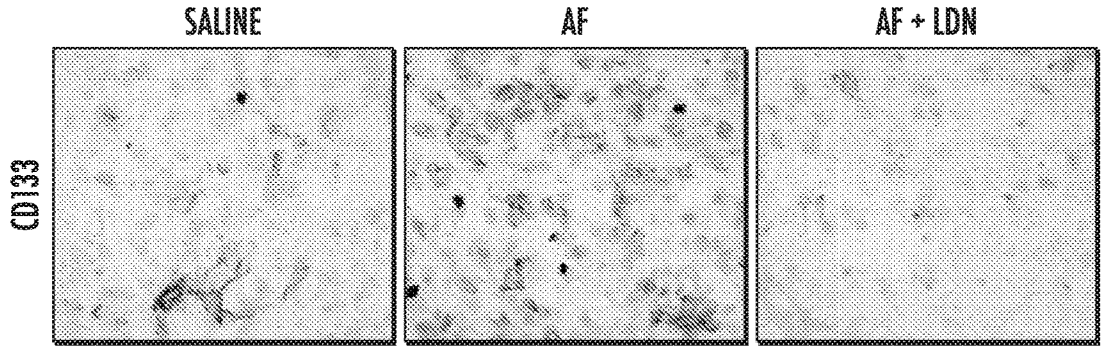

BMP Signaling is Required for the Effect of AF Combination in Accelerating Wound Healing To determine if BMP activation by FK506 is responsible for accelerated wound healing, a selective BMPR1 kinase inhibitor, LDN-193189 (2 mg/kg/day, i.p.) was administered to wounded GK rats treated with saline or AF combination. LDN has been shown effective in vivo (Cuny et al., 2008; Sun et al., 2013), and alone showed no effect on wound healing. Interestingly, LDN abolished the beneficial effect of AF combination therapy and increased the time for complete healing from 21 to 25 days (FIGS. 18*a*, 18*b*). We have reported that FK506 plays a key role in recruitment of AMD3100 mobilized CD133 stem cells into wound sites (Lin et al., 2014) or injured organs (Okabayashi et al., 2011; Hu et al., 2016; Cameron et al., 2016; Zhai et al., 2018). To further confirm if blocking BMP signaling inhibits the recruitment of stem cells, we performed immunohistochemistry staining for CD133 in wound tissue sections recovered from animals at day 7 after surgery. A few CD133+ cells were identified in wound tissue sections from animals treated with saline (FIG. 18*c*). The number of CD133+ cells was significantly increased in newly formed granulation tissues of the wounds in animals receiving AF combination therapy. Strikingly, administration of BMP inhibitor LDN dramatically reduced the number of CD133+ cells in the wounds in animals with AF combination treatment. Taken together, these results suggest that the recruitment of more CD133+ stem cells into the wound sites by AF combination treatment depends on BMP activation by FK506, and that blockade of BMP signaling with LDN eliminates the beneficial effect of AF combination therapy.

Figure 19:
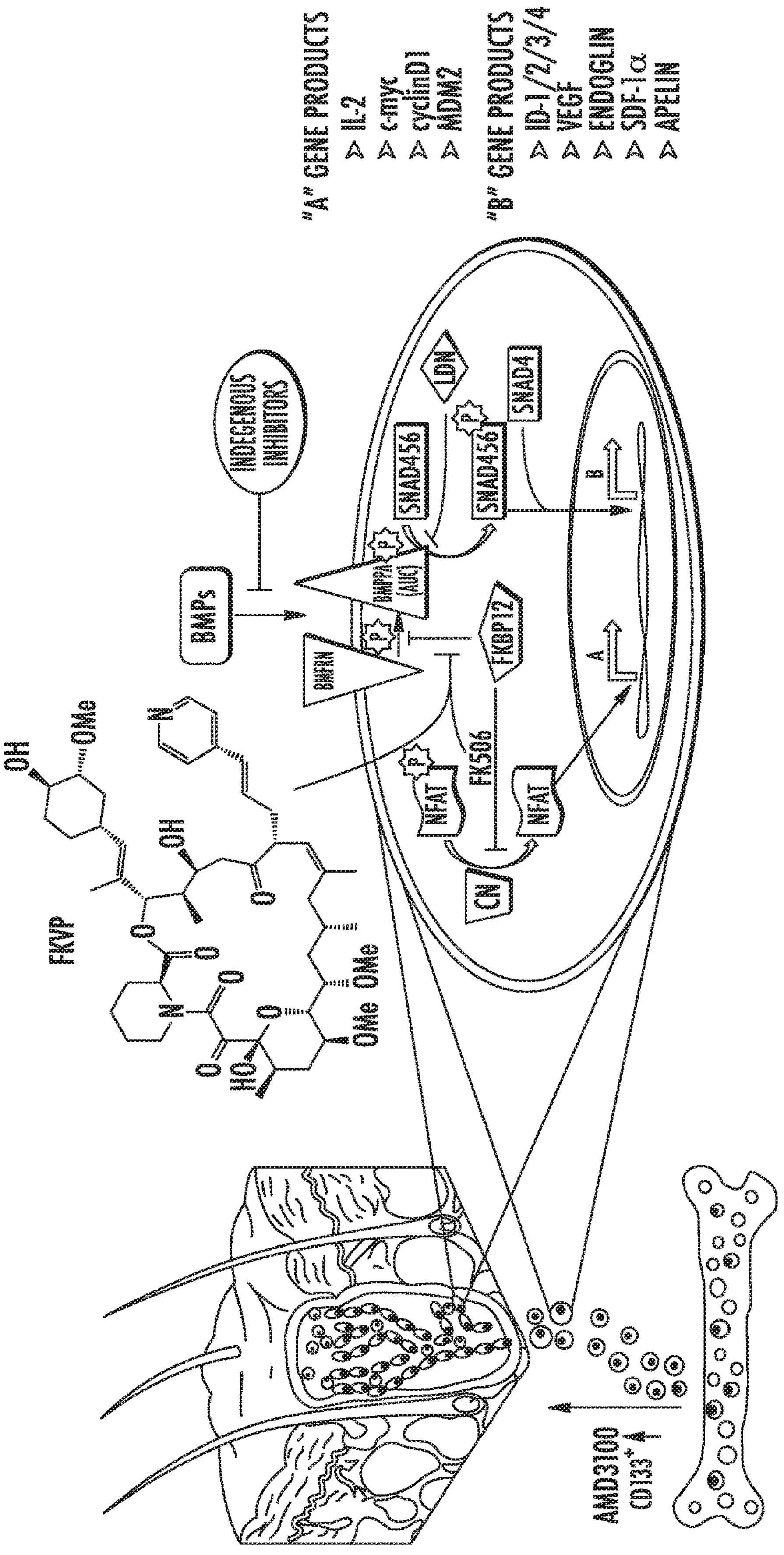
FIG. 19. Without being held to any particular theory, the illustration shows a mechanistic overview of enhanced healing by exemplary compound of formula I, FKVP, and the stem cell stimulator, AMD3100, of the present invention. AMD3100 releases CD133+stem cells into circulation, where FKVP-mediated BMP activation influences recruitment to wounded tissues. Systemic inhibition of FKBP12 by FKVP allows for BMP-related gene expression in both mobilized stem/progenitor cells and the endothelium without affecting the necessary immune responses to wounding.

The inventors investigated the mechanism by which FK506 accelerated WH when used in combination with AMD3100. Using FKVP, a novel, non-immunosuppressive analog of FK506, we ruled out calcineurin as a mediator of both WH acceleration, raising the possibility that FKBPs are the primary target for both effects. Moreover, we demonstrated that macrocyclic FKBP ligands activate BMP signaling by relieving the inhibition of BMPR1 by endogenous FKBP12. We show that FKBP12 plays an essential role in the BMP signaling pathway, an effect that can be mediated without calcineurin inhibition through the use of non-immunosupressive FK506 analogs. We found that BMP receptor signaling is required for wound healing enhancement by FK506, and that blocking this activation results in fewer numbers of stem cells recruited to the wound area. BMP signalling may manipulate several cell types in the wound healing mechanism, such as chemotaxis of stem cells or endothelial adhesion of mobilized cells in the wounded tissue (FIG. 19).

FKBP12, a founding member of the FKBP superfamily, has been shown to possess multiple cellular and physiological functions in addition to its role in mediating inhibition of calcineurin and T cell activation by FK506. The association with, and inhibition by FKBP12 adds another layer of BMPR1 kinase regulation. That relieving FKBP12 inhibition by FK506 or FKVP is sufficient to activate the ID-1luciferase reporter gene suggests that there is a basal level of activity of BMPR that is normally suppressed by FKBP12 and relief of this inhibition leads to significant, albeit moderate, activation of the signaling pathway in comparison to BMP-4 binding. Thus, BMPR may exist in three distinc activation states, upon release of FKBP12 inhibition, upon BMP binding and both. The present invention reveals that the partial activation of BMP pharmacologically with FK506 or FKVP is sufficient to accelerate wound healing in combination with AMD3100.

Type 2 BMP receptors are reported to constitutively phosphorylate the GS domain of type 1 receptors (ALKs). FKBP12 is believed to inhibit random activation of ALKs by binding to residues in the GS domain (Chaikuad et al., 2012). The inventors' results indicated that this association is competed by FKVP for all BMP-specific ALKs. It was shown that loss of FKBP12 results in elevated basal phosphorylation of SMAD1/5, suggesting a partially activated state of ALKs in the absence of its endogenous intracellular inhibitor FKBP12. The additive increase in ID-1 reporter stimulation from concommitant FKVP and rBMP treatment is also consistent the three activation states of BMPR1. Furthermore, addition of the BMP inhibitor noggin did not prevent ID-1 reporter stimulation by FKVP, suggesting that the regulation of BMPR by endogenous FKBP12 is independent of BMP protein-receptor binding.

Inhibition of calcineurin by FK506 has been shown to be responsible for both its potent immunosuppressive activity and a number of its side effects including nephrotoxicity and neurotoxicity (Bechstein et al., 2000, Naesens et al., 2009). By the novel placement of a molecular "bump" on the calcineurin-interacting effector domain of FK506, the resultant FKVP lost its immunosuppressive activity as judged by the NFAT reporter gene assay. In comparision to calcineurin, the loss of function of FKBP12 and other members seems to have much fewer and less drastic impact on both yeast and mammals. Aside from BMP receptors, FKBP12 has been reported to modulate calcium flux in inositol 1,4,5-trisphosphate ($IP_3$) and ryanodine receptors (Cameron et al., 1995; Jayaraman et al., 1992), suggesting FK506 may affect vascular or cardiac smooth muscle contractility. However, calcineurin inhibition alone has been recognized as a key potentiator of hypertension (Hoorn et al., 2012). As such, the non-immunosuppressive FKBP ligands of the present invention should have fewer side effects, resulting in safer and more selective pharmacological BMP agonists. Moreover, FKBP52 inhibition by FK506 has been shown to augment nerve regeneration (Gold, B. G., 1999; Gold, B. G. et al, 1999), suggesting the effect may synergize with FKBP12-mediated tissue regeneration through BMP signalling.

That one of the compounds of formula I, FKVP, is as effective in the enhancement of WH as FK506 also has important clinical implications due to its lack of immunosuppressive effect. In patients with a greater risk of infection, such as those with diabetes, treatment with FKVP will provide effective treatment without the risks associated with immunosupressants. This is higlighted in our use of Goto-Kakazaki rats for this study; a rat model that spontaneously develops type-2 diabetes after 3-4 months of age and suffers from many of the same physiological manifests that affect humans with the disease, including significantly impaired wound healing. By using such a model for this study, we illustrate the power of these compounds of formual I and their use in treatment and its application to clinical use. Our demonstration that FKVP recapitulates the WH efficacy of FK506 in the challenging rat model made FKVP an attractive lead compound, and we can show that other non-immunosuppressive compounds of formula I are devoid of inhibitory activity towards calcineurin similar to FKVP, and possess similar beneficial effects. Furthermore, the synergistic activities of AMD3100 and FKVP demonstrate a regenerative therapy that can be applied to several other types of tissue damage. Beyond WH, our lab has shown improved liver regeneration after partial hepatectomy and AF combination treatment (Zhai et al., 2018). Thus, FKVP and other non-immunosuppressive FKBP12 ligands of the compounds of formula I may find use in both wound healing and regenerative therapies.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

H. Tanaka, A. et al. *J Am. Chem. Soc.*, 1987, 109, 5031; (b) J. J. Fung, Transplantation, 2004, 77, S41.

S. Barik *Cell Mol. Life Sci.*, 2006, 63, 2889.

J. Liu, J. D. Farmer, W. S. Lane, J. Friedman, I. Weissman and S. L. Schreiber, *Cell* 1991, 66, 807; (b) J. P. Griffith et al. *Cell* 1995, 82, 506; (c) C. R. Kissinger et al. *Nature* 1995, 378, 641.

Y. Chen, F. Liu, and J. Massagué, *EMBO J.* 1997, 16, 3866; (b) M. Huse, Y. Chen, J. Massagué, and J. Kuriyan, *Cell* 1999, 96, 425; (c) T. Wang et al. *Cell* 1996, 86, 435; (d) M. S. Rahman, N. Akhtar, H. M. Jamil, R. S. Banik and S. M Asaduzzaman, *Bone Res.* 2015, 3, 15005.

E. Spiekerkoetter et al. *J Clin. Invest.* 2013, 123, 3600.

T. Kawahara et al. *Oncotarget* 2015, 6, 1582.

B. J. Peiffer et at. Unpublished.

P. S. Marinec, C. G. Evans, G. S. Gibbons, M. A. Tamowski, D. L. Overbeek and J. E. Gestwicki *Bioorg. Med. Chem.* 2009, 17, 5763; (b) M. Nambu. et al. *Bioorg. Med. Chem. Lett.* 2017, 27, 2465; (c) Z. Guo, R. Zhang and F. Liang, *RSC Adv.* 2014, 4, 11400; (d) P. A. Clemons, B. G. Gladstone, A. Seth, E. D. Chao, M. A. Foley, and S. L. *Schreiber Chemistry & Biology* 2002, 9, 49.

P. Compain, *Adv. Synth. Catal.* 2007, 349, 1829.

C. P. Woodward, N. D. Spiccia, W. R. Jackson and A. J. Robinson, *Chem. Commun.* 2011, 47, 779

R. F. Heck and J. P. Nolley, *J. Org. Chem.* 1972, 37, 2320; (b) T. Mizoroki, K. Mori and A.

Ozaki, *Bull. Chem. Soc. Jap.* 1971, 44, 581; (c) R. F. Heck, *Org. React.* 1982, 27, 345; (d) A. de Meijere and F. E. Meyer *Angew. Chem. Int. Ed. Engl.* 1994, 33, 2379; (e) I. P. Beletskaya and A. V. Cheprakov, *Chem. Rev.* 2000, 100, 3009.

Abranham, R. T., and Wiederrecht, G. J. (1996). Immunopharmacology of rapamycin. Annu. Rev. Immunol. 14, 483-510.

Albiñana, V., Sanz-Rodríguez, F., Recio-Poveda, L., Bernabéu, C., and Botella, L. M. (2011). Immunosuppressor FK506 increases endoglin and activin receptor-like kinase 1 expression and modulates transforming growth factor-β1 signaling in endothelial cells. Mol. Pharmacol. 79, 833-843.

Balaji, S., King, A., Crombleholme, T. M., and Keswani, S. G. (2013). The Role of Endothelial Progenitor Cells in Postnatal Vasculogenesis: Implications for Therapeutic Neovascularization and Wound Healing. Adv Wound Care (New Rochelle) 2, 283-295. Bechstein, W. O. (2000). Neurotoxicity of calcineurin inhibitors: impact and clinical management. Transpl. Int. 13, 313-326.

Bennett, J., Cassidy, H., Slattery, C., Ryan, M. P., and McMorrow, T. (2016). Tacrolimus Modulates TGF-β Signaling to Induce Epithelial-Mesenchymal Transition in Human Renal Proximal Tubule Epithelial Cells. Journal of Clinical Medicine 5, 50.

Bueno, O. F., Brandt, E. B., Rothenberg, M. E., and Molkentin, J. D. (2002). Defective T cell development and function in calcineurin A beta-deficient mice. Proc. Natl. Acad. Sci. U.S.A. 99, 9398-9403.

Cameron, A. M., Steiner, J. P., Sabatini, D. M., Kaplin, A. I., Walensky, L. D., and Snyder, S. H. (1995). Immunophilin FK506 binding protein associated with inositol 1,4,5-trisphosphate receptor modulates calcium flux. PNAS 92, 1784-1788.
Cameron, A. M., Wesson, R. N., Ahmadi, A. R., Singer, A. L., Hu, X., Okabayashi, T., Wang, Y., Shigoka, M., Fu, Y., Gao, W., et al. (2016). Chimeric Allografts Induced by Short-Term Treatment With Stem Cell Mobilizing Agents Result in Long-Term Kidney Transplant Survival Without Immunosuppression: II, Study in Miniature Swine. Am. J. Transplant. 16, 2066-2076.
Chaikuad, A., Alfano, I., Kerr, G., Sanvitale, C. E., Boergermann, J. H., Triffitt, J. T., Delft, F. von, Knapp, S., Knaus, P., and Bullock, A. N. (2012). Structure of the Bone Morphogenetic Protein Receptor ALK2 and Implications for Fibrodysplasia Ossificans Progressiva. J. Biol. Chem. 287, 36990-36998.
Chen, Y. G., Liu, F., and Massague, J. (1997). Mechanism of TGFbeta receptor inhibition by FKBP12. EMBO J 16, 3866-3876.
Clemons, P. A., Gladstone, B. G., Seth, A., Chao, E. D., Foley, M. A., and Schreiber, S. L. (2002). Synthesis of calcineurin-resistant derivatives of FK506 and selection of compensatory receptors. Chem. Biol. 9, 49-61.
Csiszar, A., Ahmad, M., Smith, K. E., Labinskyy, N., Gao, Q., Kaley, G., Edwards, J. G., Wolin, M. S., and Ungvari, Z. (2006). Bone Morphogenetic Protein-2 Induces Proinflammatory Endothelial Phenotype. Am J Pathol 168, 629-638.
Cuny, G. D., Yu, P. B., Laha, J. K., Xing, X., Liu, J.-F., Lai, C. S., Deng, D. Y., Sachidanandan, C., Bloch, K. D., and Peterson, R. T. (2008). Structure-activity relationship study of bone morphogenetic protein (BMP) signaling inhibitors. Bioorg Med Chem Lett 18, 4388-4392. Fife, C. E., and Carter, M. J. (2012). Wound Care Outcomes and Associated Cost Among Patients Treated in US Outpatient Wound Centers: Data From the US Wound Registry. Wounds 24, 10-17.
Fung, J. J. (2004). Tacrolimus and transplantation: a decade in review. Transplantation 77, S41-43.
Giordano, A., Romano, S., Mallardo, M., D'Angelillo, A., Cali, G., Corcione, N., Ferraro, P., and Romano, M. F. (2008). FK506 can activate transforming growth factor-beta signalling in vascular smooth muscle cells and promote proliferation. Cardiovasc. Res. 79, 519-526.
Gold, B. G. (1999). FK506 and the role of the immunophilin FKBP-52 in nerve regeneration. Drug Metab. Rev. 31, 649-663.
Gold, B. G., Densmore, V., Shou, W., Matzuk, M. M., and Gordon, H. S. (1999). Immunophilin FK506-binding protein 52 (not FK506-binding protein 12) mediates the neurotrophic action of FK506. J. Pharmacol. Exp. Ther. 289, 1202-1210.
Griffith, J. P., Kim, J. L., Kim, E. E., Sintchak, M. D., Thomson, J. A., Fitzgibbon, M. J., Fleming, M. A., Caron, P. R., Hsiao, K., and Navia, M. A. (1995). X-ray structure of calcineurin inhibited by the immunophilin-immunosuppressant FKBP12-FK506 complex. Cell 82, 507-522.
Hatse, S., Princen, K., Bridger, G., De Clercq, E., and Schols, D. (2002). Chemokine receptor inhibition by AMD3100 is strictly confined to CXCR4. FEBS Lett. 527, 255-262. Hoorn, E. J., Walsh, S. B., McCormick, J. A., Zietse, R., Unwin, R. J., and Ellison, D. H. (2012). Pathogenesis of calcineurin inhibitor-induced hypertension. J. Nephrol. 25, 269-275.
Hu, X., Okabayashi, T., Cameron, A. M., Wang, Y., Hisada, M., Li, J., Raccusen, L. C., Zheng, Q., Montgomery, R. A., Williams, G. M., et al. (2016). Chimeric Allografts Induced by Short-Term Treatment With Stem Cell-Mobilizing Agents Result in Long-Term Kidney Transplant Survival Without Immunosuppression: A Study in Rats. Am. J. Transplant. 16, 2055-2065.
Jayaraman, T., Brillantes, A. M., Timerman, A. P., Fleischer, S., Erdjument-Bromage, H., Tempst, P., and Marks, A. R. (1992). FK506 binding protein associated with the calcium release channel (ryanodine receptor). J. Biol. Chem. 267, 9474-9477.
Jujo, K., Hamada, H., Iwakura, A., Thome, T., Sekiguchi, H., Clarke, T., Ito, A., Misener, S., Tanaka, T., Klyachko, E., et al. (2010). CXCR4 blockade augments bone marrow progenitor cell recruitment to the neovasculature and reduces mortality after myocardial infarction. Proc. Natl. Acad. Sci. U.S.A. 107, 11008-11013.
Kissinger, C. R., Parge, H. E., Knighton, D. R., Lewis, C. T., Pelletier, L. A., Tempczyk, A., Kalish, V. J., Tucker, K. D., Showalter, R. E., and Moomaw, E. W. (1995). Crystal structures of human calcineurin and the human FKBP12-FK506-calcineurin complex. Nature 378, 641-644.
Kozany, C., Marz, A., Kress, C., and Hausch, F. (2009). Fluorescent probes to characterise FK506-binding proteins. Chembiochem 10, 1402-1410.
Lewis, C. J., Mardaryev, A. N., Poterlowicz, K., Sharova, T. Y., Aziz, A., Sharpe, D. T., Botchkareva, N. V., and Sharov, A. A. (2014). Bone morphogenetic protein signaling suppresses wound-induced skin repair by inhibiting keratinocyte proliferation and migration. J. Invest. Dermatol. 134, 827-837.
Liles, W. C., Broxmeyer, H. E., Rodger, E., Wood, B., Hibel, K., Cooper, S., Hangoc, G., Bridger, G. J., Henson, G. W., Calandra, G., et al. (2003). Mobilization of hematopoietic progenitor cells in healthy volunteers by AMD3100, a CXCR4 antagonist. Blood 102, 2728-2730.
Lin, Q., Wesson, R. N., Maeda, H., Wang, Y., Cui, Z., Liu, J. O., Cameron, A. M., Gao, B., Montgomery, R. A., Williams, G. M., et al. (2014). Pharmacological mobilization of endogenous stem cells significantly promotes skin regeneration after full-thickness excision: the synergistic activity of AMD3100 and tacrolimus. J. Invest. Dermatol. 134, 2458-2468. Liu, J., Farmer, J. D., Lane, W. S., Friedman, J., Weissman, I., and Schreiber, S. L. (1991). Calcineurin is a common target of cyclophilin-cyclosporin A and FKBP-FK506 complexes. Cell 66, 807-815.
Mueller, T. D., and Nickel, J. (2012). Promiscuity and specificity in BMP receptor activation. FEBS Letters 586, 1846-1859.
Naesens, M., Kuypers, D. R. J., and Sarwal, M. (2009). Calcineurin Inhibitor Nephrotoxicity. CJASN 4, 481-508.
Okabayashi, T., Cameron, A. M., Hisada, M., Montgomery, R. A., Williams, G. M., and Sun, Z. (2011). Mobilization of host stem cells enables long-term liver transplant acceptance in a strongly rejecting rat strain combination. Am. J. Transplant. 11, 2046-2056.
Plikus, M. V., Guerrero-Juarez, C. F., Ito, M., Li, Y. R., Dedhia, P. H., Zheng, Y., Shao, M., Gay, D. L., Ramos, R., Hsi, T.-C., et al. (2017). Regeneration of fat cells from myofibroblasts during wound healing. Science 355, 748-752.
Rao, A., Luo, C., and Hogan, P. G. (1997). Transcription factors of the NFAT family: regulation and function. Annu. Rev. Immunol. 15, 707-747.
Schaffer, M. R., Fuchs, N., Proksch, B., Bongartz, M., Beiter, T., and Becker, H. D. (1998). Tacrolimus impairs wound healing: a possible role of decreased nitric oxide synthesis. Transplantation 65, 813-818.

Shin, K., Lim, A., Zhao, C., Sahoo, D., Pan, Y., Spiekerkoetter, E., Liao, J. C., and Beachy, P. A. (2014). Hedgehog Signaling Restrains Bladder Cancer Progression by Eliciting Stromal Production of Urothelial Differentiation Factors. Cancer Cell 26, 521-533.

Spiekerkoetter, E., Tian, X., Cai, J., Hopper, R. K., Sudheendra, D., Li, C. G., El-Bizri, N., Sawada, H., Haghighat, R., Chan, R., et al. (2013). FK506 activates BMPR2, rescues endothelial dysfunction, and reverses pulmonary hypertension. J. Clin. Invest. 123, 3600-3613.

Sun, C. C., Vaja, V., Chen, S., Theurl, I., Stepanek, A., Brown, D. E., Cappellini, M. D., Weiss, G., Hong, C. C., Lin, H. Y., et al. (2013). A hepcidin lowering agent mobilizes iron for incorporation into red blood cells in an adenine-induced kidney disease model of anemia in rats. Nephrol Dial Transplant 28, 1733-1743.

Tanaka, H., Kuroda, A., Marusawa, H., Hatanaka, H., Kino, T., Goto, T., Hashimoto, M., and Taga, T. (1987). Structure of FK506, a novel immunosuppressant isolated from *Streptomyces*. J. Am. Chem. Soc. 109, 5031-5033.

Tateishi, K., Higuchi, C., Ando, W., Nakata, K., Hashimoto, J., Hart, D. A., Yoshikawa, H., and Nakamura, N. (2007). The immunosuppressant FK506 promotes development of the chondrogenic phenotype in human synovial stromal cells via modulation of the Smad signaling pathway. Osteoarthritis and Cartilage 15, 709-718.

Wang, T., Li, B. Y., Danielson, P. D., Shah, P. C., Rockwell, S., Lechleider, R. J., Martin, J., Manganaro, T., and Donahoe, P. K. (1996). The immunophilin FKBP12 functions as a common inhibitor of the TGF beta family type I receptors. Cell 86, 435-444.

Young, K., Conley, B., Romero, D., Tweedie, E., O'Neill, C., Pinz, I., Brogan, L., Lindner, V., Liaw, L., and Vary, C. P. H. (2012). BMP9 regulates endoglin-dependent chemokine responses in endothelial cells. Blood 120, 4263-4273.

Zhai, R., Wang, Y., Qi, L., Williams, G. M., Gao, B., Song, G., Burdick, J. F., and Sun, Z. (2018). Pharmacological Mobilization of Endogenous Bone Marrow Stem Cells Promotes Liver Regeneration after Extensive Liver Resection in Rats. Scientific Reports 8, 3587.

The invention claimed is:

1. A non-immunosuppressive compound of formula I:

(I)

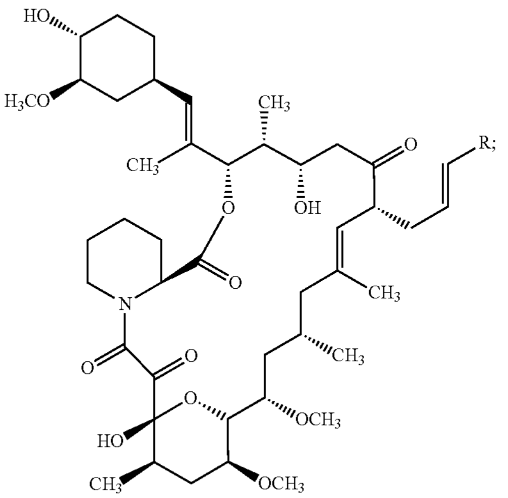

a or a salt, solvate, or isomer thereof, wherein R is selected from (1)

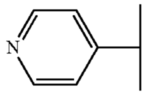

;

(2)

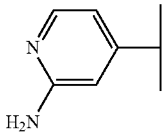

;

(3)

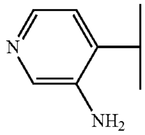

;

(5)

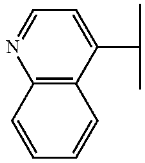

;

(12)

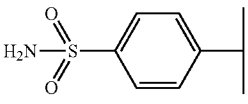

;

(18)

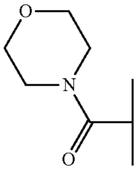

; or (19)

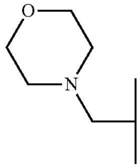

.

2. A composition comprising a non-immunosuppressive compound of formula I:

(I)

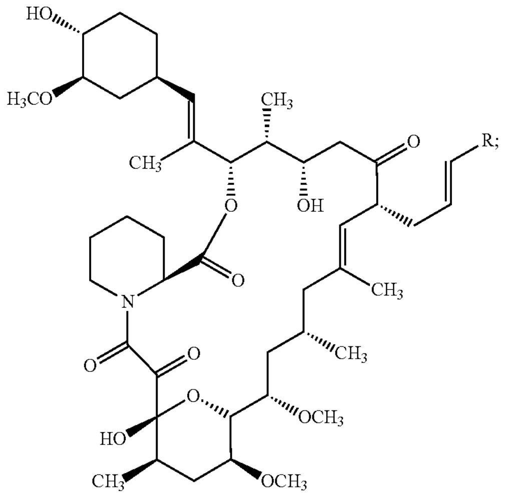

a or a salt, solvate, or isomer thereof, wherein R is selected from (1)

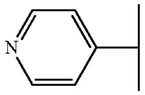

;

(2)

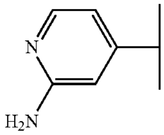

;

(3)

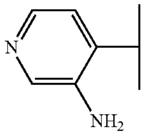

;

(5)

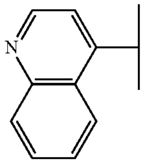

;

(12)

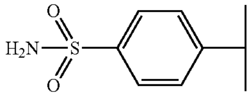

;

(18)

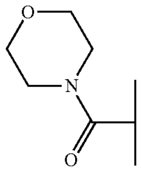

; or

-continued (19)

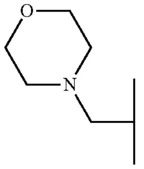

.

3. The composition of claim 2, further comprising a biologically active agent.

4. A composition comprising a non-immunosuppressive compound of formula I:

(I)

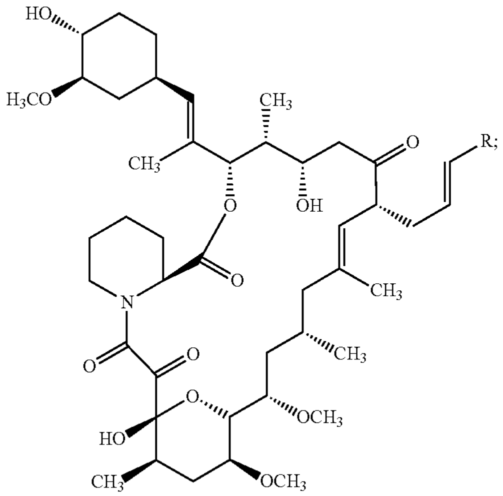

a or a salt, solvate, or isomer thereof, wherein R is selected from (1)

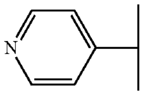

;

(2)

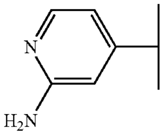

;

(3)

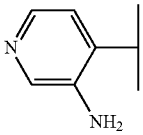

;

(5)

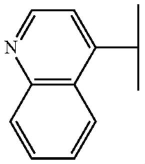

;

-continued
(12)
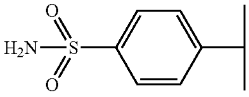
;
(18)
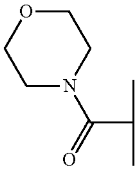
; or
(19)
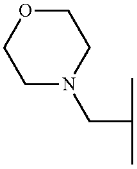
;
at least one stem cell mobilizer; and a pharmaceutically acceptable carrier.
5. The composition of claim 4, wherein the stem cell mobilizer comprises a CXCR4 antagonist.
6. The composition of claim 5, wherein the CXCR4 antagonist is AMD3100, TG-0054, or AMD3465.
* * * * *